(12) United States Patent
Betelia et al.

(10) Patent No.: US 12,616,490 B2
(45) Date of Patent: May 5, 2026

(54) SYSTEMS, DEVICES, AND METHODS FOR TREATMENT OF TARGET MATERIAL IN A BODY LUMEN WITH SHOCK WAVES

(71) Applicant: Shockwave Medical, Inc., Santa Clara, CA (US)

(72) Inventors: Rainier Betelia, San Jose, CA (US); Thomas Charles Hasenberg, Campbell, CA (US); Daryl Wong, San Jose, CA (US); Thu Anh Ho, San Jose, CA (US); Robert Zelenka, Milpitas, CA (US)

(73) Assignee: SHOCKWAVE MEDICAL, INC., Santa Clara, CA (US)

( * ) Notice: Subject to any disclaimer, the term of this patent is extended or adjusted under 35 U.S.C. 154(b) by 0 days.

(21) Appl. No.: 18/960,815

(22) Filed: Nov. 26, 2024

(65) Prior Publication Data

US 2025/0176987 A1 Jun. 5, 2025

Related U.S. Application Data

(60) Provisional application No. 63/604,359, filed on Nov. 30, 2023.

(51) Int. Cl.
| | |
|---|---|
| *A61B 17/22* | (2006.01) |
| *A61B 17/32* | (2006.01) |
| *A61M 25/00* | (2006.01) |
| *A61N 1/362* | (2006.01) |

(52) U.S. Cl.
CPC .. *A61B 17/22022* (2013.01); *A61B 17/32002* (2013.01); *A61B 2017/22025* (2013.01); *A61B 2017/22028* (2013.01); *A61B 2017/22038* (2013.01); *A61M 25/0082* (2013.01); *A61N 1/362* (2013.01)

(58) Field of Classification Search
CPC ................... A61B 17/22012; A61B 17/22022
See application file for complete search history.

(56) References Cited

U.S. PATENT DOCUMENTS

| | | |
|---|---|---|
| 2,916,647 A | 12/1959 | George |
| 3,412,288 A | 11/1968 | Ostrander |
| 3,413,976 A | 12/1968 | Roze |
| 3,524,101 A | 8/1970 | Barbini |
| 3,583,766 A | 6/1971 | Padberg |
| 3,785,382 A | 1/1974 | Schmidt-Kloiber et al. |

(Continued)

FOREIGN PATENT DOCUMENTS

| | | |
|---|---|---|
| AU | 2009313507 B2 | 11/2014 |
| AU | 2013284490 B2 | 5/2018 |

(Continued)

OTHER PUBLICATIONS

International Search Report and Written Opinion received for International Patent Application No. PCT/US2024/057793 mailed on Mar. 23, 2025, 13 pages.

*Primary Examiner* — Ashley L Fishback
(74) *Attorney, Agent, or Firm* — Morrison & Foerster LLP

(57) ABSTRACT

A catheter includes a catheter body; at least one shock wave emitter disposed on the catheter body; and a moveable shield extending at least partially around the catheter body and configured for translating along the catheter body. Exemplary catheters are configured to modify lesions, including fibrotic and calcified tissue buildup within the body.

31 Claims, 18 Drawing Sheets

(56)                References Cited

U.S. PATENT DOCUMENTS

| | | | |
|---|---|---|---|
| 3,902,499 A | 9/1975 | Shene |
| 3,942,531 A | 3/1976 | Hoff et al. |
| 4,027,674 A | 6/1977 | Tessler et al. |
| 4,030,505 A | 6/1977 | Tessler |
| 4,445,509 A | 5/1984 | Auth |
| 4,662,126 A | 5/1987 | Malcolm |
| 4,662,375 A | 5/1987 | Hepp et al. |
| 4,671,254 A | 6/1987 | Fair |
| 4,685,458 A | 8/1987 | Leckrone |
| 4,741,405 A | 5/1988 | Moeny et al. |
| 4,809,682 A | 3/1989 | Forssmann et al. |
| 4,813,934 A | 3/1989 | Engelson et al. |
| 4,878,495 A | 11/1989 | Grayzei |
| 4,890,603 A | 1/1990 | Filler |
| 4,900,303 A | 2/1990 | Lemelson |
| 4,990,134 A | 2/1991 | Auth |
| 4,994,032 A | 2/1991 | Sugiyama et al. |
| 5,009,232 A | 4/1991 | Hassler et al. |
| 5,046,503 A | 9/1991 | Schneiderman |
| 5,057,103 A | 10/1991 | Davis |
| 5,057,106 A | 10/1991 | Kasevich et al. |
| 5,061,240 A | 10/1991 | Cherian |
| 5,078,717 A | 1/1992 | Parins et al. |
| 5,102,402 A | 4/1992 | Dror et al. |
| 5,103,804 A | 4/1992 | Abele et al. |
| 5,116,227 A | 5/1992 | Levy |
| 5,152,767 A | 10/1992 | Sypal et al. |
| 5,152,768 A | 10/1992 | Bhatta |
| 5,154,722 A | 10/1992 | Filip et al. |
| 5,176,675 A | 1/1993 | Watson et al. |
| 5,195,508 A | 3/1993 | Muller et al. |
| 5,245,988 A | 9/1993 | Einars et al. |
| 5,246,447 A | 9/1993 | Rosen et al. |
| 5,254,121 A | 10/1993 | Manevitz et al. |
| 5,281,231 A | 1/1994 | Rosen et al. |
| 5,295,958 A | 3/1994 | Shturman |
| 5,304,134 A | 4/1994 | Kraus et al. |
| 5,321,715 A | 6/1994 | Trost |
| 5,324,255 A | 6/1994 | Passafaro et al. |
| 5,336,234 A | 8/1994 | Vigil et al. |
| 5,362,309 A | 11/1994 | Carter |
| 5,364,393 A | 11/1994 | Auth et al. |
| 5,368,591 A | 11/1994 | Lennox et al. |
| 5,395,335 A | 3/1995 | Jang |
| 5,417,208 A | 5/1995 | Winkler |
| 5,425,735 A | 6/1995 | Rosen et al. |
| 5,454,809 A | 10/1995 | Janssen |
| 5,472,406 A | 12/1995 | de la Torre et al. |
| 5,582,578 A | 12/1996 | Zhong et al. |
| 5,584,843 A | 12/1996 | Wulfman et al. |
| 5,603,731 A | 2/1997 | Whitney |
| 5,609,606 A | 3/1997 | O'Boyle |
| 5,662,590 A | 9/1997 | de la Torre et al. |
| 5,709,676 A | 1/1998 | Alt |
| 5,846,218 A | 12/1998 | Brisken et al. |
| 5,891,089 A | 4/1999 | Katz et al. |
| 5,893,840 A | 4/1999 | Hull et al. |
| 5,931,805 A | 8/1999 | Brisken |
| 6,007,530 A | 12/1999 | Dornhofer et al. |
| 6,033,371 A | 3/2000 | Torre et al. |
| 6,056,722 A | 5/2000 | Jayaraman |
| 6,080,119 A | 6/2000 | Schwarze et al. |
| 6,083,232 A | 7/2000 | Cox |
| 6,090,104 A | 7/2000 | Webster et al. |
| 6,113,560 A | 9/2000 | Simnacher |
| 6,132,444 A | 10/2000 | Shturman et al. |
| 6,146,358 A | 11/2000 | Rowe |
| 6,186,963 B1 | 2/2001 | Schwarze et al. |
| 6,210,408 B1 | 4/2001 | Chandrasekaran et al. |
| 6,215,734 B1 | 4/2001 | Moeny et al. |
| 6,217,531 B1 | 4/2001 | Reitmajer |
| 6,267,747 B1 | 7/2001 | Samson et al. |
| 6,277,138 B1 | 8/2001 | Levinson et al. |
| 6,287,272 B1 | 9/2001 | Brisken et al. |
| 6,352,535 B1 | 3/2002 | Lewis et al. |
| 6,364,894 B1 | 4/2002 | Healy et al. |
| 6,367,203 B1 | 4/2002 | Graham et al. |
| 6,371,971 B1 | 4/2002 | Tsugita et al. |
| 6,398,792 B1 | 6/2002 | O'Connor |
| 6,406,486 B1 | 6/2002 | de la Torre et al. |
| 6,440,124 B1 | 8/2002 | Esch et al. |
| 6,494,890 B1 | 12/2002 | Shturman et al. |
| 6,514,203 B2 | 2/2003 | Bukshpan |
| 6,524,251 B2 | 2/2003 | Rabiner et al. |
| 6,589,253 B1 | 7/2003 | Cornish et al. |
| 6,607,003 B1 | 8/2003 | Wilson |
| 6,638,246 B1 | 10/2003 | Naimark et al. |
| 6,652,547 B2 | 11/2003 | Rabiner et al. |
| 6,666,834 B2 | 12/2003 | Restle et al. |
| 6,689,089 B1 | 2/2004 | Tiedtke et al. |
| 6,736,784 B1 | 5/2004 | Menne et al. |
| 6,740,081 B2 | 5/2004 | Hilal |
| 6,755,821 B1 | 6/2004 | Fry |
| 6,939,320 B2 | 9/2005 | Lennox |
| 6,989,009 B2 | 1/2006 | Lafontaine |
| 7,066,904 B2 | 6/2006 | Rosenthal et al. |
| 7,087,061 B2 | 8/2006 | Chernenko et al. |
| 7,241,295 B2 | 7/2007 | Maguire |
| 7,309,324 B2 | 12/2007 | Hayes et al. |
| 7,389,148 B1 | 6/2008 | Morgan |
| 7,505,812 B1 | 3/2009 | Eggers et al. |
| 7,569,032 B2 | 8/2009 | Naimark et al. |
| 7,850,685 B2 | 12/2010 | Kunis et al. |
| 7,853,332 B2 | 12/2010 | Olsen et al. |
| 7,873,404 B1 | 1/2011 | Patton |
| 7,951,111 B2 | 5/2011 | Drasler et al. |
| 8,162,859 B2 | 4/2012 | Schultheiss et al. |
| 8,177,801 B2 | 5/2012 | Kallok et al. |
| 8,353,923 B2 | 1/2013 | Shturman |
| 8,556,813 B2 | 10/2013 | Cioanta et al. |
| 8,574,247 B2 | 11/2013 | Adams et al. |
| 8,728,091 B2 | 5/2014 | Hakala et al. |
| 8,747,416 B2 | 6/2014 | Hakala et al. |
| 8,888,788 B2 | 11/2014 | Hakala et al. |
| 8,956,371 B2 | 2/2015 | Hawkins |
| 8,956,374 B2 | 2/2015 | Hawkins et al. |
| 9,005,216 B2 | 4/2015 | Hakala et al. |
| 9,011,462 B2 | 4/2015 | Adams et al. |
| 9,011,463 B2 | 4/2015 | Adams et al. |
| 9,044,618 B2 | 6/2015 | Hawkins et al. |
| 9,044,619 B2 | 6/2015 | Hawkins et al. |
| 9,072,534 B2 | 7/2015 | Hakala et al. |
| 9,138,249 B2 | 9/2015 | Adams et al. |
| 9,198,825 B2 | 12/2015 | Katragadda et al. |
| 9,333,000 B2 | 5/2016 | Hakala et al. |
| 9,421,025 B2 | 8/2016 | Hawkins et al. |
| 9,433,428 B2 | 9/2016 | Hakala et al. |
| 9,522,012 B2 | 12/2016 | Adams |
| 9,642,673 B2 | 5/2017 | Adams et al. |
| 9,993,292 B2 | 6/2018 | Adams et al. |
| 10,039,561 B2 | 8/2018 | Adams et al. |
| 10,118,015 B2 | 11/2018 | De La Rama et al. |
| 10,149,690 B2 | 12/2018 | Hawkins et al. |
| 10,154,799 B2 | 12/2018 | Van Der Weide et al. |
| 10,159,505 B2 | 12/2018 | Hakala et al. |
| 10,206,698 B2 | 2/2019 | Hakala et al. |
| 10,517,620 B2 | 12/2019 | Adams |
| 10,517,621 B1 | 12/2019 | Adams |
| 10,555,744 B2 | 2/2020 | Nguyen et al. |
| 10,682,178 B2 | 6/2020 | Adams et al. |
| 10,702,293 B2 | 7/2020 | Hawkins et al. |
| 10,709,462 B2 | 7/2020 | Nguyen et al. |
| 10,959,743 B2 | 3/2021 | Adams et al. |
| 10,966,737 B2 | 4/2021 | Nguyen |
| 10,973,538 B2 | 4/2021 | Hakala et al. |
| 11,000,299 B2 | 5/2021 | Hawkins et al. |
| 11,076,874 B2 | 8/2021 | Hakala et al. |
| 11,337,713 B2 | 5/2022 | Nguyen et al. |
| 11,432,834 B2 | 9/2022 | Adams |
| 11,478,261 B2 | 10/2022 | Nguyen |
| 11,534,187 B2 | 12/2022 | Bonutti |
| 11,596,423 B2 | 3/2023 | Nguyen et al. |
| 11,596,424 B2 | 3/2023 | Hakala et al. |
| 11,622,780 B2 | 4/2023 | Nguyen et al. |

(56) References Cited

U.S. PATENT DOCUMENTS

| | | | |
|---|---|---|---|
| 11,696,799 | B2 | 7/2023 | Adams et al. |
| 11,771,449 | B2 | 10/2023 | Adams et al. |
| 2001/0044596 | A1 | 11/2001 | Jaafar |
| 2002/0045890 | A1 | 4/2002 | Celliers et al. |
| 2002/0082553 | A1 | 6/2002 | Duchamp |
| 2002/0177889 | A1 | 11/2002 | Brisken et al. |
| 2003/0004434 | A1 | 1/2003 | Greco et al. |
| 2003/0176873 | A1 | 9/2003 | Chernenko et al. |
| 2003/0229370 | A1 | 12/2003 | Miller |
| 2004/0006333 | A1 | 1/2004 | Arnold et al. |
| 2004/0010249 | A1 | 1/2004 | Truckai et al. |
| 2004/0044308 | A1 | 3/2004 | Naimark et al. |
| 2004/0097963 | A1 | 5/2004 | Seddon |
| 2004/0097996 | A1 | 5/2004 | Rabiner et al. |
| 2004/0162508 | A1 | 8/2004 | Uebelacker |
| 2004/0249401 | A1 | 12/2004 | Rabiner et al. |
| 2004/0254570 | A1 | 12/2004 | Hadjicostis et al. |
| 2005/0015953 | A1 | 1/2005 | Keidar |
| 2005/0021013 | A1 | 1/2005 | Visuri et al. |
| 2005/0059965 | A1 | 3/2005 | Eberl et al. |
| 2005/0075662 | A1 | 4/2005 | Pedersen et al. |
| 2005/0090888 | A1 | 4/2005 | Hines et al. |
| 2005/0113722 | A1 | 5/2005 | Schultheiss |
| 2005/0113822 | A1 | 5/2005 | Fuimaono et al. |
| 2005/0171527 | A1 | 8/2005 | Bhola |
| 2005/0228372 | A1 | 10/2005 | Truckai et al. |
| 2005/0245866 | A1 | 11/2005 | Azizi |
| 2005/0251131 | A1 | 11/2005 | Lesh |
| 2006/0004286 | A1 | 1/2006 | Chang et al. |
| 2006/0009737 | A1 * | 1/2006 | Whiting ............ A61M 25/0084 |
| | | | 606/167 |
| 2006/0069424 | A1 | 3/2006 | Acosta et al. |
| 2006/0074484 | A1 | 4/2006 | Huber |
| 2006/0184076 | A1 | 8/2006 | Gill et al. |
| 2006/0190022 | A1 | 8/2006 | Beyar et al. |
| 2006/0221528 | A1 | 10/2006 | Li et al. |
| 2007/0016112 | A1 | 1/2007 | Schultheiss et al. |
| 2007/0088380 | A1 | 4/2007 | Hirszowicz et al. |
| 2007/0129667 | A1 | 6/2007 | Tiedtke et al. |
| 2007/0156129 | A1 | 7/2007 | Kovalcheck |
| 2007/0239082 | A1 | 10/2007 | Schultheiss et al. |
| 2007/0239253 | A1 | 10/2007 | Jagger et al. |
| 2007/0244423 | A1 | 10/2007 | Zumeris et al. |
| 2007/0250052 | A1 | 10/2007 | Wham |
| 2007/0255270 | A1 | 11/2007 | Carney |
| 2007/0282301 | A1 | 12/2007 | Segalescu et al. |
| 2007/0299481 | A1 | 12/2007 | Syed et al. |
| 2008/0097251 | A1 | 4/2008 | Babaev |
| 2008/0188913 | A1 | 8/2008 | Stone et al. |
| 2009/0041833 | A1 | 2/2009 | Bettinger et al. |
| 2009/0227992 | A1 | 9/2009 | Nir et al. |
| 2009/0230822 | A1 | 9/2009 | Kushculey et al. |
| 2009/0247945 | A1 | 10/2009 | Levit et al. |
| 2009/0254114 | A1 | 10/2009 | Hirszowicz et al. |
| 2009/0299447 | A1 | 12/2009 | Jensen et al. |
| 2010/0016862 | A1 | 1/2010 | Hawkins et al. |
| 2010/0036294 | A1 | 2/2010 | Mantell et al. |
| 2010/0094209 | A1 | 4/2010 | Drasler et al. |
| 2010/0114020 | A1 | 5/2010 | Hawkins et al. |
| 2010/0114065 | A1 | 5/2010 | Hawkins et al. |
| 2010/0121322 | A1 | 5/2010 | Swanson |
| 2010/0179424 | A1 | 7/2010 | Warnking et al. |
| 2010/0286709 | A1 | 11/2010 | Diamant et al. |
| 2010/0305565 | A1 | 12/2010 | Truckai et al. |
| 2011/0034832 | A1 | 2/2011 | Cioanta et al. |
| 2011/0118634 | A1 | 5/2011 | Golan |
| 2011/0208185 | A1 | 8/2011 | Diamant et al. |
| 2011/0257523 | A1 | 10/2011 | Hastings et al. |
| 2011/0295227 | A1 | 12/2011 | Hawkins et al. |
| 2012/0071889 | A1 | 3/2012 | Mantell et al. |
| 2012/0095461 | A1 | 4/2012 | Herscher et al. |
| 2012/0116289 | A1 | 5/2012 | Hawkins et al. |
| 2012/0143177 | A1 | 6/2012 | Avitall et al. |
| 2012/0157991 | A1 | 6/2012 | Christian |
| 2012/0203255 | A1 | 8/2012 | Hawkins et al. |
| 2012/0253358 | A1 | 10/2012 | Golan et al. |
| 2013/0030431 | A1 | 1/2013 | Adams |
| 2013/0041355 | A1 | 2/2013 | Heeren et al. |
| 2013/0116714 | A1 | 5/2013 | Adams et al. |
| 2013/0123694 | A1 | 5/2013 | Subramaniyan et al. |
| 2013/0150874 | A1 | 6/2013 | Kassab |
| 2013/0253622 | A1 | 9/2013 | Hooven |
| 2014/0046229 | A1 | 2/2014 | Hawkins et al. |
| 2014/0214061 | A1 | 7/2014 | Adams et al. |
| 2015/0320432 | A1 | 11/2015 | Adams |
| 2016/0151081 | A1 | 6/2016 | Adams et al. |
| 2016/0324534 | A1 | 11/2016 | Hawkins et al. |
| 2017/0135709 | A1 | 5/2017 | Nguyen et al. |
| 2017/0311965 | A1 | 11/2017 | Adams |
| 2019/0090891 | A1 | 3/2019 | Chae |
| 2021/0085383 | A1 | 3/2021 | Vo et al. |
| 2021/0338258 | A1 | 11/2021 | Hawkins et al. |
| 2022/0015785 | A1 | 1/2022 | Hakala et al. |
| 2022/0240958 | A1 | 8/2022 | Nguyen et al. |
| 2022/0346761 | A1 | 11/2022 | Lee et al. |
| 2023/0043475 | A1 | 2/2023 | Adams |
| 2023/0107690 | A1 | 4/2023 | Nguyen |
| 2023/0165598 | A1 | 6/2023 | Nguyen et al. |
| 2023/0190316 | A1 | 6/2023 | Nguyen |
| 2023/0293197 | A1 | 9/2023 | Nguyen et al. |
| 2023/0310073 | A1 | 10/2023 | Adams et al. |
| 2023/0329731 | A1 | 10/2023 | Hakala et al. |
| 2023/0380849 | A1 | 11/2023 | Adams et al. |

FOREIGN PATENT DOCUMENTS

| | | | | |
|---|---|---|---|---|
| CA | 2104414 | A1 | 2/1995 | |
| CN | 1204242 | A | 1/1999 | |
| CN | 1269708 | A | 10/2000 | |
| CN | 1942145 | A | 4/2007 | |
| CN | 101043914 | A | 9/2007 | |
| CN | 102057422 | A | 5/2011 | |
| CN | 102271748 | A | 12/2011 | |
| CN | 102355856 | A | 2/2012 | |
| CN | 102765785 | A | 11/2012 | |
| CN | 203564304 | U | 4/2014 | |
| DE | 3038445 | A1 | 5/1982 | |
| DE | 202006014285 | U1 | 12/2006 | |
| EP | 0442199 | A2 | 8/1991 | |
| EP | 0571306 | A1 | 11/1993 | |
| EP | 623360 | A1 | 11/1994 | |
| EP | 0647435 | A1 | 4/1995 | |
| EP | 2253884 | A1 | 11/2010 | |
| EP | 2362798 | B1 | 4/2014 | |
| EP | 3641672 | B1 * | 9/2021 | ......... A61B 17/2202 |
| JP | S62-099210 | U | 6/1987 | |
| JP | S62-275446 | A | 11/1987 | |
| JP | H03-63059 | A | 3/1991 | |
| JP | H06-125915 | A | 5/1994 | |
| JP | H07-47135 | A | 2/1995 | |
| JP | H08-89511 | A | 4/1996 | |
| JP | H10-99444 | A | 4/1998 | |
| JP | H10-314177 | A | 12/1998 | |
| JP | H10-513379 | A | 12/1998 | |
| JP | 2002538932 | A | 11/2002 | |
| JP | 2004081374 | A | 3/2004 | |
| JP | 2004357792 | A | 12/2004 | |
| JP | 2005501597 | A | 1/2005 | |
| JP | 2005095410 | A | 4/2005 | |
| JP | 2005515825 | A | 6/2005 | |
| JP | 2006516465 | A | 7/2006 | |
| JP | 2007289707 | A | 11/2007 | |
| JP | 2007532182 | A | 11/2007 | |
| JP | 2008506447 | A | 3/2008 | |
| JP | 2011513694 | A | 4/2011 | |
| JP | 2011520248 | A | 7/2011 | |
| JP | 2011524203 | A | 9/2011 | |
| JP | 2011528963 | A | 12/2011 | |
| JP | 2012505050 | A | 3/2012 | |
| JP | 2012508042 | A | 4/2012 | |
| JP | 2015525657 | A | 9/2015 | |
| JP | 2015528327 | A | 9/2015 | |
| JP | 6029828 | B2 | 11/2016 | |
| JP | 6081510 | B2 | 2/2017 | |

(56)  References Cited

FOREIGN PATENT DOCUMENTS

| | | | |
|---|---|---|---|
| JP | 2022013922 A | 1/2022 | |
| WO | WO-1989011307 A1 | 11/1989 | |
| WO | WO-1996024297 A1 | 8/1996 | |
| WO | WO-1999000060 A1 | 1/1999 | |
| WO | WO-1999002096 A1 | 1/1999 | |
| WO | WO-2000056237 A2 | 9/2000 | |
| WO | WO-2004069072 A2 | 8/2004 | |
| WO | WO-2005099594 A1 | 10/2005 | |
| WO | WO-2005102199 A1 | 11/2005 | |
| WO | WO-2006006169 A2 | 1/2006 | |
| WO | WO-2006127158 A2 | 11/2006 | |
| WO | WO-2007088546 A2 | 8/2007 | |
| WO | WO-2007149905 A2 | 12/2007 | |
| WO | WO-2009121017 A1 | 10/2009 | |
| WO | WO-2009126544 A1 | 10/2009 | |
| WO | WO-2009136268 A1 | 11/2009 | |
| WO | WO-2009152352 A2 | 12/2009 | |
| WO | WO-2010014515 A2 | 2/2010 | |
| WO | WO-2010054048 A2 | 9/2010 | |
| WO | WO-2011006017 A1 | 1/2011 | |
| WO | WO-2011094111 A2 | 8/2011 | |
| WO | WO-2011143468 A2 | 11/2011 | |
| WO | WO-2012025833 A2 | 3/2012 | |
| WO | WO-2013059735 A1 | 4/2013 | |
| WO | WO-2014025397 A1 | 2/2014 | |
| WO | WO-2014025620 A1 | 2/2014 | |
| WO | WO-2015017499 A1 | 2/2015 | |
| WO | WO-2019099218 A1 | 5/2019 | |
| WO | WO-2023169537 A1 | 9/2023 | |
| WO | WO-2024015298 A1 * | 1/2024 | ......... A61B 17/2202 |

* cited by examiner

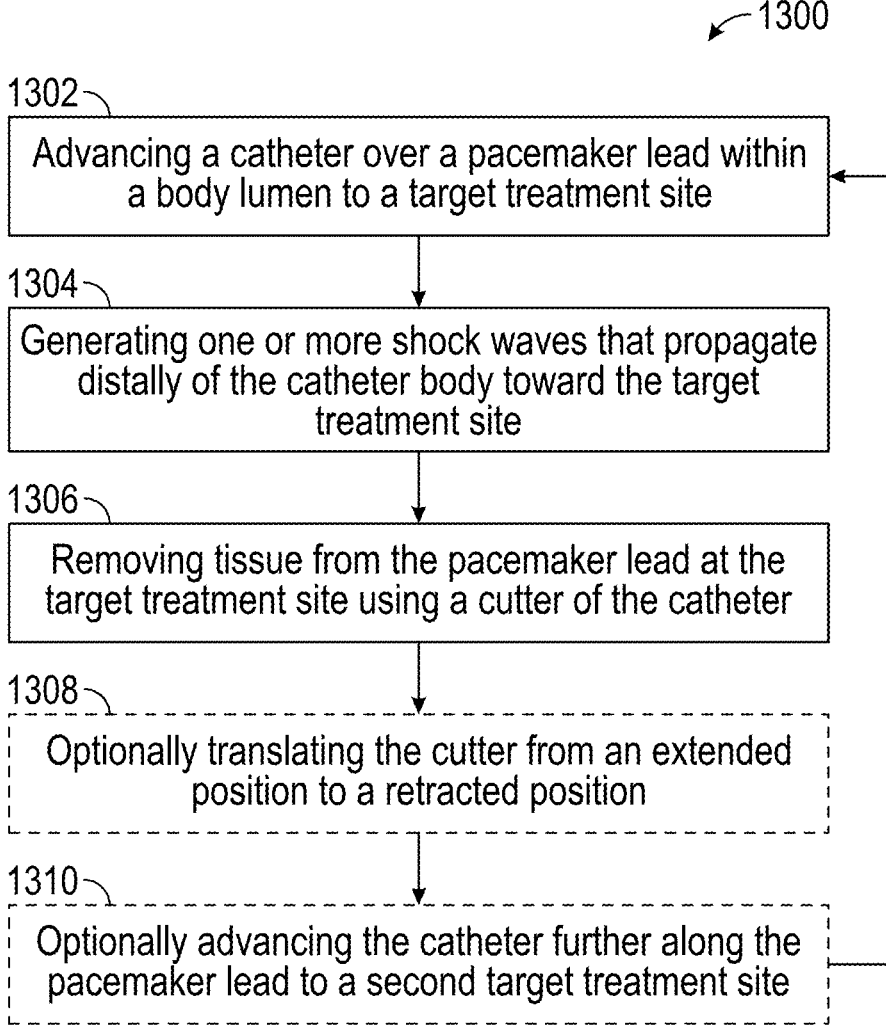

1300

1302

Advancing a catheter over a pacemaker lead within a body lumen to a target treatment site

1304

Generating one or more shock waves that propagate distally of the catheter body toward the target treatment site

1306

Removing tissue from the pacemaker lead at the target treatment site using a cutter of the catheter

1308

Optionally translating the cutter from an extended position to a retracted position

1310

Optionally advancing the catheter further along the pacemaker lead to a second target treatment site

FIG. 13

SYSTEMS, DEVICES, AND METHODS FOR TREATMENT OF TARGET MATERIAL IN A BODY LUMEN WITH SHOCK WAVES

CROSS REFERENCE TO RELATED APPLICATIONS

This application claims priority benefit of U.S. Provisional Application No. 63/604,359, filed on Nov. 30, 2023, the entire contents of which are incorporated herein by reference.

FIELD

The present disclosure relates generally to the field of medical devices and methods, and more specifically to shock wave catheter devices for treating target material in body lumens, such as calcified lesions and fibrotic tissue.

BACKGROUND

A wide variety of catheters have been developed for treating calcified lesions, such as calcified lesions in vasculature associated with arterial disease. For example, treatment systems for percutaneous coronary angioplasty or peripheral angioplasty use angioplasty balloons to dilate a calcified lesion and restore normal blood flow in a vessel. In these types of procedures, a catheter carrying a balloon is advanced into the vasculature along a guide wire until the balloon is aligned with calcified plaques. The balloon is then pressurized (normally to greater than 10 atm), causing the balloon to expand in a vessel to push calcified plaques back into the vessel wall and dilate occluded regions of vasculature.

More recently, the technique and treatment of intravascular lithotripsy (IVL) has been developed, which is an interventional procedure to modify calcified plaque in diseased arteries. The mechanism of plaque modification is through use of a catheter having one or more acoustic shock wave generating sources located within a liquid that can generate acoustic shock waves that modify the calcified plaque. IVL devices vary in design with respect to the energy source used to generate the acoustic shock waves, with two exemplary energy sources being electrohydraulic generation and laser generation.

For electrohydraulic generation of acoustic shock waves, a conductive solution (e.g., saline) may be contained within an enclosure that surrounds electrodes or can be flushed through a tube that surrounds the electrodes. The calcified plaque modification is achieved by creating acoustic shock waves within the catheter by an electrical discharge across the electrodes. The energy from this electrical discharge enters the surrounding fluid faster than the speed of sound, generating an acoustic shock wave. In addition, the energy creates one or more rapidly expanding and collapsing vapor bubbles that generate secondary shock waves. The shock waves propagate radially outward and modify calcified plaque within the blood vessels. For laser generation of acoustic shock waves, a laser pulse is transmitted into and absorbed by a fluid within the catheter. This absorption process rapidly heats and vaporizes the fluid, thereby generating the rapidly expanding and collapsing vapor bubble, as well as the acoustic shock waves that propagate outward and modify the calcified plaque. The acoustic shock wave intensity is higher if a fluid is chosen that exhibits strong absorption at the laser wavelength that is employed. These examples of IVL devices are not intended to be a comprehensive list of potential energy sources to create IVL shock waves.

The IVL process may be considered different from standard atherectomy procedures in that it cracks calcium but does not liberate the cracked calcium from the tissue. Hence, generally speaking, IVL should not require aspiration nor embolic protection. Further, due to the compliance of a normal blood vessel and non-calcified plaque, the shock waves produced by IVL do not modify the normal vessel tissue or non-calcified plaque. Moreover, IVL does not carry the same degree of risk of perforation, dissection, or other damage to vasculature as atherectomy procedures or angioplasty procedures using cutting or scoring balloons.

More specifically, catheters to deliver IVL therapy have been developed that include pairs of electrodes for electrohydraulically generating shock waves inside an angioplasty balloon. Shock wave devices can be particularly effective for treating calcified plaque lesions because the acoustic pressure from the shock waves can crack and disrupt lesions near the angioplasty balloon without harming the surrounding tissue. In these devices, the catheter is advanced over a guidewire through a patient's vasculature until it is positioned proximal to and/or aligned with a calcified plaque lesion in a body lumen. The balloon is then inflated with conductive fluid (using a relatively low pressure of 2-4 atm) so that the balloon expands to contact the lesion, but is not an inflation pressure that substantively displaces the lesion. Voltage pulses can then be applied across the electrodes of the electrode pairs to produce acoustic shock waves that propagate through the walls of the angioplasty balloon and into the lesions. Once the lesions have been cracked by the acoustic shock waves, the balloon can be expanded further to increase the cross-sectional area of the lumen and improve blood flow through the lumen. Alternative devices to deliver IVL therapy can be within a closed volume other than an angioplasty balloon, such as a cap, balloons of variable compliancy, or other enclosure.

A related issue to narrowed blood vessels resulting from calcified plaque buildup is tissue buildup around pacemaker leads and similar cardiac devices. Over time, pacemaker leads can become entrenched in fibrotic (or calcified) tissues. Such tissue buildup can make removal of pacemakers and similar devices exceedingly difficult. Techniques for efficiently modifying calcified and fibrotic tissue buildup around pacemaker leads are needed to safely remove such devices from the body.

SUMMARY

According to an aspect of the present disclosure, a catheter includes at least one shock wave emitter and a moveable shield that can be moved into a position in which it covers the at least one shock wave emitter to reflect shock waves emitted by the at least one shock wave emitter radially inwardly. The at least one shock wave emitter and the shield can be carried by a catheter body that includes a cavity at its distal end that opens in a distal direction. The reflected shock waves may propagate within the cavity to treat calcifications or fibrotic tissue drawn into or otherwise located in the cavity and/or may propagate distally out of the distal end of the cavity to treat calcifications or fibrotic tissue located distally of the catheter. The shock waves may merge with each other within the cavity, focusing energy to create a more efficacious output. The shield may be moveable to selectively uncover the at least one shock wave emitter. When uncovered, shock waves generated by the at least one shock wave emitter may travel radially outwardly to treat occlusive material located outwardly of the catheter. Thus, the catheter can treat severely occluded vessels by selectively focusing shock waves distally of the catheter and also outwardly. The catheter can additionally or alternatively facilitate the removal of pacemaker leads by selectively focusing shock waves internally and distally of the catheter to target fibrotic tissue connected to a pacemaker lead.

In some aspects, described herein are shock wave generating systems, devices, and methods that utilize a mechanical cutting mechanism (also referred to herein as a "cutter") to cut, dislodge, or otherwise remove fibrotic and/or calcified tissue at a target treatment site within a body lumen. An exemplary device may include a catheter body that includes a central lumen. At least one shock wave emitter may be disposed at a distal portion of the catheter body and configured to generate at least one shock wave that propagates distally of the catheter body. The device may include a cutting mechanism, which may be positioned, for example, within the central lumen or on an exterior of the catheter body. The cutting mechanism may be configured to be translated relative to the catheter body between a retracted position and an extended position. In the extended position, a distal end of the cutting mechanism is positioned distally of a distal end of the catheter body so that the cutting mechanism can be used to cut through the fibrous and/or calcified tissue. The cutting mechanism may be a rotatable tube, such as a flexible hypo tube that has a sharpened distal end. The cutting mechanism may be included on a moveable shield. The device may be configured to enable a user to retract the cutting mechanism (for instance, within the catheter body) for safety.

A device that includes a cutting mechanism and/or shock wave emitters can be used to dislodge or modify fibrotic tissue, for instance, including fibrotic tissue surrounding pacemaker leads in cardiac tissue. According to some aspects, systems, devices, and methods described herein may provide an effective mechanism for safely separating fibrous tissue from pacemaker leads during extraction procedures, thus making the procedures safer and more efficient. Following insertion of an exemplary device into a patient's body over the pacemaker lead and positioning of the device proximate fibrous and/or calcified tissue attached to the pacemaker lead, one or more shock wave emitters can be activated to generate one or more shock waves, loosening the fibrotic and/or calcified tissue from the pacemaker lead. Optionally, a cutting mechanism of the device can be extended from a distal end of the device to cut away the fibrous and/or calcified tissue, facilitating the easy removal of the lead from the patient's body.

According to an aspect, a catheter includes a catheter body comprising a cavity at a distal end of the catheter body; at least one shock wave emitter positioned outwardly of the cavity and configured to generate at least one shock wave; and a shield surrounding the catheter body and covering the at least one shock wave emitter such that shock waves generated by the at least one shock wave emitter are reflected by the shield into the cavity at the distal end of the catheter body.

The shield may be translatable along the catheter body. The shield may be positionable so that the distal end of the shield does not cover the at least one shock wave emitter.

The catheter body may further include a central lumen configured to receive at least one of a guidewire and a pacemaker lead. The central lumen may have a smaller diameter than the cavity at the distal end of the catheter body.

The cavity may be sized to receive a distal portion of a pacemaker lead. The catheter body may include an annular space configured to be fillable with a conductive fluid, wherein the at least one shock wave emitter is positioned inside the annular space.

The shield may include a tapered distal end. The at least one shock wave emitter may include a plurality of shock wave emitters, wherein the shield is positionable with respect to the catheter body such that the tapered distal end of the shield covers at least one but not all of the plurality of shock wave emitters. The tapered distal end may be configured to be extended distally of the distal end of the catheter body for piercing tissue.

The at least one shock wave emitter may include an emitter band. The emitter band may form a plurality of shock wave emitters. The at least one shock wave emitter may include a plurality of shock wave emitters formed by a plurality of emitter bands, wherein each emitter band forms multiple of the shock wave emitters. The at least one shock wave emitter may include a radially firing shock wave emitter.

The catheter may include at least one forward firing shock wave emitter positioned at the distal end of the catheter body distally of the at least one shock wave emitter and configured to generate at least one forward propagating shock wave. The at least one shock wave emitter and the at least one forward firing shock wave emitter may be configured to generate shock waves independently.

According to an aspect, a system includes any of the catheters described above and a shock wave power source for providing energy to the at least one shock wave emitter for generating the at least one shock wave. The shock wave power source may be configured for generating voltage pulses. The shock wave power source may be configured for generating laser pulses.

According to an aspect, a method for treating a target material in a body lumen with shock waves includes generating at least one shock wave from at least one shock wave emitter of a catheter; and reflecting the at least one shock wave with a shield of the catheter such that the at least one shock wave is directed radially inwardly into a cavity of the catheter to treat target material located at least partially within the cavity and/or distally of the cavity.

The method may further include translating the shield proximally to uncover the at least one shock wave emitter of the catheter; and generating at least one additional shock wave from the at least one shock wave emitter, wherein the at least one shock wave is emitted radially outwardly to treat target material located outwardly of the catheter.

The method may further include covering a first shock wave emitter located at a first side of the catheter by a tapered distal end of the shield while leaving a second shock wave emitter located at a second side of the catheter uncovered by the shield; and generating additional shock waves from the first and second shock wave emitters, wherein shock waves generated by the first shock wave emitter are reflected by the tapered distal end and propagate radially outwardly from the second side of the catheter along with shock waves generated by the second shock wave emitter. The at least one shock wave emitter may include a radially firing shock wave emitter.

According to an aspect, a method for removing a pacemaker lead includes advancing a catheter along the pacemaker lead to a target site comprising fibrotic tissue; positioning the catheter such that at least a portion of the fibrotic tissue is located at least partially within a cavity at a distal end of the catheter; generating at least one shock wave from at least one shock wave emitter of the catheter; and reflecting the at least one shock wave with a shield of the catheter such that the at least one shock wave is directed radially inwardly into the cavity of the catheter to break up the at least a portion of the fibrotic tissue located at least partially in the cavity. The method may include generating at least one shock wave by at least one forward firing shock wave emitter of the catheter to break up fibrotic tissue located in front of a distal end of the catheter.

According to an aspect, a catheter includes a catheter body comprising a cavity at a distal end of the catheter body; and at least one shock wave emitter positioned outwardly of the cavity and configured to generate at least one shock wave that propagates into the cavity at the distal end of the catheter body to treat target material disposed within the cavity and/or at a distal end of the cavity.

The catheter may include a central lumen configured to receive at least one of a guidewire and a pacemaker lead. The central lumen may have a smaller diameter than the cavity at the distal end of the catheter body.

The cavity may be sized to receive a distal portion of a pacemaker lead. The catheter body may include an annular space configured to be fillable with a conductive fluid, wherein the at least one shock wave emitter is positioned inside the annular space. The at least one shock wave emitter may include an emitter band. The emitter band may form a plurality of shock wave emitters.

The at least one shock wave emitter may include a plurality of shock wave emitters formed by a plurality of emitter bands, wherein each emitter band forms multiple of the shock wave emitters. The catheter may include at least one forward firing shock wave emitter positioned at the distal end of the catheter body distally of the at least one shock wave emitter and configured to generate at least one forward propagating shock wave. The at least one shock wave emitter and the at least one forward firing shock wave emitter may be configured to generate shock waves independently. The at least one shock wave emitter may include a radially firing shock wave emitter.

According to an aspect, a catheter includes a catheter body; at least one shock wave emitter disposed on the catheter body; and a shield extending at least partially around the catheter body and covering the at least one shock wave emitter such that shock waves generated by the at least one shock wave emitter are reflected by the shield.

The shield may be translatable along the catheter body. The shield may be positionable so that the distal end of the shield does not cover the at least one shock wave emitter. The catheter body may be further include a central lumen configured to receive at least one of a guidewire and a pacemaker lead. The catheter body may include an annular space configured to be fillable with a conductive fluid, wherein the at least one shock wave emitter is positioned inside the annular space.

The shield may include a tapered distal end. The at least one shock wave emitter may include a plurality of shock wave emitters, wherein the shield is positionable with respect to the catheter body such that the tapered distal end of the shield covers at least one but not all of the plurality of shock wave emitters. The tapered distal end may be configured to be extended distally of the distal end of the catheter body for piercing tissue.

The at least one shock wave emitter may include an emitter band. The emitter band may form a plurality of shock wave emitters. The at least one shock wave emitter may include a plurality of shock wave emitters formed by a plurality of emitter bands, wherein each emitter band forms multiple of the shock wave emitters.

The catheter may include at least one forward firing shock wave emitter positioned at the distal end of the catheter body distally of the at least one shock wave emitter and configured to generate at least one forward propagating shock wave. The at least one shock wave emitter and the at least one forward firing shock wave emitter may be configured to generate shock waves independently. The at least one shock wave emitter may include a radially firing shock wave emitter.

According to an aspect, a catheter includes a catheter body; at least one shock wave emitter disposed on the catheter body; and a moveable shield extending at least partially around the catheter body and configured for translating along the catheter body.

The shield may be positionable so that the shield covers the at least one shock wave emitter. The shield may be positionable so that a distal end of the shield does not cover the at least one shock wave emitter.

The catheter body may further include a central lumen configured to receive at least one of a guidewire and a pacemaker lead. The catheter body may include an annular space configured to be fillable with a conductive fluid, wherein the at least one shock wave emitter is positioned inside the annular space.

The shield may include a tapered distal end. The at least one shock wave emitter may include a plurality of shock wave emitters, wherein the shield is positionable with respect to the catheter body such that the tapered distal end of the shield covers at least one but not all of the plurality of shock wave emitters. The tapered distal end may be configured to be extended distally of the distal end of the catheter body for piercing tissue.

The at least one shock wave emitter may include an emitter band. The emitter band may include a plurality of shock wave emitters.

The at least one shock wave emitter may include a plurality of shock wave emitters formed by a plurality of emitter bands, wherein each emitter band forms multiple of the shock wave emitters. The catheter may include at least one forward firing shock wave emitter positioned at the distal end of the catheter body distally of the at least one shock wave emitter and configured to generate at least one forward propagating shock wave. The at least one shock wave emitter and the at least one forward firing shock wave emitter may be configured to generate shock waves independently. The at least one shock wave emitter may include a radially firing shock wave emitter.

According to an aspect, a catheter for use in a body lumen comprises: a catheter body comprising a central lumen; at least one shock wave emitter disposed at a distal portion of the catheter body and configured to generate at least one shock wave that propagates distally of the catheter body; and a rotatable cutting mechanism configured to be translated relative to the catheter body to an extended position in which a distal end of the rotatable cutting mechanism is distal of a distal end of the catheter body for cutting tissue located distally of the distal end of the catheter body.

Optionally, the rotatable cutting mechanism is configured to be retracted so that a distal end of the rotatable tube is proximal of the distal end of the catheter body. Optionally, the rotatable cutting mechanism comprises a tube having a distal end configured for cutting the tissue. Optionally, the distal end comprises at least one of a beveled end, a serrated end, a scalloped end, and a double beveled end. Optionally, the rotatable tube is configured to extend up to 10 millimeters beyond a distal most surface of the catheter body. Optionally, the catheter body comprises a nozzle and a distal end of the nozzle comprises the distal-most surface of the catheter body. Optionally, the nozzle is configured to concentrate the at least one shock wave generated by the at least one shock wave emitter at the outlet of the nozzle. Optionally, the nozzle is configured to concentrate at least one bubble resulting from the at least one shock wave to the outlet of the nozzle. Optionally, the rotatable cutting mechanism comprises a lumen configured to receive a pacemaker lead. Optionally, the rotatable cutting mechanism is operatively connected to a user-engageable sliding component configured to enable a user to translate the rotatable tube relative to the catheter body. Optionally, the rotatable cutting mechanism is biased toward the retracted position. Optionally, the rotatable cutting mechanism is operatively connected to a user-engageable rotational component to enable a user to rotate the rotatable cutting mechanism. Optionally, the rotatable cutting mechanism is rotatably driven by a motor. Optionally, the motor is battery powered. Optionally, the motor is positioned within a handle of the catheter. Optionally, the handle comprises one or more user engagements for activating the motor. Optionally, activation of a first user engagement of the one or more user engagements causes the rotatable cutting mechanism to rotate in a first direction and activation of a second user engagement of the one or more user engagements causes the rotatable cutting mechanism to rotate in a second direction. Optionally, the at least one shock wave emitter is positioned radially outward of the rotatable cutting mechanism. Optionally, the at least one shock wave emitter comprises a pair of electrodes. Optionally, the at least one shock wave emitter comprises an optical fiber configured to emit a laser pulse into a conductive fluid at a distal end of the optical fiber. Optionally, the at least one shock wave emitter comprises multiple shock wave emitters connected in series.

According to an aspect, a method for removing a pacemaker lead comprising: advancing a catheter over a pacemaker lead within a body lumen to a target treatment site; generating one or more shock waves that propagate distally of the catheter body toward the target treatment site; and removing tissue from the pacemaker lead at the target treatment site using a cutting mechanism of the catheter. Optionally, the method includes translating the cutting mechanism from an extended position to a retracted position; advancing the catheter further along the pacemaker lead to a second target treatment site; and generating one or more additional shock waves. Optionally, the target treatment site is within the heart.

According to an aspect, a system for treating a lesion in a body lumen comprises: a shock wave energy generator; and any of the catheters described herein. Optionally, the shock wave energy generator is configured to deliver high voltage pulses to a shock wave emitter of the plurality of shock wave emitters. Optionally, the high voltage pulses are between 3 kV and 30 kV. Optionally, the shock wave energy generator applies an alternating current to the electrodes to induce a change in the polarity of the electrodes. Optionally, the shock wave energy generator comprises a laser pulse generator.

In some embodiments, any one or more of the characteristics of any one or more of the systems and methods recited above may be combined, in whole or in part, with one another and/or with any other features or characteristics described elsewhere herein.

BRIEF DESCRIPTION OF THE FIGURES

The invention will now be described, by way of example only, with reference to the accompanying drawings, in which:

FIG. 13 illustrates an exemplary method for removing tissue from the pacemaker lead at the target treatment site using a cutting mechanism of a catheter according to some examples.

DETAILED DESCRIPTION

Figure 1:
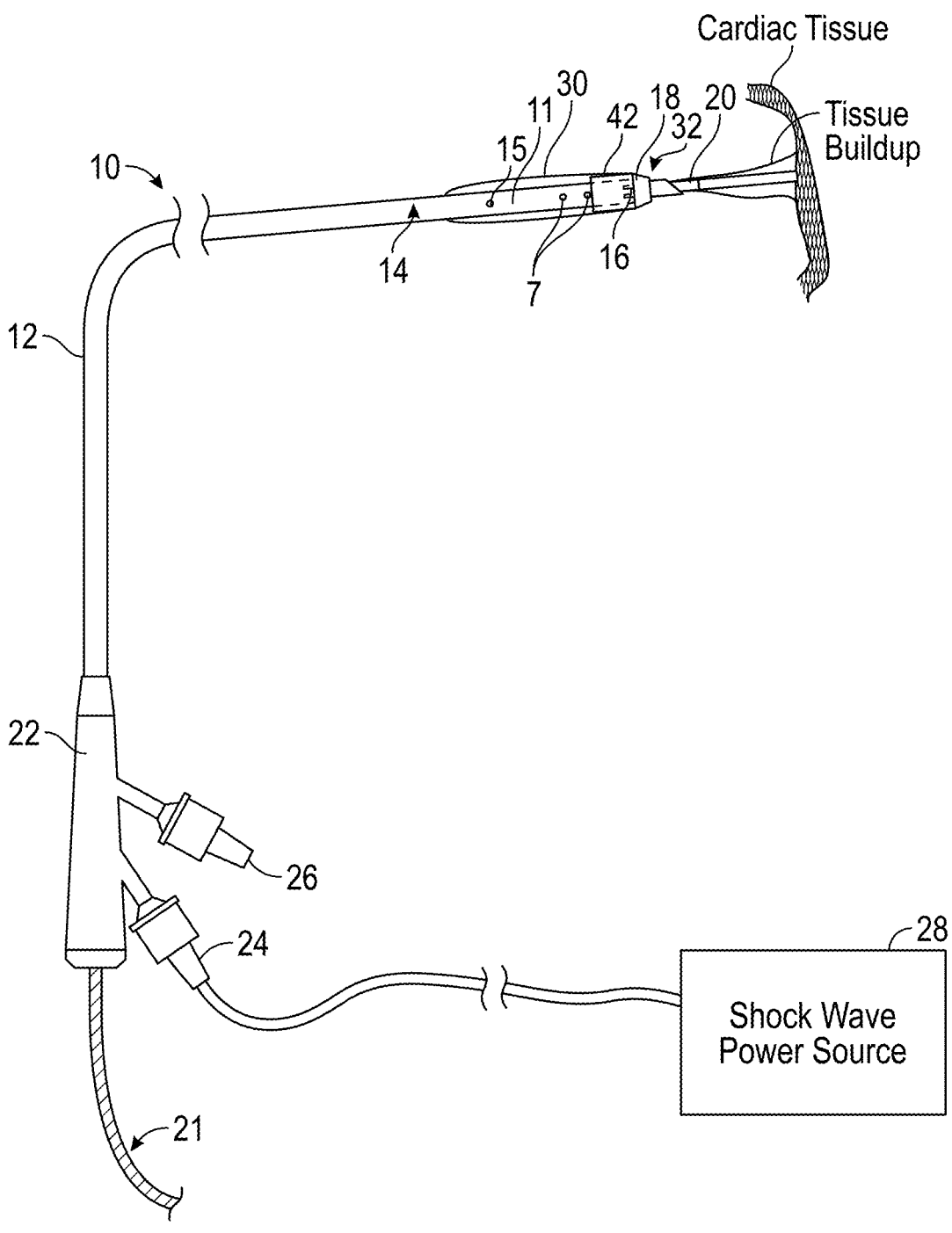
FIG. 1 illustrates an exemplary system for treating lesions in body lumens, according to one or more aspects of the present disclosure.

The following description is presented to enable a person of ordinary skill in the art to make and use the various embodiments and aspects thereof disclosed herein. Descriptions of specific devices, assemblies, techniques, and applications are provided only as examples. Various modifications to the examples described herein will be readily apparent to those of ordinary skill in the art, and the general principles described herein may be applied to other examples and applications without departing from the spirit and scope of the various embodiments and aspects thereof. Thus, the various embodiments and aspects thereof are not intended to be limited to the examples described herein and shown but are to be accorded the scope consistent with the claims.

Described herein are examples of systems, devices, and methods for treating target material (e.g., calcifications and/or fibrotic tissue) in body lumen of a patient with shock waves, mechanical cutting, or both. Shock waves may be directed radially inwardly to a cavity in a distal end of a catheter, enabling the breaking up, softening, and/or weakening of target material, such as calcified stenotic lesions and/or fibrotic tissue covering a pacemaker lead. Catheters may be configured direct shock waves at target material in multiple different directions, including in a distal direction, forward of the catheter, in an outward radial direction, and in an inward radial direction, enabling the treatment of target material in a variety of different ways. The devices, systems, and methods described herein may employ a catheter device configured with both shock wave emitters to loosen or break up fibrotic and/or calcified tissue and a cutting mechanism for cutting through fibrotic and/or calcified tissue that may be difficult to modify using shock waves alone.

According to an aspect, a shock wave catheter can include a catheter body that has a cavity at the distal end. The catheter can be moved into engagement with a vascular occlusion or fibrotic tissue such that the vascular occlusion or fibrotic tissue cavity is at least partially encapsulated by the cavity. The catheter can include one or more radially firing shock wave emitters positioned outward of the cavity and configured to emit shock waves radially outwardly. The catheter may include a shield that can cover the radially firing shock wave emitters. The shield can be made of a material that reflects shock waves such that shock waves generated by the radially firing shock wave emitters are reflected radially inwardly into the cavity when covered by the shield. The pressure generated by the shock waves can be amplified within the cavity through constructive interference of the reflected shock waves. This enables the catheter to break up or soften calcifications or fibrotic tissue positioned within the cavity.

The shield may be a moveable shield that can be translated proximally to uncover one or more of the radially firing shock wave emitters. When the radially firing shock wave emitters are uncovered by the shield, the shock waves generated by the radially firing shock wave emitters can propagate radially outwardly. The translatability of the shield enables the selective use of the catheter for directing shock waves radially outwardly and inwardly for targeted treatment of vascular occlusions and/or fibrotic tissue located outwardly of the catheter and located within the cavity of the catheter body.

The catheter may include one or more forward firing shock wave emitters positioned distally of the one or more radially firing shock wave emitters. The one or more forward firing shock wave emitters are configured to generate shock waves that propagate distally from the catheter, thereby improving the catheter's ability to break up occlusions located distal of the catheter. This may enable the catheter to generate shock waves in both a radial direction and a forward direction, enhancing the ability of the catheter to break calcifications in a patient's vasculature or fibrotic tissue coating a pacemaker lead.

In some aspects, an exemplary catheter includes a catheter body, a cutting mechanism, and at least one shock wave emitter disposed at a distal portion of the catheter. For instance, the shield may include a tapered distal tip. The tapered distal tip may be configured to cut into tissue. The shield may be translated distally such that the tapered distal tip extends distally of the distal end of the catheter body, enabling the tapered distal tip to cut into tissue positioned distally of the distal end of the catheter body. The tapered distal tip may be used, additionally or alternatively, to focus shock waves in a particular lateral direction. The tapered distal tip can be moved to cover one or more radially firing shock wave emitters on one side of the catheter body, while leaving uncovered one or more other radially firing shock wave emitters on the opposite side of the catheter body. The tapered distal tip reflects shock waves generated by the one or more covered shock wave emitters, directing those shock waves toward the uncovered side. The reflected shock waves may constructively interfere with the shock waves generated by the uncovered shock wave emitter(s), amplifying the pressure in a particular lateral direction. The shield may be at least partially radiopaque so that a user can determine which direction the shock waves will be directed.

In some aspects, a central lumen may extend along the length of the catheter body from a proximal end of the body to a distal end of the body. The cutting mechanism may be positioned within the central lumen and translatable relative to the catheter body between extended and retracted positions. In the extended position, a distal end of the cutting mechanism is distal of a distal end of the catheter body, and in the retracted position, the distal end of the cutting mechanism is proximal of the distal end of the catheter body. Accordingly, in the extended position, the cutting mechanism can be used to cut through fibrous tissue distal of the catheter, and in the retracted position, the catheter can be safely navigated within the body lumen without piercing or cutting the lumen, or otherwise harming the patient or physician.

The cutting mechanism may extend along the central lumen of the catheter body and into a handle at a proximal end of the catheter. The handle may include one or more engagements for operating the cutting mechanism. For example, the handle may include one or more engagements for translating the rotatable tube between the extended and retracted positions. The handle may include one or more engagements for rotationally operating the cutting mechanism for cutting tissue. One or more of the engagements may be configured for manual translation and/or rotation of the cutting mechanism and/or for powered rotation and/or translation of the cutting mechanism. The cutting mechanism may include a rotatable tube that includes one or more cutting features at its distal end for modifying (e.g., cutting or tearing) tissue such as fibrotic and calcified tissue. The rotatable tube may include a lumen for receiving a wire.

The cutting mechanism and the shock wave emitters can be selectively used to cut, break apart, or otherwise modify calcifications and fibrotic tissue buildup in a body lumen. The catheter may be advanced within a body lumen to a treatment site, for instance, using a guidewire or lead extending through a lumen of the cutting mechanism. Once positioned at the target treatment side, the catheter may be used to generate one or more shock waves. The shock waves may be directed at least partially in a distal direction such that the shock waves propagate distally of the catheter body to the target treatment site to fracture calcifications and/or fibrous tissue with shock waves. When necessary, the cutting mechanism can be extended to its extended position and operated to mechanically cut, tear, or otherwise disrupt tissue. The shock wave emitters and cutting mechanism can be used in any order or one without the other. For example, the cutting mechanism can be used after the shock wave emitters to disrupt tissue that was not broken apart by the shock waves or can be used prior to the shock wave emitters to modify tissue prior to shock wave treatment.

One use for IVL catheters is facilitating the removal of pacemaker leads from a body lumen by loosening fibrous and calcified tissue surrounding the lead. Over time, as pacemaker leads are left in the body, fibrous and calcified tissue builds up, encapsulating the pacemaker leads in the body. Existing lead extraction devices and procedures pose potential risks of causing damage to the heart or vessels and sometimes may require the use of multiple devices, such as both laser and rotational cutting devices, which complicates removal procedures creating greater risk of harm to the patient. The catheters described herein enable more efficient pacemaker lead removal by combining shock wave emitters and a mechanical cutting mechanism in a single device.

In some examples, positioning the catheters disclosed herein at the target treatment site may include receiving a portion of a pacemaker lead into the catheter or positioning the distal end of a catheter immediately adjacent to the pacemaker lead. As discussed above, pacemaker leads can become encapsulated in fibrotic and/or calcified tissue. Shock waves generated using the at least one shock wave emitter can loosen or break up the tissue stuck to the lead. The remaining tissue can be removed from the pacemaker lead at the target treatment site using the cutting mechanism of the catheter. The cutting mechanism (which may include or be the rotatable tube) may be extended distally of the distal end of the catheter and the pacemaker lead may be received into the tube. The cutting mechanism may then be rotated such that its distal end cuts away tissue stuck to the lead.

Efforts have been made to improve the design of electrode assemblies included in shock wave and directed cavitation catheters. For instance, low-profile electrode assemblies have been developed that reduce the crossing profile of a catheter and allow the catheter to more easily navigate calcified vessels to deliver shock waves in more severely occluded regions of vasculature. Examples of low-profile electrode designs that can be used for the catheters described herein can be found in U.S. Pat. Nos. 8,888,788, 9,433,428, and 10,709,462, and in U.S. Publication No. 2021/0085383 all of which are incorporated herein by reference. Other catheter designs have improved the delivery of shock waves, for instance, by specific electrode construction and configuration thereby directing shock waves in a forward direction to break up tighter and harder-to-cross occlusions in vasculature. Examples of forward-firing catheter designs, which can be used for the catheters described herein, can be found in U.S. Pat. Nos. 10,966,737, 11,478,261, and 11,596,423 and U.S. Publication Nos. 2023/0107690 and 2023/0165598, all of which are incorporated herein by reference.

As used herein, the term "electrode" refers to an electrically conducting element (typically made of metal) that receives electrical current and subsequently releases the electrical current to another electrically conducting element. In the context of the present disclosure, electrodes are often positioned relative to each other, such as in an arrangement of an inner electrode and an outer electrode. Accordingly, as used herein, the term "electrode pair" refers to two electrodes that are positioned adjacent to each other such that application of a sufficiently high voltage to the electrode pair will cause an electrical current to transmit across the gap (also referred to as a "spark gap") between the two electrodes (e.g., from an inner electrode to an outer electrode, or vice versa, optionally with the electricity passing through a conductive fluid or gas therebetween). In some contexts, one or more electrode pairs may also be referred to as an electrode assembly. In the context of the present disclosure, the term "emitter" broadly refers to the region of an electrode assembly where the current transmits across the electrode pair, generating a shock wave. The terms "emitter sheath" and "emitter band" refers to a continuous or discontinuous band of conductive material that may form one or more electrodes of one or more electrode pairs, thereby forming a location of one or more emitters.

Components of emitters, including electrodes and emitter sheaths/bands, may be formed from a metal, such as stainless steel, copper, tungsten, platinum, palladium, molybdenum, cobalt, chromium, iridium, an alloy or alloys thereof, such as cobalt-chromium, platinum-chromium, cobalt-chromium-platinum-palladium-iridium, or platinum-iridium, or a mixture of such materials.

For treatment of an occlusion in a blood vessel, the voltage pulse applied by a power source, including any of the power sources described herein (which may also be referred to herein as voltage sources or pulse generators), is typically in the range of from about five hundred to three thousand volts (500 V-3,000 V). In some implementations, the voltage pulse applied by the voltage source can be up to about ten thousand volts (10,000 V) or higher than ten thousand volts (10,000 V). The pulse width of the applied voltage pulses ranges between two microseconds and six microseconds (2-6 µs). The repetition rate or frequency of the applied voltage pulses may be between about 1 Hz and 10 Hz. The total number of pulses applied by the power source may be, for example, sixty (60) pulses, eighty (80) pulses, one hundred twenty (120) pulses, three hundred (300) pulses, or up to five hundred (500) pulses, or any increments of pulses within this range. Alternatively, or additionally, in some examples, the power source may be configured to deliver a packet of micro-pulses having a sub-frequency between about 100 Hz-10 kHz. The preferred voltage, repetition rate, and number of pulses may vary depending on, e.g., the size of the lesion, the extent of calcification, the size of the blood vessel, the attributes of the patient, or the stage of treatment. For instance, a physician may start with low energy shock waves and increase the energy as needed during the procedure, or vice versa. The magnitude of the shock waves can be controlled by controlling the voltage, current, duration, and repetition rate of the pulsed voltage from the power source.

In some embodiments, an IVL catheter is a so-called "rapid exchange-type" ("Rx") catheter provided with an opening portion through which a guide wire is guided (e.g., through a middle portion of a central tube in a longitudinal direction). In other embodiments, an IVL catheter may be an "over-the-wire-type" ("OTW") catheter in which a guide wire lumen is formed throughout the overall length of the catheter, and a guide wire is guided through the proximal end of a hub.

Although shock wave devices described herein generate shock waves based on high voltage applied to electrodes, it should be understood that a shock wave device additionally or alternatively may comprise a laser and optical fibers as a shock wave emitter system whereby the laser source delivers energy through an optical fiber and into a fluid to form shock waves and/or cavitation bubbles.

In the following description of the various embodiments, reference is made to the accompanying drawings, in which are shown, by way of illustration, specific embodiments that can be practiced. It is to be understood that other embodiments and examples can be practiced, and changes can be made without departing from the scope of the disclosure.

Certain aspects of the present disclosure include process steps and instructions described herein in the form of an algorithm. It should be noted that the process steps and instructions of the present disclosure could be embodied in software, firmware, or hardware and, when embodied in software, could be downloaded to reside on and be operated from different platforms used by a variety of operating systems. Unless specifically stated otherwise as apparent from the following discussion, it is appreciated that, throughout the description, discussions utilizing terms such as "processing," "computing," "calculating," "determining," "displaying," "generating" or the like, refer to the action and processes of a computer system, or similar electronic computing device, that manipulates and transforms data represented as physical (electronic) quantities within the computer system memories or registers or other such information storage, transmission, or display devices.

The present disclosure in some embodiments also relates to a device for performing the operations herein. This device may be specially constructed for the required purposes, or it may comprise a general-purpose computer selectively activated or reconfigured by a computer program stored in the computer. Such a computer program may be stored in a non-transitory, computer readable storage medium, such as, but not limited to, any type of disk, including floppy disks, USB flash drives, external hard drives, optical disks, CD-ROMs, magnetic-optical disks, read-only memories (ROMs), random access memories (RAMs), EPROMS, EEPROMs, magnetic or optical cards, application specific integrated circuits (ASICs), or any type of media suitable for storing electronic instructions, and each connected to a computer system bus. Furthermore, the computing systems referred to in the specification may include a single processor or may be architectures employing multiple processor designs, such as for performing different functions or for increased computing capability. Suitable processors include central processing units (CPUs), graphical processing units (GPUs), field programmable gate arrays (FPGAs), and ASICs.

The methods, devices, and systems described herein are not inherently related to any particular computer or other apparatus. Various general-purpose systems may also be used with programs in accordance with the teachings herein, or it may prove convenient to construct a more specialized apparatus to perform the required method steps. The structure for a variety of these systems will appear from the description below. In addition, the present invention is not described with reference to any particular programming language. It will be appreciated that a variety of programming languages may be used to implement the teachings of the present disclosure as described herein.

In addition, it is also to be understood that the singular forms "a," "an," and "the" used in the following description are intended to include the plural forms as well, unless the context clearly indicates otherwise. It is also to be understood that the term "and/or" as used herein refers to and encompasses any and all possible combinations of one or more of the associated listed items. It is further to be understood that the terms "includes, "including," "comprises," and/or "comprising," when used herein, specify the presence of stated features, integers, steps, operations, elements, components, and/or units but do not preclude the presence or addition of one or more other features, integers, steps, operations, elements, components, units, and/or groups thereof. As provided herein, it should be appreciated that any disclosure of a numerical range describing dimensions or measurements such as thicknesses, length, weight, time, frequency, temperature, voltage, current, angle, etc. is inclusive of any numerical increment or gradation within the ranges set forth relative to the given dimension or measurement. Furthermore, numerical designators such as "first", "second", "third", "fourth", etc. are merely descriptive and do not indicate a relative order, location, or identity of elements or features described by the designators. For instance, a "first" shock wave may be immediately succeeded by a "third" shock wave, which is then succeeded by a "second" shock wave. As another example, a "third" emitter may be used to generate a "first" shock wave and vice versa. Accordingly, numerical designators of various elements and features are not intended to limit the disclosure and may be modified and interchanged without departing from the subject invention.

FIG. 1 illustrates a system for treating calcifications in body lumens. The system includes a shock wave generating catheter 10. The catheter 10 may generate shock waves to fragment, crack, or otherwise break up calculi within a body lumen, for instance, to treat various occlusions within blood vessels. The catheter 10 includes at its distal end at least one shock wave emitter 16. Cather 10 may include at least one shock wave emitter 15 positioned proximally of the at least one shock wave emitter 16. The at least one shock wave emitter 16 may be configured to generate shock waves that propagate primarily distally of catheter 10 and the at least one shock wave emitter 15 may be configured to generate shock waves that propagate primarily radially outward of catheter 10.

The at least one shock wave emitter 16 may include an electrode pair having first and second electrodes separated by a gap, at which shock waves are formed when a current flows across the gap between the electrodes of the pair (i.e., when a voltage is applied across the first and second electrodes). The electrode pairs described herein may be formed by an emitter band and one or more electrodes positioned adjacent to the emitter band, between adjacent exposed portions of two conductive wires, or otherwise by two conductive elements positioned adjacent to one another separated by a spark gap. In some variations, the at least one shock wave emitter 16 includes a laser pulse emitter, such as a distal end of an optical fiber, for emitting laser pulses that generate shock waves.

The catheter 10 may be advanced to a lesion in a patient's vasculature, such as the fibrotic buildup on the pacemaker lead 20 depicted in FIG. 1 and voltage pulses are applied to the at least one shock wave emitter 16, to generate shock waves that propagate into fibrotic tissue or other lesions proximate the distal end of catheter 10. The catheter 10 may be advanced over the pacemaker lead 20 along at least a portion of the vasculature. In some examples, a guidewire 21, side saddle, guide catheter or guide sheath, or micro guidewire may be used and the catheter 10 may be advanced over or within the guidewire 21, side saddle, guide catheter or guide sheath, or micro guidewire along at least a portion of the vasculature.

The catheter 10 may additionally include at its distal end one or more cutting mechanisms 32. The one or more cutting mechanisms 32 may be configured to be translated relative to the catheter body 11 to an extended position. In the extended position, a distal end of the cutting mechanism 32 may be distal of a distal end the catheter body 11 or otherwise positioned distally of any other portion of the catheter 10 such that the distal end of the cutting mechanism 32 forms the distal most portion of the catheter 10 when extended. The one or more cutting mechanisms 32 may include one or more cutting features at its distal end (e.g., any of a beveled edge, a serrated edge, a scalloped edge, and/or a double beveled edge) such that in the extended position, the one or more cutting mechanisms 32 can be used to cut calcified and/or fibrotic tissue in front of the catheter 10, for instance to remove the calcified and/or fibrotic tissue from a pacemaker lead. The one or more cutting mechanisms 32 may also be configured to be retracted so that the distal end of the one or more cutting mechanisms 32 is proximal of the distal most surface 46 of the catheter body 11 to enable navigation of the catheter within a body lumen without cutting or piercing the lumen. In some examples, the cutting mechanism 32 is biased toward a retracted position.

The catheter 10 may include a shock wave energy concentrator 42 at the distal end of the catheter body 11. The shock wave energy concentrator 42 may be a shield that covers one or more shock wave emitters 16 for reflecting shock waves generated by the emitters 16 inwardly and/or in a forward direction. The shock wave energy concentrator 42 may be configured such that at least one shock wave and/or bubble generated by the at least one shock wave emitter 16 propagates within shock wave energy concentrator 42 and is concentrated at an outlet of the shock wave energy concentrator and directed distally of the catheter 10. The shock wave energy concentrator 42 may be a nozzle may be formed from an acoustically reflective material such that shock waves and/or bubbles directed into the shock wave energy concentrator are reflected by the shock wave energy concentrator wall 18. The shock waves may continue to propagate forward (e.g., distally) within the shock wave energy concentrator 42 as they reflect from walls 18 of the shock wave energy concentrator 42, optionally reaching a peak concentration at an outlet of the shock wave energy concentrator 42 before propagating distally of the catheter through the nozzle outlet. The shock waves propagating within the shock wave energy concentrator may cause a fluid within the shock wave energy concentrator to move toward the outlet, increasing in pressure and velocity as it propagates within the shock wave energy concentrator toward the outlet. The fluid may exit via the outlet and project forward toward a target treatment area. In some examples a distal end of the shock wave energy concentrator 42 forms at least one of the one or more cutting mechanisms 32. The distal end of the shock wave energy concentrator 42 may be extendable such that its distal end is positioned distally of the catheter body 11 and may be retractable such that its distal end is positioned proximally of the distal end of catheter body 11.

In some examples, an enclosure 30 (e.g., a low-profile flexible angioplasty balloon, a polymer membrane in tension that can flex outward, etc.) may optionally be sealably attached to the catheter 10, forming a channel around the shaft 12 of the catheter. The enclosure 30 may surround one or more shock wave emitters 15, such that the shock waves are produced in a closed system within the enclosure 30. The enclosure 30 may be attached such that the outlet of the shock wave energy concentrator 42 remains open. The cutting mechanism 32 may thus be extended into the body lumen via the open outlet of shock wave energy concentrator 42. As noted, in some examples the cutting mechanism 32 is the distal end of shock wave energy concentrator 42. The enclosure 30 may be filled or inflated with a conductive fluid, such as saline. The enclosure 30 can alternatively be referred to as a "window," in particular for implementations when the interior volume is filled with a fluid and pressurized, the window maintains a substantively constant volume and profile. The conductive fluid allows the shock waves to outward from the electrode pair(s) of the shock wave emitter(s) 15 through the walls of the enclosure 30 and then into a target lesion. In one or more examples, the conductive fluid may also contain x-ray contrast fluid to permit fluoroscopic viewing of the catheter 10 during use. In some implementations, the material that forms the primary surface(s) of the enclosure 30 through which shock waves pass can be a noncompliant polymer. In other implementations, a rigid and inflexible structure may be used in lieu of enclosure 30. The enclosure 30 may mitigate thermal injury to soft tissue and reduce cavitation stresses by limiting expansion of the vapor bubbles produced during shock wave generation to the interior of the enclosure. For instance, the vapor bubbles hit the enclosure wall before reaching their maximum potential size, thus inducing collapse, and reducing cavitation stress and preventing soft tissue injury that can be caused by tensile stresses during cavitation bubble collapse.

The catheter 10 includes a proximal end 22 (or handle) that remains outside of a patient's vasculature during treatment. The proximal end 22 includes an entry port for receiving the guidewire 21. The proximal end 22 also includes at least one fluid port 26. The at least one fluid port 26 may include a fluid port configured to receive a conductive fluid for filling and/or emptying the enclosure 30 during treatment. A fluid port may of the at least one fluid port 26 may be configured to receive a fluid for replacing fluid that exits the shock wave energy concentrator 42 during shock wave generation. A fluid supply line connected to the at least one fluid port 26 may be configured to supply a fluid (e.g., saline or other conductive fluid) to an inlet of the shock wave energy concentrator 42 to replace fluid that exits the outlet of the nozzle when the respective shock waves are generated by the one or more shock wave emitters. Debris from shock wave generation (e.g., fragmented calcified tissue and/or fibrous tissue) may collect in the shock wave energy concentrator 42 and vasculature following shock wave generation. A fluid return line connected to the at least one fluid port 26 may be configured to remove debris from the body lumen received via the outlet of the shock wave energy concentrator 42. The proximal end 22 may also include user engagements connected to components configured for rotating and/or translating the one or more cutting mechanisms 32.

In some examples, one or more sensors 7 are positioned along the catheter 10. The sensors 7 may be positioned at any location on catheter 10. For instance, the sensors 10 may be positioned proximal to one or more shock wave emitters 16, distal of one or more shock wave emitters 16, and/or intermediary between one or more shock wave emitters 16

(or any combination thereof). The sensors 7 may be positioned external to the enclosure 30 and/or outside of a patient. For instance, certain sensors, such as a pressure sensor, may be positioned outside of the enclosure 30 and/or outside of the patient. The sensors may include one or more of any suitable sensor devices, such as a pressure sensor, a thermal sensor, an electrical sensor (e.g., current, voltage, resistance, and/or impedance sensors), or a visualization element. Sensors 7 can provide feedback to an operator using catheter 10 by measuring parameters in the surrounding environment and thereby indicating a status of the catheter 10 and components thereof, and further providing for guidance on what additional steps the operator may decide to implement with catheter 10. For example, in implementations where the sensor devices include a visualization element, an operator of the catheter 10 may be able to more clearly understand where the catheter device 10 is located relative to a target lesion or anatomy, prior to, during, and after delivering therapy.

An energy supply port 24 is also located on the proximal end 22 to provide a connection between the shock wave emitter(s) 15 and/or 16 and an external energy source 28, such as the intravascular lithotripsy (IVL) generator shown in FIG. 1. The energy source 28 may be a pulse high voltage energy source. For treatment of an occlusion in a blood vessel, the voltage pulse applied by the power source 28 is typically in the range of from about five hundred to three thousand volts (500-3,000 V). In some implementations, the voltage pulse applied by the voltage source can be up to about ten thousand volts (10,000 V) or higher than ten thousand volts (10,000 V). The pulse width of the applied voltage pulses ranges between two microseconds and six microseconds (2-6 μs). The repetition rate or frequency of the applied voltage pulses may be between about 1 Hz and 10 Hz. The total number of pulses applied by the power source 28 may be, for example, sixty (60) pulses, eighty (80) pulses, one hundred twenty (120) pulses, three hundred (300) pulses, or up to five hundred (500) pulses, or other increments of pulses within this range. Alternatively, or additionally, in some examples, the power source 28 may be configured to deliver one or more packets of micro-pulses having a sub-frequency between about 100-10 kHz. The preferred voltage, repetition rate, and number of pulses may vary depending on, e.g., the size of the lesion, the extent of calcification, the size of the blood vessel, the attributes of the patient, or the stage of treatment. For instance, a physician may start with low energy shock waves and increase the energy as needed during the procedure, or vice versa. The magnitude of the shock waves can be controlled by controlling the voltage, current, duration, and repetition rate of the pulsed voltage from the power source 28.

In an alternative implementation, for laser generation of shock waves, the energy source 28 generates a laser pulse that is transmitted into and absorbed by a fluid within the catheter. This absorption process rapidly heats and vaporizes the fluid, thereby generating the rapidly expanding vapor bubble, as well as the shock waves that propagate outward and modify the calcified plaque. The shock wave intensity is higher if a fluid is chosen that exhibits strong absorption at the laser wavelength that is employed. Accordingly, although some shock wave devices described herein generate shock waves based on high voltage pulses applied to electrodes, it should be understood that a shock wave device may additionally or alternatively use laser pulses transmitted through optical fibers to generate shock waves and that the "emitters" and "shock wave generating regions" described herein may include output ends of optical fibers. These examples are not intended to be a comprehensive list of potential energy sources to create shock waves in shock wave catheters.

The catheter 10 also includes a flexible shaft 12 that extends from the proximal end 22 to the distal end 14 of the catheter. The shaft 12 provides various internal conduits connecting elements of the distal end 14 with the proximal end 22 of the catheter (see, e.g., FIG. 6D for a cross-section of a region an exemplary shaft). The shaft 12 includes an elongate tube that includes a lumen for receiving the guidewire 21. The cutting mechanism 32 may be positioned within a lumen of the shaft 12. In some examples, the cutting mechanism 32 is positioned within the same lumen for receiving guidewire 21 and may be configured such that guidewire 21 can be received into the cutting mechanism 32. The elongate tube may include additional lumens extending through the shaft 12 or along an outer surface of the shaft 12. For example, one for fluid lumens (e.g., a fluid inlet lumen and a fluid outlet lumen or a combined flush lumen) can be located along or within the shaft 12 for carrying conductive fluid from the fluid port 26 into the enclosure 30.

To operate the catheter 10, a physician inserts catheter 10 body lumen. The physician may advance the catheter 10 within the lumen until a pacemaker lead 20 is received into the distal end of catheter 10. Once positioned, the energy source 28 can be used to deliver one or more high voltage pulses to the emitters 15 and/or 16 to create one or more shock waves within the body lumen being treated. At least a portion of the shock waves propagate generally distally toward a target treatment area and into a lesion in a body lumen proximate to the distal end of the catheter 10 where the shock wave energy breaks up hardened plaque or otherwise modifies tissue at a target treatment area. A user may translate the cutting mechanism 32 to the extended position and rotate the cutting mechanism 32, for instance, to remove calcified and/or fibrotic tissue from a pacemaker lead 20. In some examples, a user (e.g., physician) may translate the cutting mechanism 32 to the extended position and rotate the cutting mechanism 32 to modify tissue distal of the distal end of catheter 10 prior to generating one or more shock waves. In some examples, the cutting mechanism 32 may be extended and rotated at the same time that one or more shock waves are generated using shock wave emitters 15 and/or 16.

In some examples, the magnitude of the shock waves can be controlled by controlling the magnitude of the pulsed voltage, the current, the duration, and the repetition rate of the voltage supplied by the power source 28. Furthermore, in examples where one or more emitters are wired on separate circuits or separate circuit branches to be operated separately, a user of the catheter 10 may selectively emit shock waves at only a particular subset of emitters of the catheter by applying a voltage to generate shock waves at only that subset of the emitters. The physician may start with low energy shock waves and increase the energy as needed to disrupt the lesion and crack calcified plaques. In some examples, a physician may first generate shock waves at a first subset of emitters (e.g., a distal subset of emitters) and may continue treatment by generating shock waves at a second subset of emitters (e.g., a central or proximal subset of emitters). Repeated shock waves can be delivered, and the catheter 10 can be repositioned or advanced further in the body lumen to continue treatment. When the shock wave treatment is completed, the enclosure(s) can be deflated and the distal end 14 of the catheter 10 removed from the body lumen.

Figure 2A:
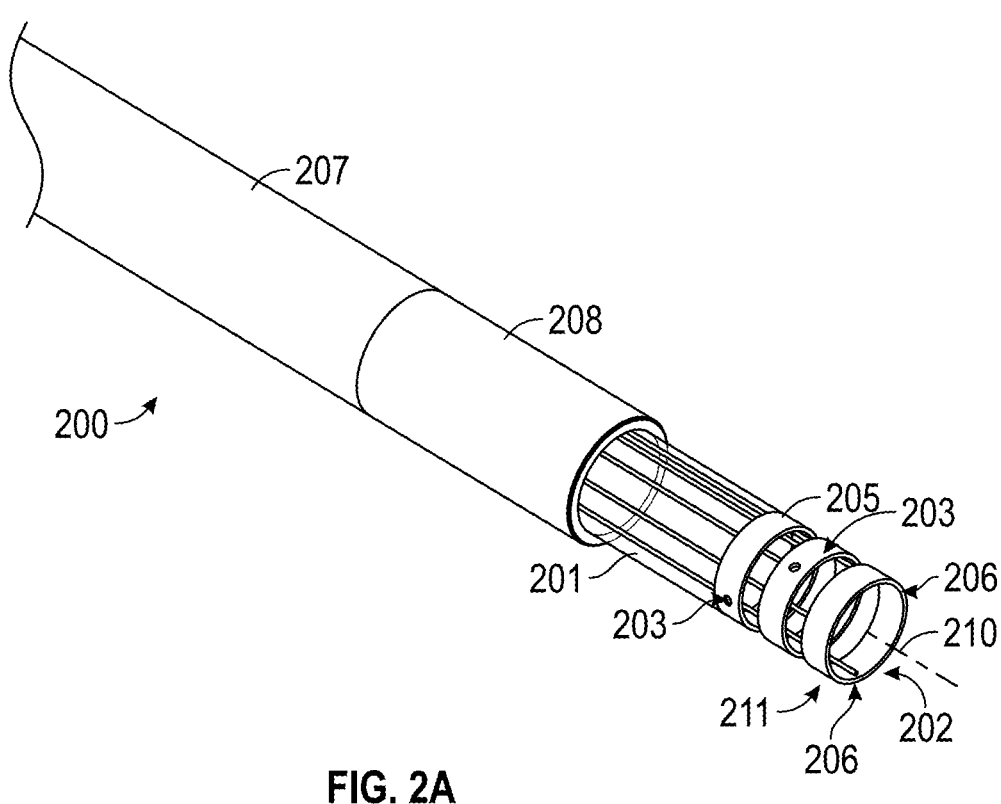
FIG. 2A is an illustration of a distal portion of an exemplary shock wave catheter with a shield in a retracted position in which shock wave emitters are uncovered, according to one or more aspects of the present disclosure.
Figure 2B:
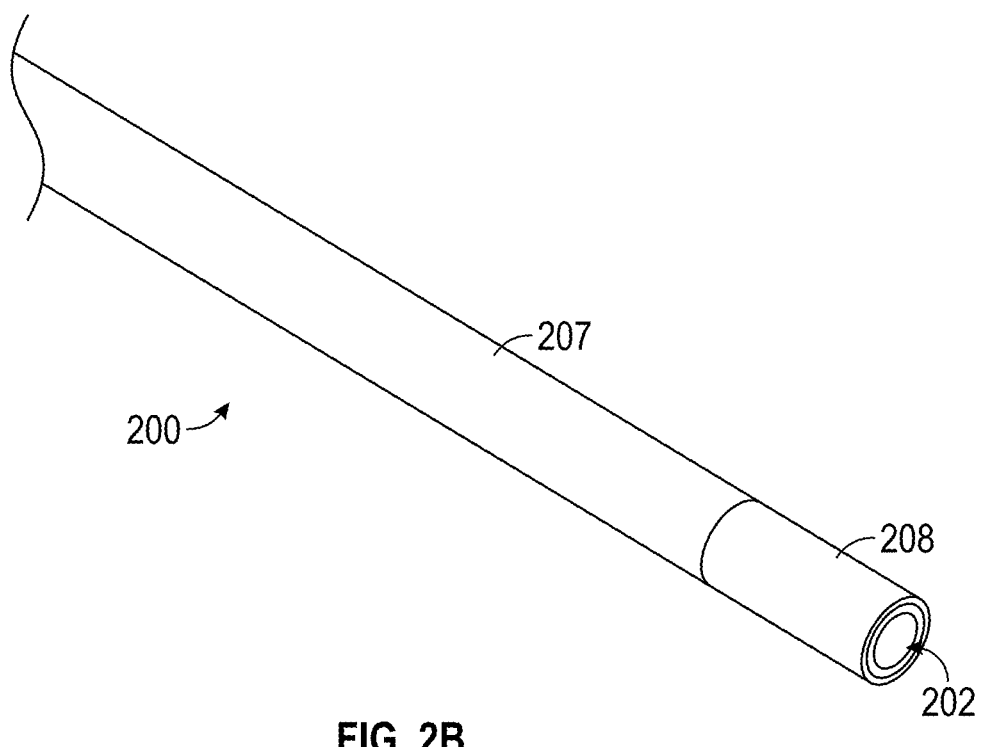
FIG. 2B is an illustration of the distal portion of the exemplary shock wave catheter of FIG. 2A with the shield in an extended position in which the shock wave emitters are covered by the shield, according to one or more aspects of the present disclosure.

FIGS. 2A and 2B illustrate aspects of a distal portion of a shock wave catheter 200 that can be used for catheter 10 of FIG. 1, according to one or more aspects of the present disclosure. The catheter 200 includes a catheter body 201. The catheter body 201 includes a cavity 202 at its distal end that opens in a distal direction. The catheter 200 includes one or more radially firing shock wave emitters 203 located outwardly of and adjacent to the cavity 202. The one or more radially firing shock wave emitters 203 can generate shock waves that propagate radially outwardly relative to the longitudinal axis 210 of the catheter body 201.

Optionally, the catheter body 201 may include one or more forward firing shock wave emitters 206 configured to generate shock waves that propagate in a forward direction, distally of the distal end 211 of the catheter body 201. One or more of the radially firing shock wave emitters 203 and/or one or more of the forward firing shock wave emitters 206 may be formed, in part, by one or more emitter bands 205 that extend at least partially around the longitudinal axis 210. The illustrated example includes three emitter bands 205, the two proximal emitter bands 205 forming radially firing shock wave emitters 203 and the distal emitter band forming forward firing shock wave emitters 206. In some examples, one or more radially firing shock wave emitter 203 and/or one or more of the forward firing shock wave emitter 206 may be formed by optical fibers extending from a power source configured to generate laser pulses.

A sheath 207 may extend around the catheter body 201 and may include a shield 208 at its distal end. The sheath 207 may be movable relative to the catheter body 201 in the longitudinal direction of the catheter body 201. FIG. 2A shows the sheath 207 in a retracted position relative to the catheter body 201, and FIG. 2B shows the sheath in an extended position relative to the catheter body 201. When in the extended position of FIG. 2B, the shield 208 may cover one or more of the radially firing shock wave emitters 203. In the illustrated example, the shield 208 is configured to cover all of the radially firing shock wave emitters 203. The shield 208 is made of a material that can reflect the shock waves generated by the radially firing shock wave emitters 203. As such, when the shield 208 covers one or more of the radially firing shock wave emitters 203, shock waves generated by the covered radially firing shock wave emitters 203 are reflected inwardly into the cavity 202. The reflected shock waves can break up target material (e.g., calcified and/or fibrotic material) disposed at least partially within the cavity 202. The shock waves may propagate in a forward direction and impact target material located in front of the distal end 211 of the catheter body 201.

With the sheath 207 in a retracted position illustrated in FIG. 2A, the radially firing shock wave emitters 203 are uncovered. Shock waves generated by the one or more radially firing shock wave emitters 203 when uncovered may propagate radially outwardly to impact target material located radially outwardly of the catheter 200. Thus, the radially firing shock wave emitters 203 may be used selectively to break up target material located at least partially within the cavity 202 and/or target material located radially outward of the catheter 200 simply by extending or retracting the sheath 207. As noted above, the catheter 200 may include one or more forward firing shock wave emitters 206 that can be used to direct shock waves in a forward direction to break up target material located forward of the catheter, providing yet another mode of action of the catheter 200. These three modes for generating shock waves—generating radially-outwardly directed shock waves, generating radially-inwardly directed shock waves, and generating forward directed shock waves—can be used independently and/or in concert to treat target material (e.g., to break up calcifications and/or fibrotic tissue). For example, with reference to the illustration of FIG. 1, catheter 200 can be used to tunnel into the stenotic lesion by generating shock waves from the forward firing shock wave emitter(s) 206 and/or from the radially firing shock wave emitters 203 while the shield 208 is in an extended position to break up portions of the stenotic lesion positioned within the cavity 202 and/or in front of the catheter. The shield 208 can then be retracted and shock waves can be generated by the radially firing shock wave emitters 203 to break up portions of the stenotic lesion located radially outwardly of the catheter.

The sheath 207 may be formed from at least one reinforced wire material. The wire material can braided, coiled, or both. The wire material may be round or may be flat to provide a lower profile. The sheath 207 may be configured to contribute mechanical strength to the catheter 200. For instance, the material composition of the sheath 207 could provide increased torqueability, pushability, and/or enhanced rigidity to the catheter 200 to facilitate maneuvering the catheter 200 through a patient's vasculature. The sheath 207 can be laminated with one or more polymer liners. A polymer liner can be formed of any suitable material (e.g., nylon) to allow for improved mechanical properties such as pushability and torqueability.

The shield 208 may be formed from a hard material that is capable of reflecting shock waves (e.g., stainless steel, platinum-iridium alloy, chromium, etc.). The shield 208 can be formed of a radiopaque material or include radiopaque material to facilitate fluoroscopic tracking of the catheter 200. The shield 208 may be mounted to the sheath 207 in any suitable fashion, such as via a press fit between the shield 208 and the sheath 207 and/or an adhesive attachment between the shield 208 and the sheath 207. In some embodiments, the sheath 207 is made of a material that can reflect shock waves such that the shield 208 is not a separate component but, rather, a distal region of the sheath 207.

The catheter body 201 may be made of any suitable material. Examples of suitable material include urethane, polyether block amide (e.g., Pebax), and other low durometer polymer material.

Figure 3A:
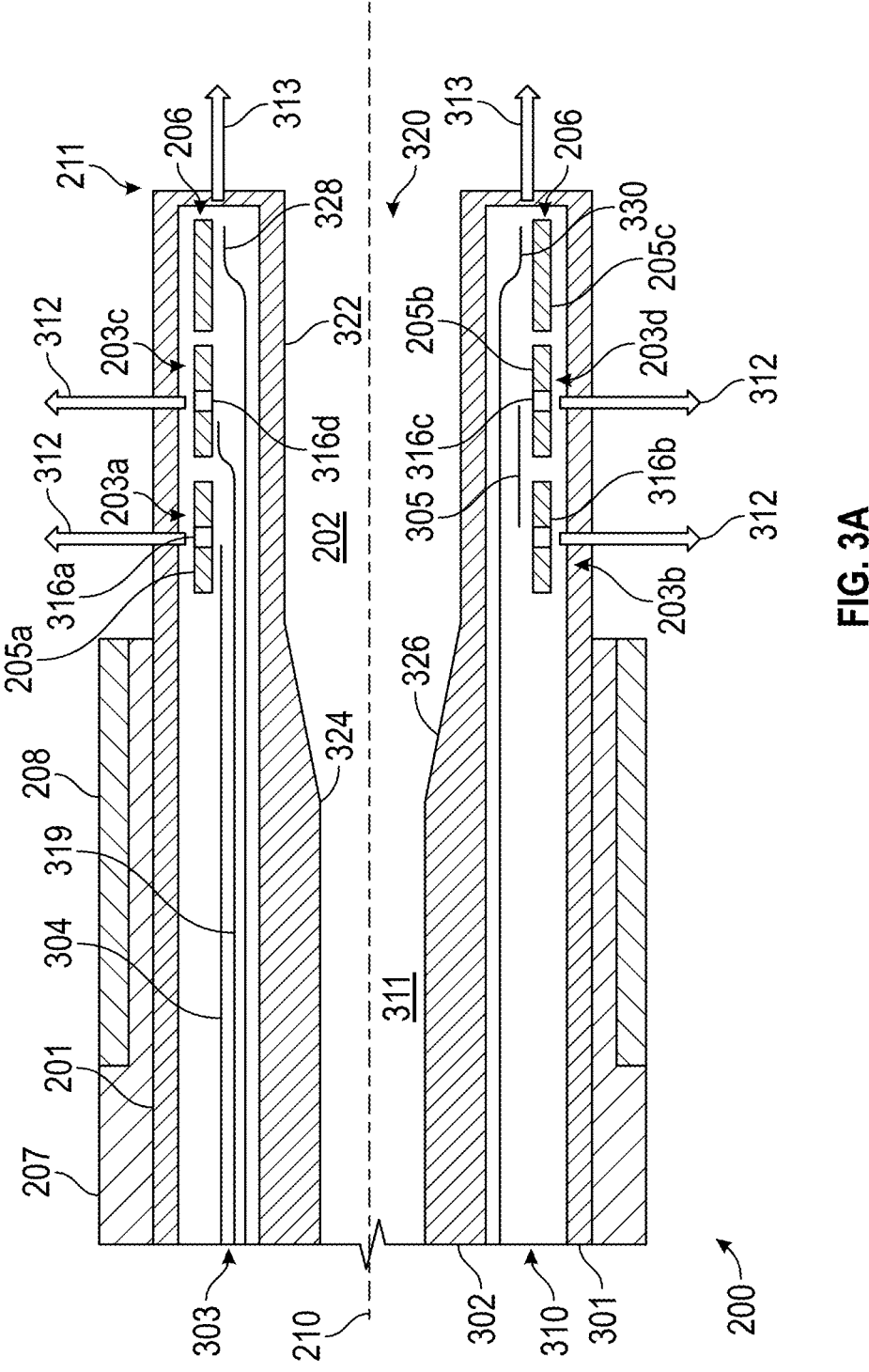
FIGS. 3A-3C are cross sectional illustrations of the distal portion of the catheter of FIGS. 2A and 2B with the shield in retracted and extended positions, according to one or more aspects of the present disclosure.
Figure 3B:
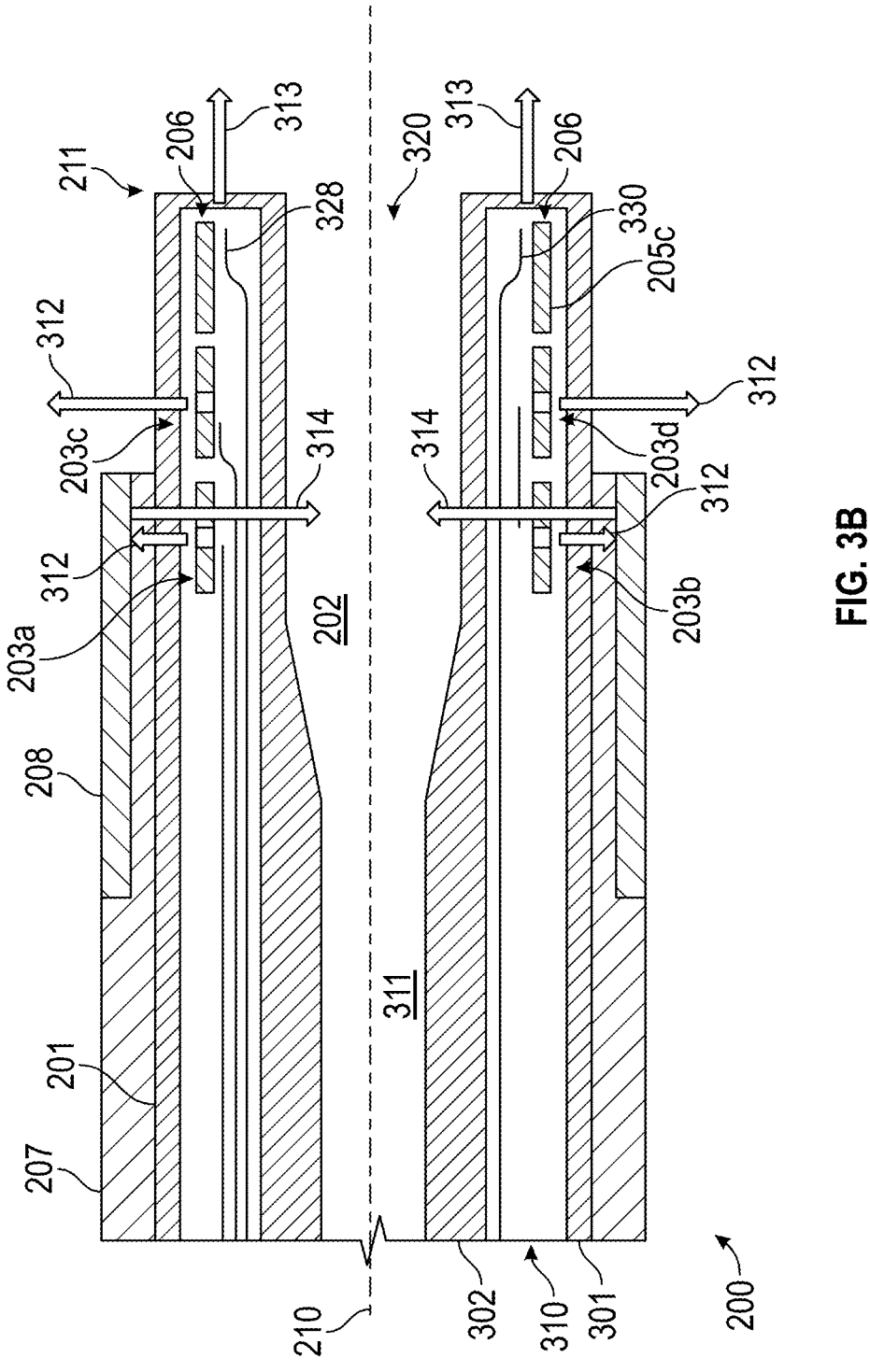
Figure 3C:
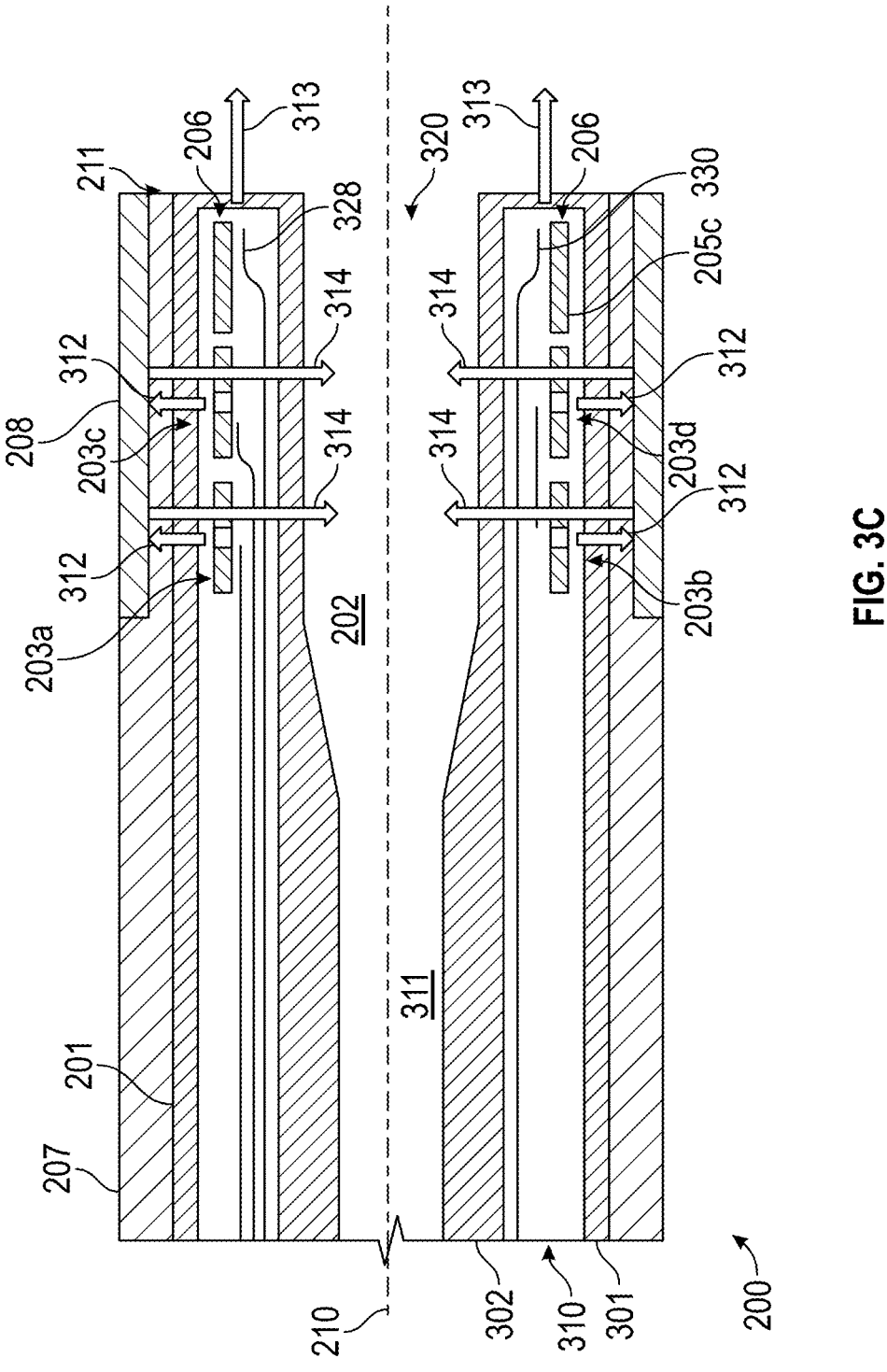

FIGS. 3A-3C illustrate cross sectional views of an example of the distal portion of catheter 200 of FIGS. 2A and 2B. FIG. 3A shows the catheter 200 with the sheath 207 in a retracted position and FIGS. 3B and 3C show the catheter 200 with the sheath 207 in different extended positions. The catheter body 201 may include an outer wall 301 and an inner wall 302 that are spaced from one another to form an annular lumen 310. The annular lumen 310 may house at least one radially firing shock wave emitter located radially inwardly of the outer wall 301 and radially outwardly of the inner wall 302 and may be filled with a conductive fluid. The illustrated example includes four radially firing shock wave emitters—203a, 203b, 203c, and 203c. The proximal radially firing shock wave emitters 203a and 203b in the illustrated example are located at the same longitudinal position but at opposite circumferential positions. The distal radially firing shock wave emitters 203c and 203d in the illustrated example are located at the same longitudinal position, distal of the proximal radially firing shock wave emitters 203a and 203b, and are located at opposite circumferential positions. The illustrated arrangement of the radially firing shock wave emitters is merely exemplary. The catheter can include any number of radially firing shock wave emitters in any longitudinal and circumferential locations.

The inner wall 302 may form a cavity 202 that has an open distal end 320. The inner wall 302 may reduce in diameter from a larger diameter section 322 that defines the cavity 202 to a smaller diameter section 324 that defines a central lumen 311. The larger diameter section 322 may have a diameter of up to 1 mm, up to 0.750 mm, up to 0.500 mm, or up to 0.250 mm. The diameter of the larger diameter section 322 may be at least 0.010 mm, at least 0.020 mm, or at least 0.050 mm. In some examples, the diameter of the larger diameter section 322 is in the range of 0.050 mm to 0.250 mm. A length of the cavity 202 may be up to 3 cm, up to 2 cm, or up to 1 cm. The length of the cavity 202 may be at least 1 mm, at least 2 mm, or at least 3 mm. In some examples, the length of the cavity 202 is in the range of 3 mm to 1 cm. The central lumen 311 may receive a guidewire and/or a pacemaker lead. The inner wall 302 may include a narrowing section 326 that transitions from the larger diameter section 322 to the smaller diameter section 324. The narrowing section 326 can have any suitable shape, including a tapering shape as shown, a stepped shape, a domed shape, or a funnel shape.

When the sheath 207 is in a retracted position such that the shield 208 is not covering the radially firing shock wave emitters 203a-d, as illustrated in FIG. 3A, shock waves generated by the radially firing shock wave emitters 203a-d propagate radially outwardly relative to the longitudinal axis 210 in direction 312. These shock waves can break up calcifications or fibrotic tissue (not shown) located radially outwardly of the catheter 200.

When the sheath 207 is in an extended position such that shield 208 is covering one or more of the radially firing shock wave emitters 203a-d, as illustrated in FIGS. 3B and 3C, shock waves generated by the covered radially firing shock wave emitters 203a-d propagate radially outwardly in direction 312 and are then reflected by shield 208 radially inwardly (e.g., in direction 314) into the cavity 202. The reflected shock waves may impinge on calcified or fibrotic material located within the cavity 202. Shock waves may constructively interfere within the cavity 202, amplifying the destructive effect of the shock waves on the calcified or fibrotic material. Shock waves may be reflected multiple times by the shield 208. Shock waves may propagate in a distal direction, out through the open distal end 320 of the cavity 202. Optionally, the narrowing section 326 is configured to reflect shock waves in a distal direction. As such, the catheter 200 can be used with the shield 208 covering the radially firing shock emitters 203a-d for treating target material located within the cavity 202 and/or in front of the cavity 202.

While FIG. 3B shows the shield 208 covering all of the radially firing shock wave emitters 203a-d, the shield 208 may be positioned so that it covers one or more of the shock wave emitters 203a-d but not all of them, enabling some shock waves to propagate radially outwardly and others to be reflected radially inwardly. An example of this is illustrated in FIG. 3C in which the shield is positioned to cover radially firing shock wave emitters 203a and 203b but not radially firing shock wave emitters 203c and 203d. By covering some but not all of the radially firing emitters, the catheter 200 could be used to treat calcified and/or fibrotic material or other target material located both outside of the catheter 200 and within and/or in front of the cavity 202.

Optionally, at least one forward firing shock wave emitter 206 may be positioned in the annular lumen 310, at the distal end 211 of the catheter body 201, distally of the radially firing shock wave emitters 203a-d. The one or more forward firing shock wave emitters 206 can be configured to generate shock waves directed forward in direction 313, past the distal end of the catheter 200, such as to break up calcifications or fibrotic tissue (not shown) located forward of the catheter 200. The one or more forward firing shock wave emitters 206 could be used to treat calcified and/or fibrotic material located in front of the catheter 200 and the radially firing shock wave emitters 203 could be used to treat calcified and/or fibrotic material located in radially outward of the catheter 200 and/or within the cavity 202.

The one or more radially firing shock wave emitters 203a-d and the one or more forward firing shock wave emitters 206 may generate shock waves based on voltage pulses applied to the emitters from a voltage pulse generator (e.g., shock wave power source 28 of FIG. 1). A plurality of conductors 303 may extend in the annular lumen 310 to the radially firing shock wave emitters 203 and/or forward firing shock wave emitters 206 to provide voltage pulses to the shock wave emitters for generating shock waves. The plurality of conductors 303 may electrically connect the one or more radially firing shock wave emitters 203 and/or the one or more forward firing shock wave emitters 206 to a shock wave power source and/or to each other.

In the illustrated example, the conductors 303 are configured so that the radially firing shock wave emitters 203a-d are arranged serially such that a voltage pulse can cause each of the radially firing shock wave emitters 203a-d to generate a shock wave. Each of the radially firing shock wave emitters 203a-d is formed by an electrode pair that includes an end of one of the conductors 303 and a portion of an emitter band 205.

A first conductor 304 extends proximally to a first emitter band 205a. The first emitter band 205a extends around the longitudinal axis 210, within the annular lumen 310. The distal end of the first conductor 304 is uninsulated and is located adjacent to but spaced from a first hole 316a in the first emitter band 205a. The distal end of the first conductor 304 and the first emitter band 205a together form an electrode pair of radially firing shock wave emitter 203a. In use, a suitable voltage pulse applied to the electrode pair formed by the distal end of the first conductor 304 and the first emitter band 205a causes an electrical arc to form across the gap between them in conductive fluid that fills the annular lumen 310, which results in the generation of one or more shock waves.

Radially firing shock wave emitter 203b is formed by the first emitter band 205a and a proximal end of a second conductor 305. The proximal end of the second conductor 305 is uninsulated and located adjacent to but spaced from a second hole 316b in the first emitter band 205a. The proximal end of the second conductor 305 and the first emitter band 205a form the electrode pair of radially firing shock wave emitter 203a.

The second conductor 305 extends distally to a second emitter band 205b, which extends around the longitudinal axis 210 within the annular lumen 310. The distal end of the second conductor 305 is uninsulated and adjacent to but spaced from a hole 316c in the second emitter band 205b. The distal end of the second conductor 305 and the second emitter band 205b together form the electrode pair of radially firing shock wave emitter 203c. Radially firing shock wave emitter 203d is formed by the second emitter band 205b and an uninsulated distal end of a third conductor 319, which is adjacent to but spaced from a hole 316d in the second emitter band 205b. The third conductor 319 extends toward a proximal end of the catheter 200 for connection to a voltage source (directly or via one or more intermediate conductors).

In use, a voltage may be applied across first conductor 304 and third conductor 319 (e.g., across proximal ends of the first conductor 304 and third conductor 319) that causes current to flow across the gap between the distal end of the first conductor 304 and the first emitter band 205*a*, through the first emitter band 205*a*, across the gap between the first emitter band 205*a* and the proximal end of the second conductor 305, along the second conductor 305, across the gap between the distal end of the second conductor 305 and the second emitter band 205*b*, through the second emitter band 205*b*, and across the gap between the second emitter band 205*b* and the distal end of the third conductor 319 resulting in shock waves being generated at each of the radially firing shock wave emitters 203*a-d*.

Additional conductors may be provided for providing voltage pulses to one or more forward firing shock wave emitters 206. The illustrated example includes two conductors 328 and 330 that provide voltage pulses to two forward firing shock wave emitters 206*a* and 206*b*. The forward firing shock wave emitters 206*a* and 206*b* include electrode pairs formed by a distal end of a respective one of the conductors 328 and 330 and a third emitter band 205*c*. Distal ends of each of the conductors 328 and 330 are spaced by respective gaps from the distal end of the third emitter band 205*c*. Voltage pulses can be applied to the conductors 328 and 330 so that sparks form across the gap between conductor 328 and the third emitter band 205*c* and across the gap between conductor 330 and the third emitter band 205*c* (which, in the illustrated example, is opposite the gap between conductor 328 and the third emitter band 205*c*), generating shock waves at those two locations that propagate in a distal direction as indicated by arrows 313.

The arrangement of the radially firing shock wave emitters 203*a-d* and forward firing shock wave emitters 206*a-b* illustrated in FIGS. 3A and 3B is merely exemplary. Any number, arrangement, and configuration of radially firing and/or forward firing emitters may be used. For example, one or more radially firing shock wave emitters may be formed by gaps between two wires, rather than between a wire and an emitter band. In some examples, radially firing shock wave emitters are formed by locating conductors adjacent to an end of an emitter band or a notch in the end of an emitter band, rather than a hole in the emitter band. In some examples, radially firing shock wave emitters are circumferentially spaced 180 degrees from each other (such as shown in FIG. 3A). However, any circumferential spacing may be used, including 60 degrees, 90 degrees, 120 degrees, etc. In some examples, emitters provided by each emitter band are circumferentially spaced from each other by 180 degrees and adjacent emitter bands are arranged such that a set of emitters formed by a first band are circumferentially offset from a set of emitters formed by a second emitter band, such as by 90 degrees, so that, collectively, emitters are spaced at 90 degree intervals.

Figure 3D:
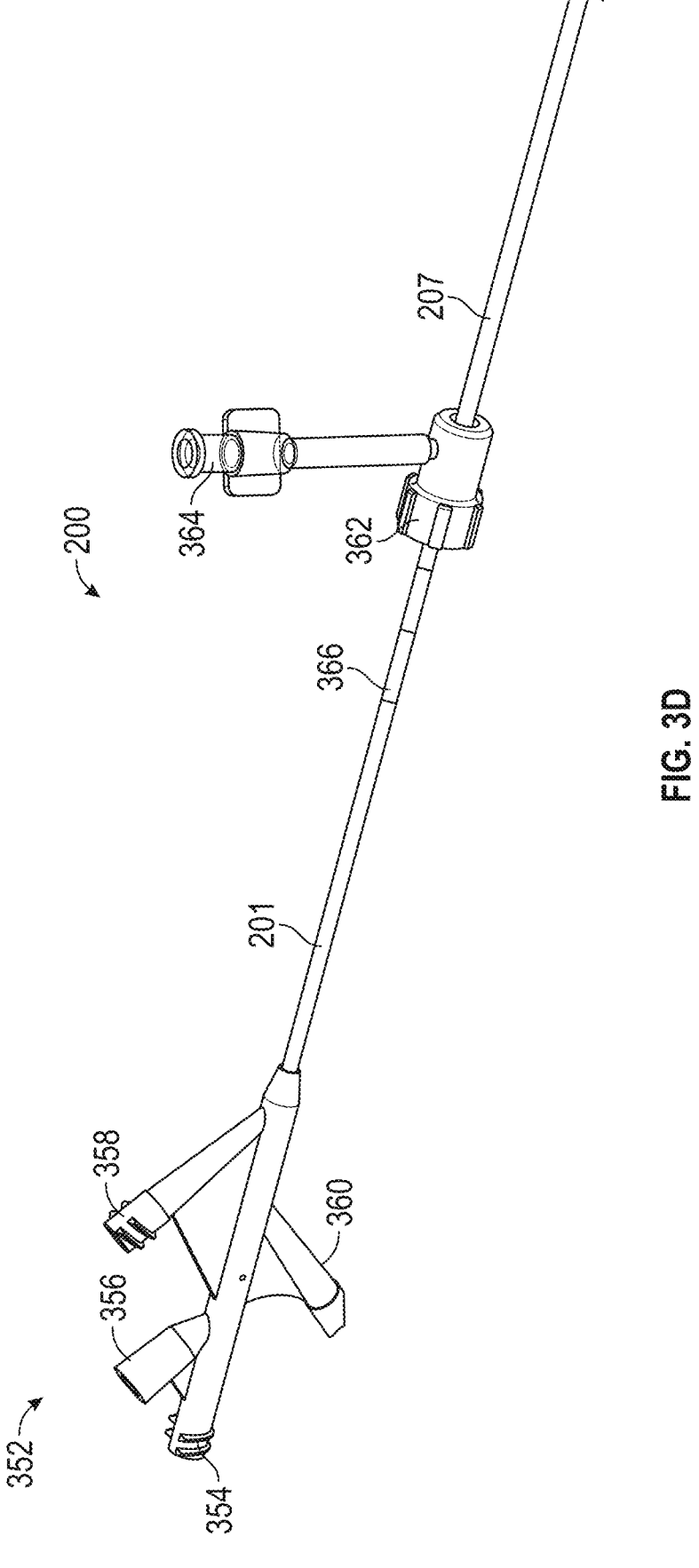
FIG. 3D is an illustration of a proximal portion of a catheter, according to one or more aspects of the present disclosure.

FIG. 3D illustrates an example of a proximal portion of catheter 200. The catheter 200 may include a proximal hub 352 located at a proximal end of the catheter body 201. The proximal hub 352 may include a port 354 through which a proximal portion of a guidewire and/or pacemaker disposed in the central lumen 311 (FIG. 3A) may extend. The proximal hub 352 may include a port 356 through which the conductors 303 may extend for connection to a power source (e.g., shock wave power source 28 of FIG. 1). The proximal hub 352 may include an inlet port 358 and an outlet port 360 that communicate with the annular lumen 310 for filling the annular lumen 310 with conductive fluid and/or for purging air from the annular lumen 310.

Catheter 200 may include a hemostasis valve 412 located at a distal end of sheath 207. The hemostasis valve 362 may include a port 364 that is in communication with an annular space between the sheath 207 and the catheter body 201 and which can be used to flow fluid into and/or out of the space between the sheath 207 and the catheter body 201. A seal (not shown) may be provided between the hemostasis valve 362 and the catheter body 201 so that fluid does not flow proximally out of the hemostasis valve 362 while still permitting relative motion between the hemostasis valve 362 and the catheter body 201. Optionally, the hemostasis valve 362 may be used for translating the sheath 207 relative to the catheter body 201. For example, a user may grasp the hemostasis valve 362 and move it distally or proximally while holding the proximal hub 352 in place to advance or retract the shield 308. The catheter body 201 may include one or more indicators 366 for indicating a longitudinal location of the sheath 207 (and, therefore, the shield 208) along the catheter body 201.

Figure 4:
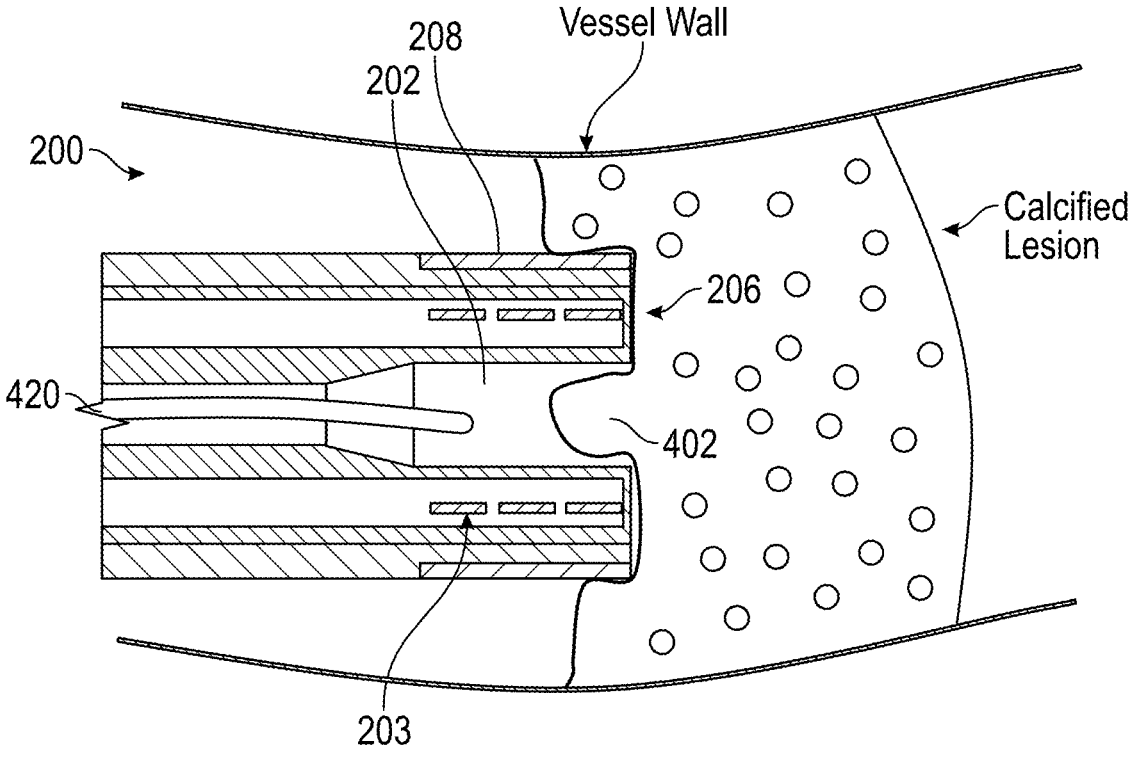
FIG. 4 is an illustration of a cross sectional view of a catheter being used to treat a vascular occlusion, according to one or more aspects of the present disclosure.

FIG. 4 illustrates an example of catheter 200 being used to treat a calcified lesion in a blood vessel. In operation, a physician advances a guidewire 420 from an entry site on a patient (e.g., an artery in the groin area of the leg) to a target region of the vessel that includes the calcified lesion. The catheter 200 is then advanced over the guidewire 420 to the target region. The in-situ location of the distal end of the catheter 200 may be determined by, for example, fluoroscopy. The guidewire 20 and/or the catheter 200 may be advanced at least partially into the calcified lesion, such that a portion 402 of the calcification is positioned in the cavity 202. Optionally, one or more forward firing shock wave emitters 206 may be used to break at least some of the calcified lesion so that the catheter 200 may be advanced into the calcified lesion.

The shield 208 may be in a distal position (as shown) such that the shield 208 covers the one or more radially firing shock wave emitters 203. Shock waves may then be generated by the one or more radially firing shock wave emitters 203 (e.g., by a user activating the shock wave power source 28 of FIG. 1). The shock waves propagate radially outwardly and are reflected inwardly by the shield 208 into the cavity 202 where the shock waves may break up the portion 402 of the calcification positioned at least partially within the cavity 202 and/or calcification located in front of the distal end of the cavity 202. Subsequently, the shield 208 can be translated proximally such that the one or more radially firing shock wave emitters 203 are uncovered by the shield 208. Shock waves can be generated by the one or radially firing shock wave emitters 203, which propagate radially into calcifications surrounding the catheter to break up the calcifications. The one or more radially firing shock wave emitters 203 and the one or more forward firing shock wave emitters 206 may generate shock waves simultaneously, in a specified sequence, independently, or any combination thereof.

For treatment of occlusive material in a blood vessel, the shock waves may be generated by applying a voltage pulse to the one or more radially firing shock wave emitters 203 and/or the one or more forward firing shock wave emitters 206. In some examples, the voltage pulse is in the range of from about two thousand to three thousand volts (2,000-3,000 V). In some examples, the voltage pulse is up to about ten thousand volts (10,000 V). The pulse width of the applied voltage pulses may range between two microseconds and six microseconds (2-6 µs). The repetition rate or frequency of the applied voltage pulses may be between about 1 Hz and 10 Hz. The total number of pulses applied may be, for example, sixty (60) pulses, eighty (80) pulses, one hundred twenty (120) pulses, three hundred (300) pulses, or up to five hundred (500) pulses, or other increments of pulses within this range. The preferred voltage, repetition rate, and number of pulses may vary depending on, e.g., the size of the lesion, the extent of calcification, the size of the blood vessel, the attributes of the patient, or the stage of treatment. For instance, a physician may start with low energy shock waves and increase the energy as needed during the procedure, or vice versa. The magnitude of the shock waves can be controlled by controlling the voltage, current, duration, and repetition rate of the pulsed voltage.

The progress of the procedure may be monitored by Intravascular ultrasound, optical coherence tomography, X-ray, and/or fluoroscopy. As the occlusion is broken up or loosened by the shock waves, the catheter 200 can be advanced farther into the occlusion, and the shock wave treatment can be repeated, as necessary. Once the lesion has been sufficiently treated, the catheter 200 and the guidewire 420 can be withdrawn from the patient.

Figure 5A:
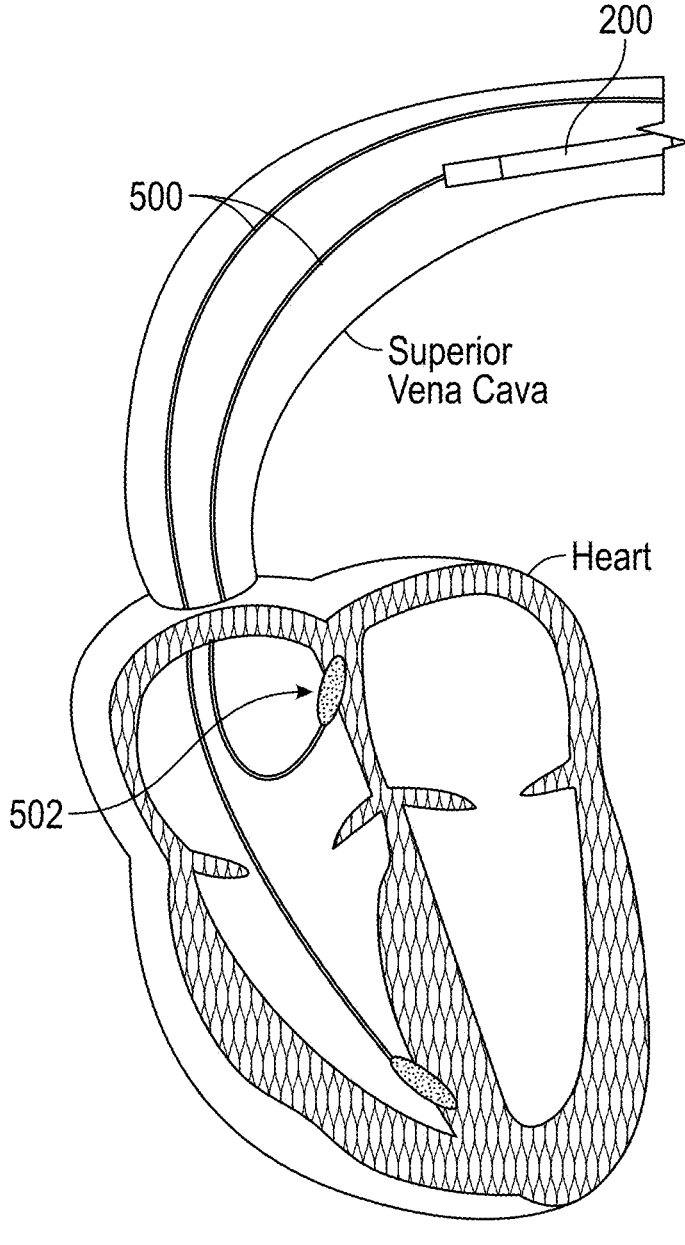
FIGS. 5A and 5B are illustrations of an exemplary use of a catheter for facilitating removal of a pacemaker lead, according to one or more aspects of the present disclosure.

FIG. 5A illustrates aspects of the use of the catheter 200 to facilitate removal of a pacemaker lead. Pacemaker leads may become at least partially encased in fibrotic and/or calcified tissue that further anchors the pacemaker leads to the heart tissue and/or vessel walls, making them difficult to remove. This lead entrapment is a result of the natural immuno response of the body to foreign objects. Catheter 200 can be used to break up the fibrotic tissue by advancing the catheter 200 to the site of the fibrotic tissue and using shock waves to break up the fibrotic tissue. To do this, a physician may thread a proximal end of a pacemaker lead 500 through the central lumen 311 of the catheter 200 (see FIG. 3A) and may advance the catheter 200 from an entry site of a patient (e.g., a vein in the shoulder or the leg) to the site of the fibrotic tissue, such as to the location 502 where the pacemaker lead is embedded in the heart wall. The in-situ location of the distal end of the catheter 200 may be determined by x-ray imagining and/or fluoroscopy.

Figure 5B:
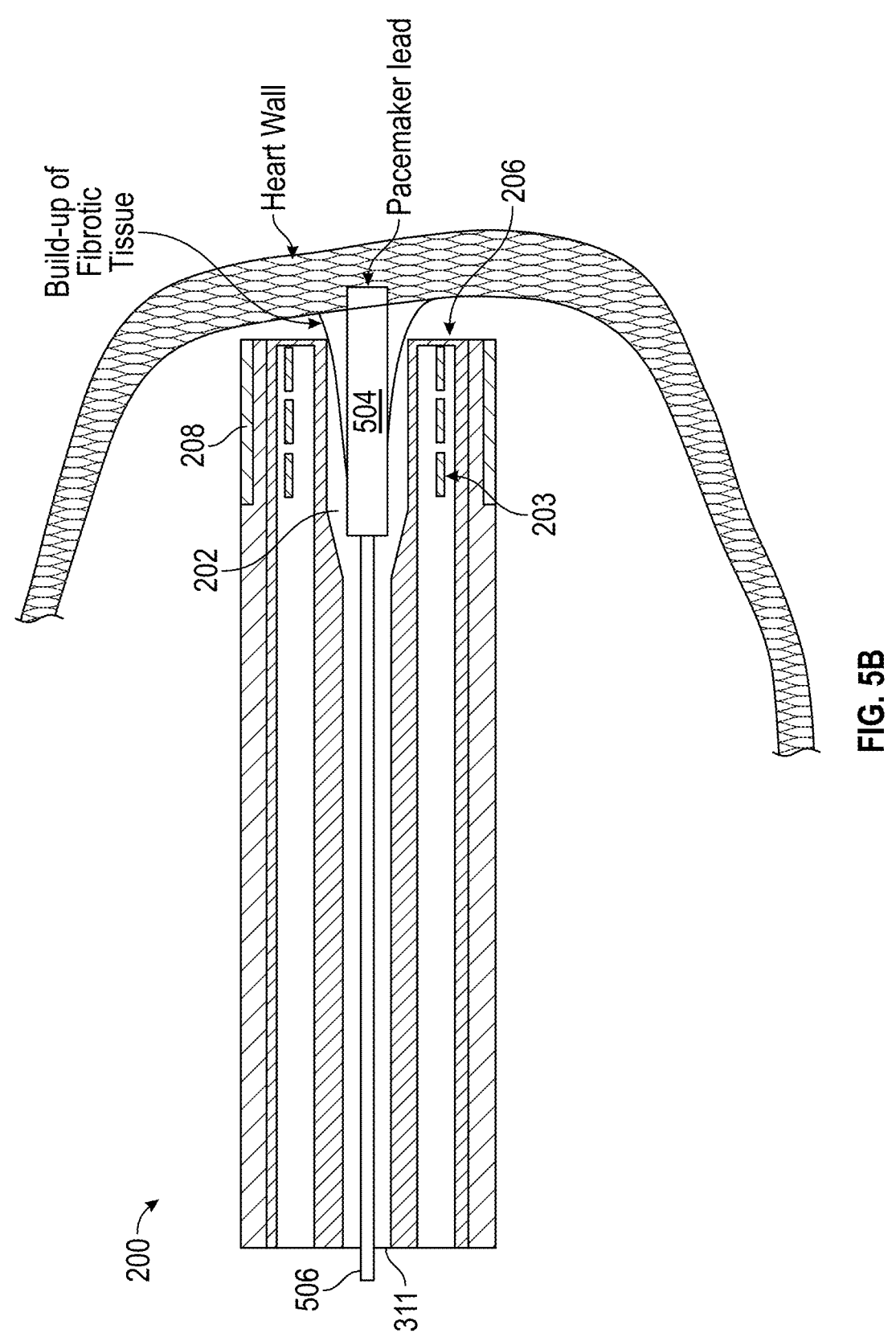

FIG. 5B shows the catheter 200 at the treatment location 502 where the distal portion 504 of the pacemaker lead 500 is implanted in the heart wall and fibrotic tissue has grown around it. As illustrated, the pacemaker lead wire 506 extends through the central lumen 311 of the catheter 200. The catheter 200 has been positioned such that the distal portion 504 of the pacemaker lead 500 is at least partially positioned in the cavity 202 at the distal end of the catheter 200. Fibrotic tissue encasing the distal portion 504 of the pacemaker lead 500 is also located at least partially in the cavity 202. The cavity 202 may be sized so that the distal portion 504 of the pacemaker lead 500 may fit within the cavity 202 while being at least partially encased by fibrotic tissue.

The shield 208 is located in a distal position such that the shield 208 covers the one or more radially firing shock wave emitters 203. Shock waves are generated by the one or more radially firing shock wave emitters 203. The shock waves are reflected inwardly and impinge on the fibrotic tissue within the cavity 202. The shock waves may travel distally to treat fibrotic tissue located in front of the distal end of the catheter 200. Optionally, shock waves may be generated by the one or more forward firing shock wave emitters 206 to break up fibrotic tissue located in front of the distal end of the catheter 200. The breaking up of the fibrotic tissue helps free the pacemaker lead, enabling the pacemaker lead to be more easily removed. Optionally, a user may advance the catheter 200 to the location of the fibrotic tissue, may apply one or more shock waves to the fibrotic tissue, may retract the catheter 200, and may attempt to pull out the pacemaker lead from the heart wall. If removal of the pacemaker lead proves too difficult, the catheter may be extended back to the treatment site for additional treatment. Treatment may be repeated as many times as necessary until the pacemaker lead can be removed.

Although FIG. 5B depicts treatment of fibrotic tissue at a distal portion of the pacemaker lead, this is not intended to be limiting. The catheter can be used to treat fibrotic tissue at any location along the pacemaker lead, including in the vasculature leading to the heart.

For pacemaker lead removal, the shock waves may be generated by applying a voltage pulse to the one or more radially firing shock wave emitters 203 and/or the one or more forward firing shock wave emitters 206. In some aspects, the voltage pulse applied may be in the range of from about two thousand to three thousand volts (2,000-3,000 V). In some implementations, the voltage pulse applied may be up to about ten thousand volts (10,000 V). The pulse width of the applied voltage pulses may range between two microseconds and six microseconds (2-6 μs). The repetition rate or frequency of the applied voltage pulses may be between about 1 Hz and 10 Hz. The total number of pulses applied may be, for example, sixty (60) pulses, eighty (80) pulses, one hundred twenty (120) pulses, three hundred (300) pulses, or up to five hundred (500) pulses, or other increments of pulses within this range. The preferred voltage, repetition rate, and number of pulses may vary depending on, e.g., the condition of the pacemaker lead, the extent of fibrosis, the size of the blood vessel, the attributes of the patient, or the stage of treatment. For instance, a physician may start with low energy shock waves and increase the energy as needed during the procedure, or vice versa. The magnitude of the shock waves can be controlled by controlling the voltage, current, duration, and repetition rate of the pulsed voltage.

Figure 6A:
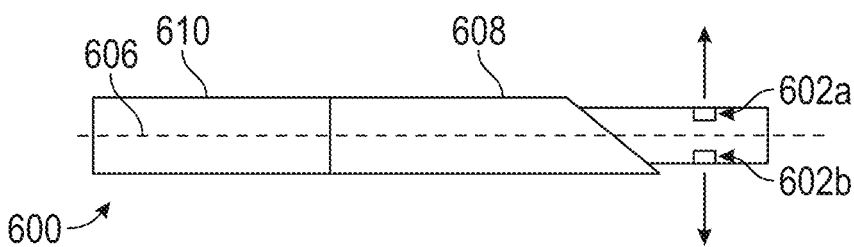
FIGS. 6A-C illustrate an example of a distal portion of an exemplary catheter that has a tapered shield, with FIG. 6A showing the shield in a retracted position, FIG. 6B showing the shield in a partially covering position, and FIG. 6C showing the shield in an extended position.
Figure 6B:
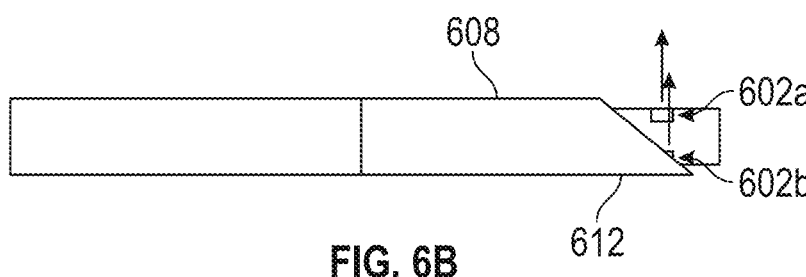
Figure 6C:
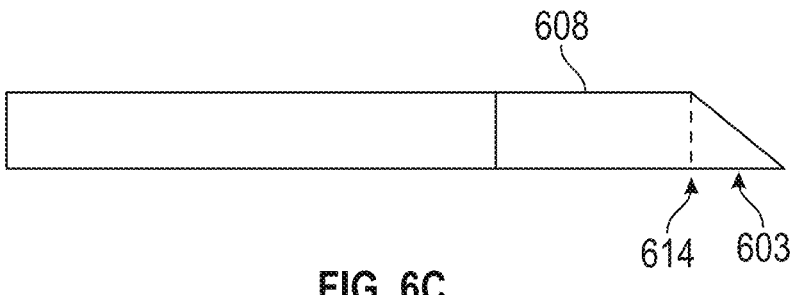

The shield illustrated in the examples of FIG. 2A-3B included a blunt distal end. In other examples, the shield has a tapered distal end. An example of a catheter having a shield with a tapered distal end is illustrated in FIGS. 6A-C, which illustrate a distal portion of a shock wave catheter 600. Shock wave catheter 600 can be used for catheter 10 of FIG. 1 and may be configured similarly to catheter 200 of FIG. 2A-B.

Catheter 600 may include a catheter body 601, a plurality of radially firing shock wave emitters 602a, 602b configured to emit shock waves radially outwardly relative to a longitudinal axis 606 of the catheter body 601, and a shield 608 located at a distal end of a sheath 610. Catheter body 601 may also include a cavity (not shown) at its distal end that opens in a distal direction, such as cavity 202 of catheter 200. Shield 608 can translate in a longitudinal direction of the catheter body 601 to selectively cover one or more of the radially firing shock wave emitters 602a, 602b such that shock waves generated by the one or more radially firing shock wave emitters 602a, 602b that are covered by the shield 608 can be reflected.

The shield 608 may have a tapered distal end 603. Optionally, the tapered distal end 603 may have a blunt tip or atraumatic tip to prevent damage to tissue such as blood vessels. Alternatively, the tapered distal end 603 may have a sharp tip configured to cut or pierce tissue, such as fibrotic tissue or calcified tissue. The shield is translatable along the catheter body 601. In FIG. 6A, the shield 608 is in a proximal position in which the shield 608 is located proximally of the radially firing shock wave emitters 602a, 60b leaving the radially firing shock wave emitters 602a, 60b uncovered. Shock waves generated by the one or more radially firing shock wave emitters 602*a*, 60*b* with the shield 608 in this position propagate radially outwardly in opposite directions to treat calcifications or fibrotic tissue surrounding the catheter 600, as discussed above.

FIG. 6B illustrates the catheter 600 with the shield 608 positioned such that the radially firing shock wave emitters 602*a* located on one side of the catheter 600 is covered by a long side 612 of the tapered distal end 603 and radially firing shock wave emitter 602*b* located on the other side of the catheter 600 remains uncovered. With the shield 608 in this position, shock waves generated by the covered radially firing shock wave emitters 602*a* are reflected by the shield 608 toward the uncovered radially firing shock wave emitters 602*b* where they can combine with shock waves generated by the uncovered radially firing shock wave emitters 602*b*. This enables the shock waves from both of the radially firing shock wave emitters 602*a*, 602*b* to be concentrated at a particular location, which may be beneficial in treating eccentric calcifications (calcifications that are not uniformly deposited around the circumference of the vessel). Different circumferential locations can be targeted by rotating the catheter 600 and/or by rotating the shield 608 about the catheter body 601 (e.g., by rotating the proximal end of the sheath 610). Optionally, the shield 608 includes or is made of radiopaque material that enables observation of an orientation of the shield 608 about a longitudinal axis of the catheter. The proximal end of the sheath 610 may include one or more indicators of a rotational position of the tapered distal end 603, which may help a user properly position the rotational position of the tapered distal end 603, such as for targeted a non-concentric lesion in a body lumen.

FIG. 6C illustrates the catheter with the shield 608 in a distal position in which the shield 608 extends distally of a distal end 614 of the catheter body 601. With the shield 608 in this position, the tapered distal end 603 may be used to cut or penetrate fibrotic tissue and/or calcifications.

Figure 7:
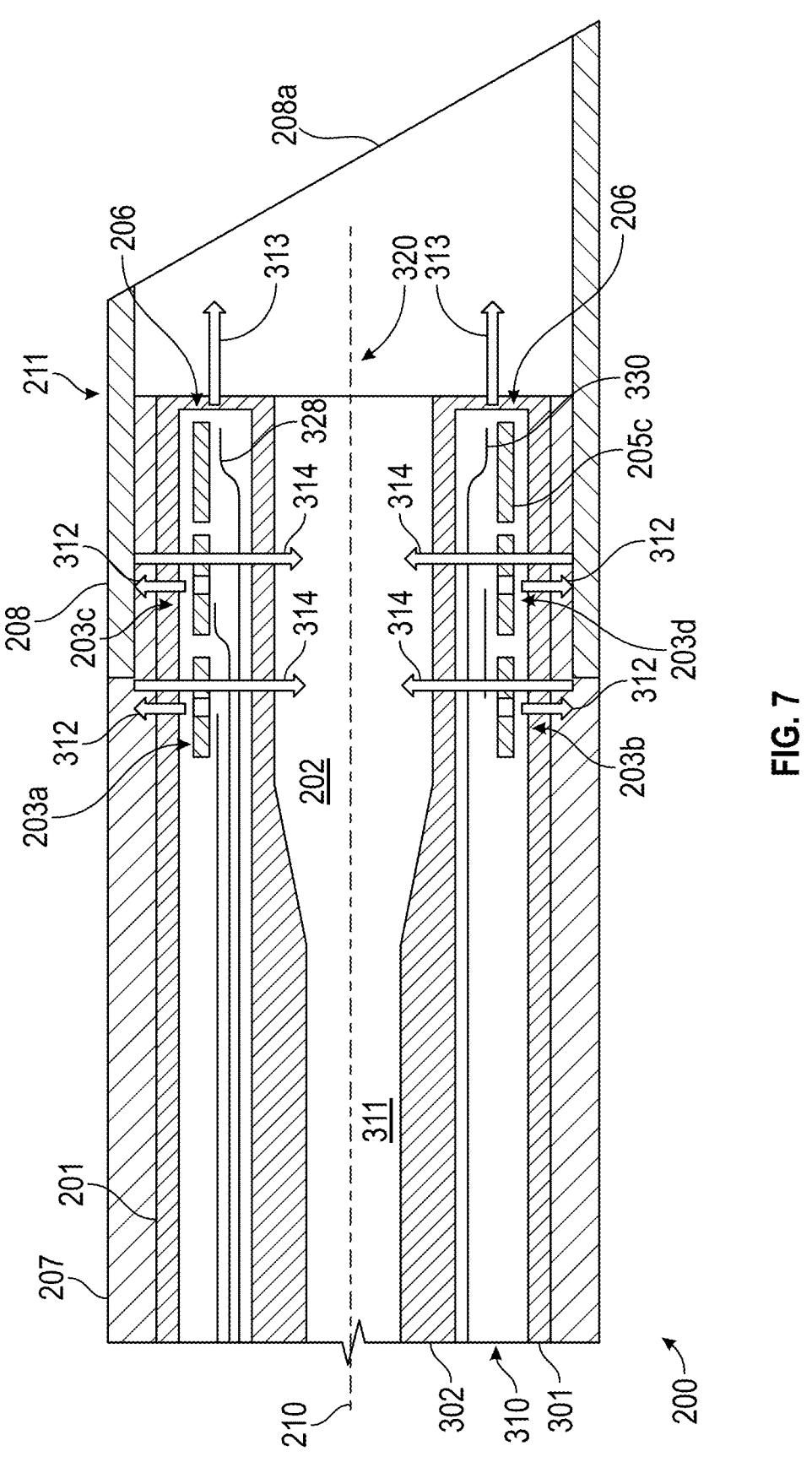
FIG. 7 illustrates internal detail of a distal portion of a catheter and the shield of FIGS. 6A-6C including a tapered distal end for cutting tissue, according to one or more aspects of the present disclosure.

FIG. 7 illustrates additional detail of a distal end of a catheter that may be used for the catheter of FIGS. 6A-6C. The catheter depicted in FIG. 7 may include any of the aspects described above with reference to FIGS. 3A-3C. A shield 208 included on the catheter depicted in FIG. 7 includes a tapered distal end 208*a*. The tapered distal end 208*a* may be used to cut or pierce tissue, such as fibrotic tissue or calcified tissue described above with reference to FIGS. 6A-6C. In some examples, the shield 208 and distal end 208*a* may be rotatable to enable more efficient modification (e.g., cutting) of tissue. The distal end 208*a* of shield 208 depicted in FIG. 7 may be used to cut away fibrotic tissue from a cardiac device lead (e.g., pacemaker lead) to assist with removing the lead from the body.

Figure 8:
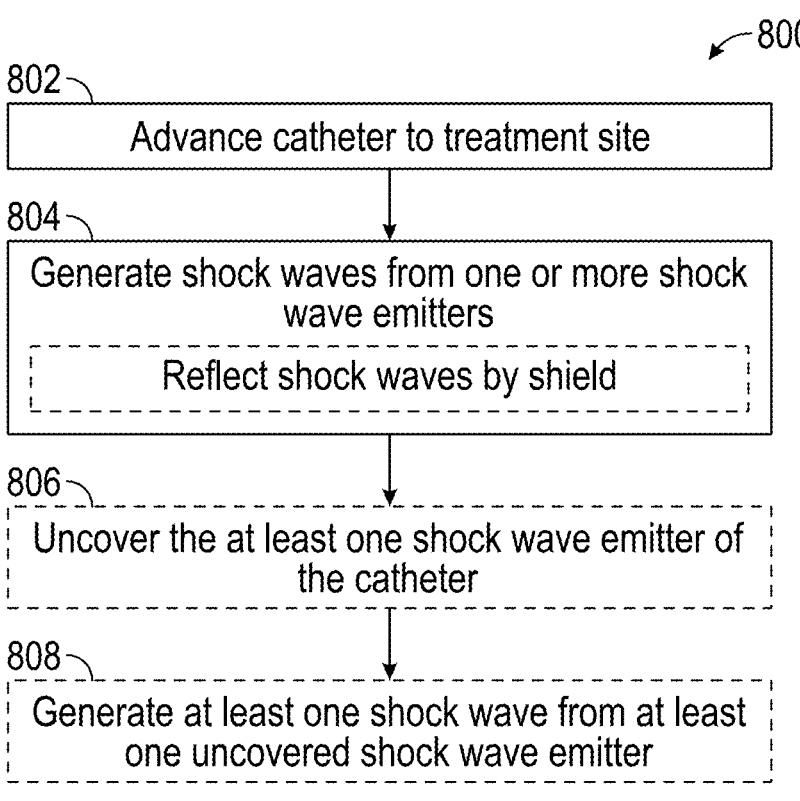
FIG. 8 is a diagram of an exemplary method for treating vascular occlusions, according to one or more aspects of the present disclosure.

FIG. 8 illustrates a method 800 for treating target material, such as calcifications or fibrotic tissue, in a body lumen. Method 800 may be performed by a shock wave catheter, such as catheter 10, 200, or 600. At step 802, the catheter is advanced to a treatment site, which can be a location of calcifications and/or fibrotic tissue in a body lumen, such as a blood vessel or heart chamber. The catheter may be advanced until a distal end of the catheter (e.g., distal end 211 of the catheter body 201) abuts the treatment site. For example, a user may advance the catheter until the catheter meets resistance that indicates that the catheter is abutting the calcification and/or fibrotic tissue.

At step 804, at least one shock wave emitter of the catheter is controlled to generate one or more shock waves to treat the target material. For example, with reference to FIG. 1, a user may activate shock wave power source 28 to provide energy to at least one shock wave emitter 18 to treat the stenotic lesion. The energy can be in the form of one or more voltage pulses that cause sparks to form across electrode pairs of the one or more emitters. Alternatively, the energy can be in the form of one or more laser pulses that are emitted from optical fibers of the one or more emitters.

Step 804 may include generating shock waves at one or more radially firing shock wave emitters while a shield of the catheter (e.g., shield 208 of catheter 200) is covering the one or more radially firing shock wave emitters such that the shock waves are reflected into a cavity at distal end of the catheter (e.g., cavity 202 of catheter 200). The shock waves may propagate in a distal direction to break up calcifications located in front of the distal end of the catheter and/or may break up calcifications that are located within the cavity at the distal end of the catheter. Step 804 may include generating shock waves at one or more forward firing shock wave emitters to treat calcified material located in front of the distal end of the catheter. Optionally, the forward firing shock wave emitters are used first to break up at least some of the calcification located in front of the catheter, the catheter is advance distally, and the radially firing shock wave emitters are used next (with the shield covering them) to break up material that has been pushed or drawn into the cavity at the distal end of the catheter. Once step 804 has resulted in breaking up at least some of the target material, the catheter may be moved distally to treat additional target material. For example, step 804 may result in "tunneling" into stenotic lesion such as depicted in FIG. 1. Optionally, a user applies steady pressure to the catheter in the distal direction so that as the shock waves break up the target material, the catheter advances distally, keeping a distal end abutting the target material.

Optionally, method 800 may include step 806 in which the shield covering the radially firing shock wave emitters is retracted, uncovering at least some of the radially firing shock wave emitters. This step can include retracting the shield fully so that all of the radially firing shock wave emitters are uncovered or partially so that some emitters are uncovered and others are not. Optionally, the shield has a tapered end, such as the tapered distal end 603 of shield 608 and is positioned so that a long side of the shield covers emitters located along that side of the catheter and the emitters on the other side are uncovered.

At step 808, the radially firing shock wave emitters are controlled to generate at least one shock wave. The at least one shock wave is emitted radially outwardly to break up calcifications located radially outwardly of the catheter. In examples in which a tapered shield covers only a portion of the shock wave emitters, shock waves generated by the covered shock wave emitters are reflected back toward the non-covered side of the catheter, concentrating the application of shock waves to that side of the catheter. This can be useful in treating non-concentric calcifications. With reference to FIG. 1, step 808 may be useful in treating stenotic material located radially outwardly of the catheter after step 804 has enabled the catheter to be advanced into the stenotic lesion.

One or more steps of method 800 may be repeated to treat a target area. Method 800 can include any number of other steps and steps may be performed in any order. In some examples, method 800 includes extending a tapered distal end of the shield to pierce into tissue.

Figure 9:
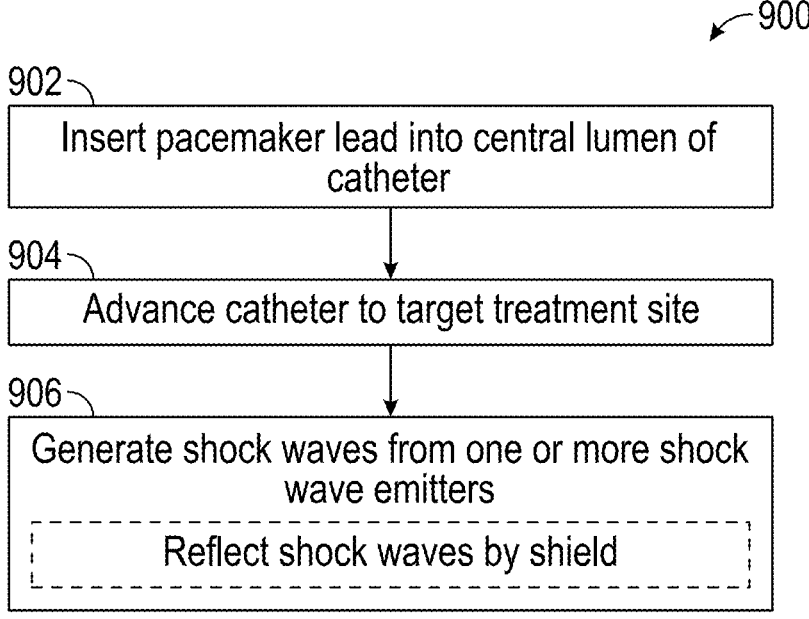
FIG. 9 is a diagram of an exemplary method for pacemaker lead removal, according to one or more aspects of the present disclosure.

As explained above, catheters according to the principles described herein can be used to facilitate removal of pacemaker leads, which often become encased in fibrotic tissue. FIG. 9 illustrates a method 900 for using a shock wave catheter for removing a pacemaker lead. Method 900 may be performed by any of the catheters described herein.

At step 902, a proximal end of a pacemaker lead is inserted into a central lumen of a shock wave catheter, such as through central lumen 311 of catheter 200. This may be done inside or outside of the body. At step 904, the catheter is advanced into and through vasculature of the body to the target treatment site in the heart, using the pacemaker lead as a guide. The target treatment site may be the location where the pacemaker lead anchors into the heart wall.

At step 906, one or more shock waves are generated by one or more shock wave emitters of the catheter. The one or more shock waves break up at least a portion of fibrotic tissue encasing the pacemaker lead. Step 906 can include using generating shock waves from one or more radially firing shock wave emitters while the one or more radially firing shock wave emitters are covered by a shield. The shock waves are reflected inwardly by the shield into a cavity located at the distal end of the catheter (e.g., cavity 202 of catheter 200). At least a portion of the fibrotic tissue encasing the pacemaker lead may be positioned ion the cavity, such as illustrated in FIG. 5B, and the inwardly reflected shock waves may impinge on the fibrotic tissue, breaking it up. Step 906 may include using one or more forward firing shock wave emitters to break up fibrotic tissue located in front of a distal end of the catheter.

Figures 10A, 10B:
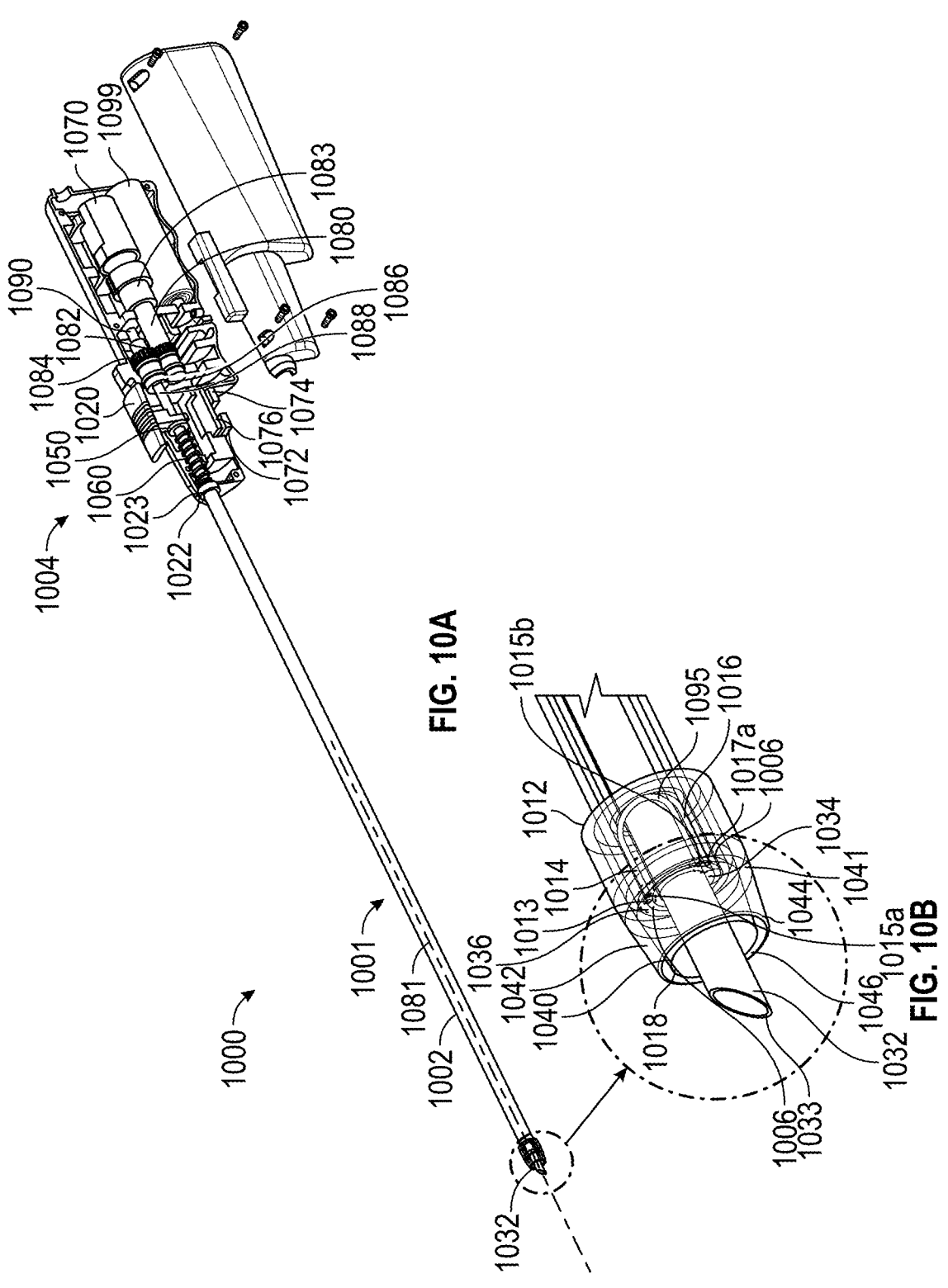
FIG. 10A illustrates an exemplary catheter including a motorized cutting mechanism in an extended position and one or more shock wave emitters according to some examples.
FIG. 10B illustrates a detail view of the distal end of the catheter of FIG. 2A in which the cutting mechanism is in an extended position according to some examples.

FIG. 10A illustrates an exemplary catheter 1000 that may be used as catheter 10 of FIG. 1 for treating lesions within a body lumen. Catheter 1000 includes a catheter body 1001, a cutting mechanism in the form of a rotatable tube 1032 positioned in a lumen 1034 of catheter body 1001, and at least one shock wave emitter 1006 positioned at a distal end of the catheter body. The at least one shock wave emitter 1006 can be used to generate shock waves for breaking up calcified and/or fibrotic tissues within body lumens, and the rotatable tube 1032 can be used to mechanically cut away the calcified and/or fibrotic tissues before, during, or after shock wave treatment, as described below.

FIG. 10B illustrates a detail view of the distal end of catheter 1000. As illustrated in the detail view of FIG. 10B, rotatable tube 1032 may include one or more cutting features at its distal end 1033 such that it can be used to cut away fibrotic and/or calcified tissue from a treatment area. Exemplary cutting features include, but are not limited to, a beveled end, a serrated end, a scalloped end, a double beveled end. Micro-serration may be provided along the cutting edge at distal end 1033 to increase sharpness and cutting efficiency. Carbide material may be integrated into the cutting edge at distal end 1033 to provide increased hardness and maintain sharpness for a longer duration. The cutting tip may be exposed to extremely low temperatures (Cryogenic Treatment) to enhance its hardness and wear resistance, resulting in a sharper, more durable edge. The rotatable tube 1032 can be translated relative to the catheter body 1001 between an extended position and a retracted position and can be rotated (e.g., in a counterclockwise or clockwise direction relative to a longitudinal axis 1081 of a lumen 1034 of catheter body 1001). When positioned in the extended position as shown in FIGS. 10A and 10B, the distal end 1033 of the rotatable tube 1032 is distal of a distal end 1036 of the catheter body 1001 such that the rotatable tube can be rotated to cut tissue located distally of the distal end of catheter 1000. In some embodiments, in addition to or instead of rotating, the distal cutting feature may be repeatedly moved axially (e.g., from the extended position to the retracted position) to repeatedly stab or slice and break up hardened or densified tissue.

The catheter body 1001 may include an elongate tube 1002 and a nozzle 1042. The nozzle 1042 may be located at the distal end 1036 of the elongate tube. In such examples, the distal end of the catheter body 1001 may be the distal end 1036 of the elongate tube. If the catheter body 1001 includes a nozzle 1042, the distal end of the catheter body may be the distal end 1046 of the of the nozzle 1042. In the extended position, the distal end 1033 of rotatable tube 1032 may be positioned distally of the distal end 1046 of the nozzle 1042. Thus, whether or not the catheter 1000 includes a nozzle, the distal end 1033 of rotatable tube 1032 can be translated such that it extends beyond the distal end of catheter body 1001 in order to cut away fibrotic and/or calcified tissue. When in the retracted position, the rotatable tube 1032 may be positioned such that its distal end 1033 is located proximally of the distal end 1036 of the catheter body 1001. The distal end 1033 of rotatable tube 1032 may additionally be positioned proximally of one or more shock wave emitters 1006 when in the retracted position such that the rotatable tube does not impact the manner and shape of distally propagating shock waves and/or bubbles.

Figures 10C, 10D:
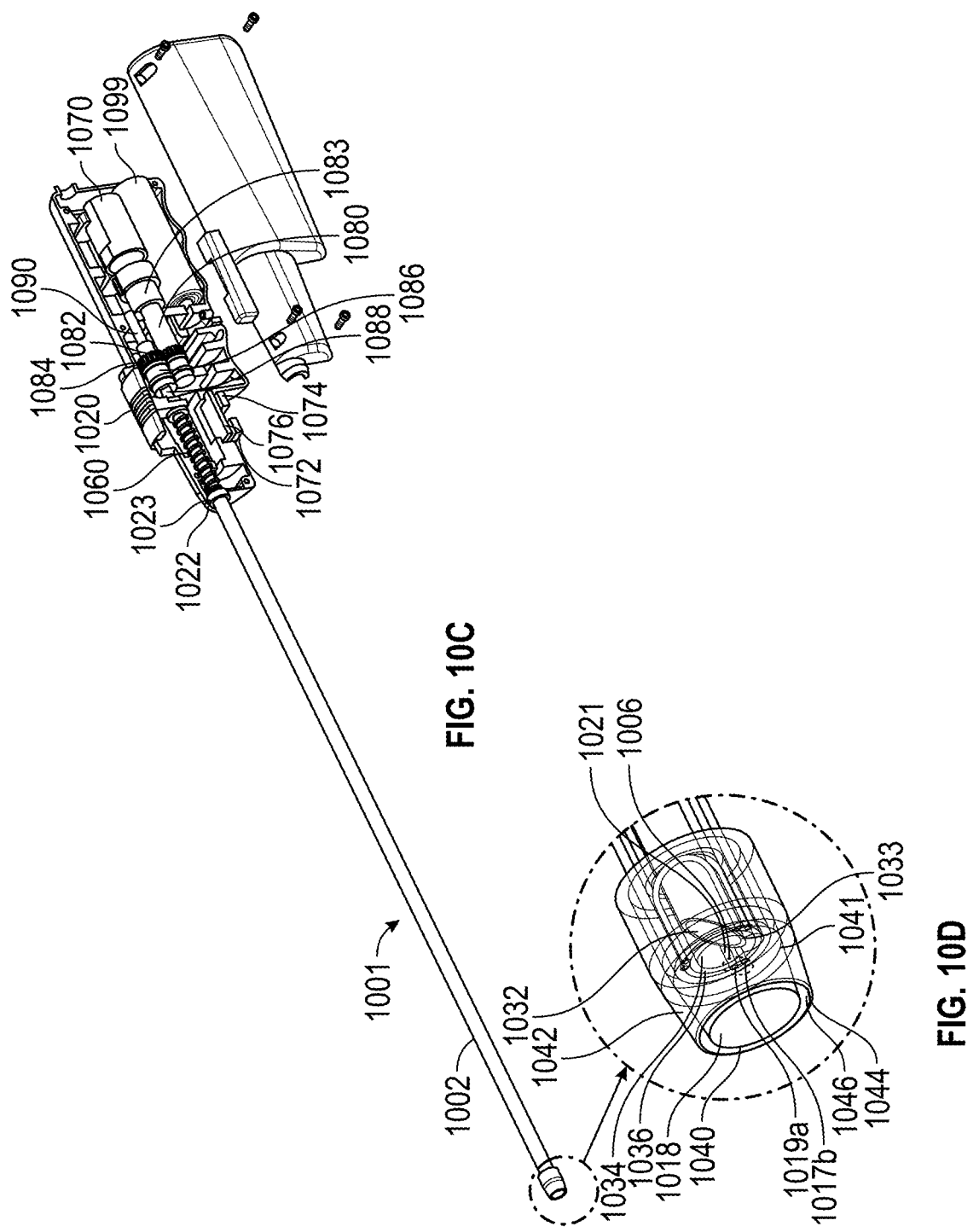
FIG. 10C illustrates the exemplary catheter of FIG. 2A in which the cutting mechanism is in a retracted position according to some examples.
FIG. 10D illustrates a detail view of the distal end of the catheter of FIG. 2C in which the cutting mechanism is in the retracted position according to some examples.

FIGS. 10A and 10C illustrate a handle 1004 that may be positioned at a proximal end of catheter 1000 and may include a plurality of components that can be used to control the rotatable tube 1032 (e.g., to translate and rotate the rotatable tube 1032). Handle 1004 is depicted in an exploded configuration in FIG. 10A to show the internal components of the handle 1004 while the rotatable tube 1032 is in the extended position. FIG. 10C illustrates an exploded view of handle 1004 depicting the internal components of the handle 1004 while the rotatable tube 1032 is in the retracted position, and FIG. 10D illustrates a detail view of the distal end of catheter 1000 when the rotatable tube 1032 is in the retracted position. The handle 1004 may include a user engagement 1020 for translating the rotatable tube 1032 to enable a user (e.g., a physician) using catheter 1000 can easily move the rotatable tube between a retracted position (shown in FIGS. 10C and 10D) and an extended position (shown in FIGS. 10A and 10B). Rotatable tube 1032 may be operatively connected to the user engagement 1020 (e.g., a slider or other user engagement) configured to enable a user to translate the rotatable tube 1032 relative to the catheter body 1001. A proximal end 1090 of the rotatable tube 1032 may extend into handle 1004 via an aperture 1022, and the user engagement 1020 may be connected to the rotatable tube 1032 by a flange 1050 mounted to rotatable tube 1032. In FIGS. 10A and 10B, the user engagement 1020 and proximal end 1090 of rotatable tube 1032 are in a distal position relative to the handle 1004 corresponding to the extended position of the rotatable tube. In FIGS. 10C and 10D, the user engagement 1020 and proximal end 1090 of rotatable tube 1032 are in a proximal position relative to handle 1004 corresponding to the retracted position of rotatable tube 1032.

The rotatable tube 1032 and user engagement 1020 may be biased toward the retracted position shown in FIGS. 10C and 10D (e.g., biased toward a proximal end of the catheter 1000) by a biasing member 1060 (e.g., a spring). The biasing member 1060 may be operatively connected to both the rotatable tube 1032 and the user engagement 1020 and may be configured to exert a biasing force against the rotatable tube 1032 and the user engagement 1020 such that the rotatable tube 1032 and the user engagement 1020 are biased in a proximal direction. A user can engage user engagement 1020 to move the rotatable tube 1032 between the retracted and extended positions (e.g., by exerting a force against, or in the same direction as, the biasing member 1060). When a user engages the user engagement 1020, for instance to slide the engagement 1020 distally relative to the catheter body 1001 and handle 1004, the rotatable tube 1032 may translate to the extended position depicted in FIGS. 10A and 10B. When a user releases the user engagement 1020, the rotatable tube 1032 may be pushed proximally to the retracted position by biasing member 1060. It should be understood, however, that a user could alternatively move the user engagement 1020 proximally to translate the rotatable tube 1032 to the retracted position depicted in FIGS. 10C and 10D.

As shown in FIG. 10A, biasing member 1060 is compressed against a radial bearing 1023 when the rotatable tube 1032 is in the extended position. The radial bearing 1023 may enable a user to easily rotate the rotatable tube 1032. Biasing member 1060 be fixed on one end to radial bearing 1023. The biasing member may be operatively connected to the rotatable tube 1032 on its other end as described above. When a user releases user engagement 1020, biasing member 1060 is uncompressed (e.g., releases stored energy) to return the rotatable tube to the retracted position depicted in FIG. 10C. It should be understood that while the terms "compresses" and "uncompress" are used herein with reference to biasing member 1060, this is for exemplary purposes only. Biasing member 1060 may be configured to store and release energy in any manner such that the rotatable tube is biased toward the retracted position. Additionally, while the catheters described herein include a manually slidable user engagement 1020 for extending and retracting rotatable tube 1032, it should be understood that catheter 1000 may include an actuator for powered extension and/or retraction of the rotatable tube 1032. The actuator may be driven electrically, pneumatic, or hydraulically. The actuator may be a linear actuator or a rotary actuator.

The rotatable tube 1032 may also be operatively connected to a user-operable rotational component 1070 such that the rotatable tube can be rotated to cut fibrotic and/or calcified tissue inside a body lumen. The user-operable rotational component 1070 may be a motor configured to rotatably drive the rotatable tube 1032. Although, in some examples, the user-operable rotational component 1070 may be a manually engageable rotational component, as discussed further below with reference to FIGS. 3A and 3B. The rotational component 1070 may be operatively connected to the rotatable tube 1032 by a gear train, which may be included in housing 1083. The gear train may be configured to step down rotational speed and/or increase torque from the rotational component 1070. In some examples, a first gear 1082 may be positioned on a shaft 1080 (e.g., motor shaft) connected to user-operable rotational component 1070. A second gear 1084 may be connected to rotatable tube 1032. Gear 1082 and gear 1084 may be configured to interface such that when a user engages user-operable rotational component 1070, gear 1082 rotates and induces rotational movement of gear 1084. Gear 1084 may be connected to the rotatable tube 1032 by a shaft key and keyway interface. Gear 1084 may include a keyway 1086 configured to interlock with a key shaft 1088 connected to the rotatable tube such that gear 1084 and rotatable tube 1032 rotate together.

As noted above, the user-operable rotational component 1070 can include a motor. The motor may be a DC gear motor with a maximum torque of 2 Newton meters (Nm) and a maximum rotation of two hundred and eighty rotations per minute (280 RPM). In some examples, the motor may have a maximum torque of at least one Newton meter (1 Nm), at least one and one-half Newton meters (1.5 Nm), at least two Newton meters (2 Nm), at least two and one-half Newton meters (2.5 Nm) and or at least three Newton meters (3 Nm). In some examples, the motor may have a maximum rotational velocity of at least two hundred rotations per minute (200 RPM), at least two hundred and fifty rotations per minute (250 RPM), at least three hundred rotations per minute (300 RPM), and/or at least three hundred and fifty rotations per minute (350 RPM).

The handle 1004 may house one or more batteries for powering the motor. The one or more batteries may include one or more rechargeable batteries 1099, such as one or more rechargeable lithium batteries. The battery 1099 may be connected to a charging circuit that includes a charging port such as a micro-USB charging port or other charging port positioned on the handle 1004. In some examples, the user-operable rotational component 1070 may be powered by an external power source such as an external generator or battery. For instance, user-operable rotational component 1070 may be connected to the same power source (e.g., power source 28 of FIG. 1) used for shock wave generation.

The handle 1004 may include one or more user engagements for activating the user-operable rotational component 1070. The illustrated example includes a first user engagement (e.g., engagement 1072) that may be engaged to rotate the rotatable tube 1032 in a first direction and a second user engagement (e.g., engagement 1074) that may be engaged to rotate the rotatable tube 1032 in a second direction. For instance, engagement 1072 may cause user-operable rotational component 1070 to rotate in a first direction, thus causing rotatable tube 1032 to rotate in a first direction. Engagement 1074 may cause user-operable rotational component 1070 to rotate in a second direction, thus causing rotatable tube 1032 to rotate in a second direction. The user engagements 1072 and 1074 may be connected to a control circuit (e.g., an analog control circuit and/or digital controller) that controls rotational component 1070 based on user inputs received via engagements 1072 and/or 1074.

The rotatable tube 1032 may be formed from a biocompatible material such as stainless steel, Titanium alloy, and/or Nitinol. Stainless steel may be advantageous due to its strength, durability, and resistance to corrosion. Titanium alloy may be advantageous for its excellent biocompatibility, strength, and resistance to corrosion. Nitinol may be advantageous for its shape memory and super elastic properties. In some examples, the rotatable tube is configured to extend at least five millimeters (5 mm), at least ten millimeters (10 mm), at least fifteen millimeters (15 mm), at least twenty millimeters (20 mm), at least twenty-five millimeters (25 mm), or at least thirty millimeters (30 mm) from the distal end of the catheter body 1001. As discussed above, the distal end of the catheter body 1001 may be the distal end of elongate tube 1002 or the distal end 1046 of nozzle 1042.

The rotatable tube 1032 may include an outer diameter that is smaller than an inner diameter of lumen 1034 of catheter body 1001. In some examples, an outer diameter of the rotatable tube may be 0.12 inches and an inner diameter of the rotatable tube 1032 may be 0.10 inches. In some examples, the outer diameter of the rotatable tube 1032 may be 0.109 inches and the inner diameter of the rotatable tube may be 0.09 inches. In some examples, the outer diameter of rotatable tube 1032 is between 0.10 inches and 0.13 inches. In some examples, the outer diameter of rotatable tube 1032 is at most 0.20 inches, at most 0.15 inches, at most 0.10 inches, and/or at most 0.075 inches. In some examples, the outer diameter of rotatable tube 1032 is at least 0.075 inches, at least 0.10 inches, at least 0.15 inches, and/or at least 0.20 inches. The inner diameter of rotatable tube 1032 is between 0.085 inches and 0.095 inches. In some examples, the inner diameter of rotatable tube 1032 is at least 0.075 inches, at least 0.080 inches, at least 0.085 inches, at least 0.090 inches, at least 0.095 inches, at least 0.10 inches, at least 0.105 inches, and/or at least 0.11 inches. In some examples, the inner diameter of rotatable tube 1032 is at most 0.075 inches, at most 0.080 inches, at most 0.085 inches, at most 0.090 inches, at most 0.095 inches, at most 0.10 inches, at most 0.105 inches, and/or at most 0.11 inches.

Typical pacemaker lead diameters range from approximately 5 French (1.7 millimeters) to 7 French (2.3 millimeters), varying by type, model, and manufacturer. The inner diameter of the rotatable tube 1032 may be sized slightly larger than a typical pacemaker lead diameter. The inner diameter of the rotatable tube 1032 may be at least 1.8 millimeters, at least 1.9 millimeters, at least 2.0 millimeters, at least 2.1 millimeters, at least 2.2 millimeters, at least 2.3 millimeters, at least 2.4 millimeters, at least 2.5 millimeters, at least 3.0 millimeters, or any value therebetween.

Also shown in FIGS. 10A-10D are shock wave emitters positioned at a distal end of catheter 1000 that may be used to break up and/or dislodge calcified and/or fibrotic tissues before, during, or after using rotatable tube 1032 to cut the tissue (e.g., both the shock wave emitters and the rotatable tube may be used to remove the tissue from a pacemaker lead). At least one shock wave emitter 1006 may be disposed proximate a distal end 1036 of the catheter body 1001 and configured to generate at least one shock wave that propagates distally of the catheter body 1001. The at least one shock wave emitter 1006 may include a pair of electrodes separated by a spark gap. In some examples, a plurality of shock wave emitters 1006 may be positioned proximate the distal end 1036 of the catheter body 1001. At least one of the plurality of shock wave emitters 1006 may be electrically connected with at least one other shock wave emitter 1006 such that applying a voltage pulse across an electrode connected to a positive terminal at a first shock wave emitter 1006 and an electrode connected to a negative terminal at a second shock wave emitter 1006 causes each of the two emitters 1006 to generate a respective shock wave. In some examples, at least one of the plurality of shock wave emitters may be configured to generate shock waves independently of at least one other shock wave emitter, as described below.

A first shock wave emitter 1006 of the plurality of shock wave emitters may include a distal end 1013 of a first insulated wire 1012. The insulated wire 1012 may extend along the length of the catheter body 1001 from the distal end 1036 of the catheter body 1001 (e.g., so that it can be connected to a voltage source proximally of the distal end). A second insulated wire 1014 may extend from the first shock wave emitter 1006 to a second shock wave emitter 1006. The second insulated wire includes a first exposed distal end 1015a forming an electrode pair with distal end 1013 of the first insulated wire 1012 separated by a spark gap, thus forming the first shock wave emitter 1006, and a second exposed distal tip 1015b forming part of an electrode pair at the second shock wave emitter 1006, as described below. As used herein, an "exposed end," "exposed tip," and/or "exposed distal end" of an insulated wire may refer to a portion of the wire from which the insulation has been removed, thus revealing a portion of the conductive wire. However, while the emitters herein are described as including the exposed distal ends/tips of insulated wires, it should be understood that any suitable conductor may serve as an electrode of the emitters.

The second insulated wire 1014 extends proximally from the first shock wave emitter 1006 into the catheter body 1001 for a first distance, and loops around, for instance as illustrated by the bend 1095 forming the U-shaped portion of insulated wire 1014, to extend distally toward the second shock wave emitter 1006. A third insulated wire 1016 includes a first exposed distal end 1017a at the third shock wave emitter 1008. The second exposed distal end 1015b of second insulated wire 1014 and first exposed distal end 1017b of the third insulated wire 1016 form an electrode pair separated by a spark gap, thus forming the second shock wave emitter 1006. The third insulated wire 1016 extends from the second shock wave emitter 1006 to a third shock wave emitter 1006 (shown in FIG. 10D). Similar to the second insulated wire 1014, the third insulated wire 1016 extends proximally into the catheter body 1001 for a first distance, and loops around to extend distally toward the third shock wave emitter 1006. The third insulated wire 1016 includes a second exposed distal end 1017b (shown in FIG. 10D) at the third shock wave emitter 1006, forming an electrode pair with exposed distal end 1019a of a fourth insulated wire 1021. The exposed distal ends of the third and fourth wire form another electrode pair separated by a spark gap, thus forming the third shock wave emitter 1006. The fourth insulated wire 1021 extends proximally into the catheter body 1001 and along the length of the catheter body from the distal end 1036 to connect to a positive terminal of a voltage source. Accordingly, when a voltage is applied across the first insulated wire 1012 connected to the negative terminal of the voltage source and the fourth insulated wire 1021 connected to the positive terminal of the voltage source, a plurality of shock waves is generated as an electrical current traverses the spark gaps separating the exposed distal tips of each insulated wire at shock wave emitters 1006. The shock wave emitters 1006 may be arranged evenly or unevenly around the longitudinal axis 1081 of catheter 1000.

The shock wave emitters 1006 of the catheter 1000 shown in FIG. 10B are electrically connected in series such that an electrical pulse applied across insulated wires connected to negative and positive terminals of a voltage source, respectively, causes each of the plurality of shock wave emitters 1006 to emit at least one respective shock wave. In some examples, at least one first shock wave emitter of a plurality of shock wave emitters can be driven independently of at least a second shock wave emitter of the plurality of shock wave emitters. Accordingly, in some examples, rather than extending wires between all of the shock wave emitters such that applying a single voltage pulse causes each of the shock wave emitters to generate shock waves in series, one or more shock wave emitters can each include an electrode pair configured to generate shock waves independently of the other shock wave emitters. In some examples, the electrode pair at each shock wave emitter 1006 can be formed of the exposed distal ends of a first and second wire that each extend along the length of catheter 1000 from the distal end of the catheter body 1001 to electrically couple to a respective positive and negative terminal (or to ground) of a voltage source (e.g., each shock wave emitter may be connected to a respective channel of a relay such that it can be driven independently of the other emitters). In such examples, when a voltage pulse is applied across the first and second wire of an independently driven shock wave emitter, a current flows from an exposed distal tip of the first insulated wire to the exposed distal tip of the second insulted wire to generate a shock wave, but that shock wave emitter is electrically isolated from the remaining shock wave emitters.

In some examples, catheter body 1001 includes a plurality of lumens (e.g., in addition to central lumen 1034) extending within the catheter body. In some examples, one or more of the insulated wires (e.g., wire 1012) extend along the length of the catheter 1000 within a respective lumen to connect to a voltage source. As described above, other insulated wires (e.g., wire 1014) are routed between respective shock wave emitters to carry the current received from the voltage between each of the emitters. Accordingly, the wires routed between respective shock wave emitters may extend into a first lumen or first portion of a lumen of the catheter body 1001 in a first direction toward a first shock wave emitter and extend into a second lumen or second portion of a lumen in a second direction toward a second shock wave emitter.

In some examples, a nozzle may be positioned at the distal end of catheter body 1001 to concentrate shock waves and/or bubbles generated using shock wave emitter(s) 1006. Nozzle 1042 may be configured such that shock waves generated by shock wave emitter(s) 1006 propagate toward an outlet 1040 of the nozzle 1042. The nozzle 1042 may be configured to concentrate the at least one shock wave generated by shock wave emitter(s) 1006 at the outlet 1040 of the nozzle. For instance, the nozzle 1042 may be a convergent nozzle (e.g., may include an outlet 1040 that has a smaller diameter than its inlet). The nozzle may be configured such that shock waves directed into the nozzle are reflected by the nozzle wall 1018. The shock waves may continue to propagate forward (e.g., distally) within the nozzle 1042 as they reflect from converging walls of the nozzle, reaching a peak concentration at an outlet of the nozzle before propagating distally of the catheter through the nozzle outlet. Thus, shock waves propagating within the nozzle may cause a fluid within the nozzle to move toward the nozzle outlet, increasing in pressure and velocity as it propagates within the nozzle toward the outlet. The fluid may exit via the nozzle outlet and project forward toward a target treatment area.

In some examples, one or more bubbles may be generated as a result of the shock wave generation process. Nozzle 1042 may be configured to direct at least one bubble to the outlet of the nozzle. The nozzle 1042 may be configured to concentrate the at least one bubble at the outlet 1040 of the nozzle such that the at least one bubble propagates distally of the outlet 1020. Although other forward-directed IVL shock wave generating devices (e.g., devices with emitters that produce primarily distally propagating shock waves) without a nozzle also produce bubbles during the shock wave generation process, those bubbles may collapse shortly after formation. The nozzle 1042 may enable the concentrated bubble(s) to propagate further toward a target treatment area. The collapse of the bubble(s) at or near the treatment area may enhance the effect of forces produced via the collapse on breaking up calcifications, fibrotic tissue, or other lesions.

In some examples, a diameter of the nozzle outlet 1040 may be at least as large as a central lumen 1034 extending along the length of catheter body 1001 such that the rotatable tube 1032 can extend through the nozzle and beyond the nozzle outlet 1040 when in the extended position and/or such that a guidewire can extend through the nozzle 1042 and beyond the nozzle outlet 1040. When the rotatable tube 1032 is in the extended position, a pacemaker lead may be received directly into the rotatable tube 1032. When the rotatable tube 1032 is in the retracted position, a pacemaker lead may first be received into the nozzle outlet 1040 and then into the rotatable tube 1032.

The outer edge 1044 of nozzle 1042 may be rounded or flattened to provide a protective surface for tissues as the catheter is navigated through a body lumen. Thus, the nozzle 1042 can be safely navigated through a body lumen while the rotatable tube 1032 is retracted, and, upon reaching a target treatment site, the rotatable tube 1032 can be extended distally beyond the nozzle outlet 1040 to cut away fibrotic and/or calcified tissue. Nozzle 1042 may be configured such that its widest diameter is sufficiently narrow to navigate through vasculature. In some examples, the widest diameter of nozzle wall 1018 may be wider than an outer diameter of the catheter body 1001, for instance, as shown in FIGS. 10A and 10B where the nozzle 1042 is positioned such that a portion of the catheter body 1001 is interior to the nozzle 1042. In some examples, however, the widest diameter of nozzle 1042 may be flush with an outer diameter of the catheter body 1001.

In some examples, the nozzle may be positioned such that shock waves emitted from shock wave emitter(s) 1006 are formed within an interior space of nozzle 1042. The nozzle may be configured such that the shock waves are formed near an inlet 1041 of the nozzle and propagate toward an outlet 1040 distally of the inlet 1041 of the nozzle 1042. Nozzle 1042 may configured such that shock wave emitter(s) 1006 are positioned radially inward of an outer diameter of an inlet 1041 to the nozzle. Positioning the emitter(s) 1006 radially inward of the nozzle inlet 1041 ensures that any radially biased portion of the shock waves will reflect inwardly of nozzle 1042 as they propagate away from the distal end of catheter body 1001.

Nozzle 1042 may be formed at least in part of an acoustically reflective and biocompatible material. For instance, nozzle 1042 may include medical-grade plastics, steel, or other non-reactive materials. Nozzle 1042 may be formed from stainless steel, high-density polyethylene, polyvinyl chloride, or a combination thereof. Stainless steel may be preferred in some examples due to its ability to capture and thrust forward all shock waves generated by the emitters, while also exhibiting less attenuation of energy compared to plastic alternatives. In some examples, the distal end of catheter body 1001 is also formed of an acoustically reflective material such that any proximally propagating portion of shock waves generated by emitter(s) 1006 are reflected into nozzle 1042. In some examples, the nozzle 1042 may be attached to a distal end of a catheter by cutting slits into a proximal end of the nozzle, compressing the portions separated by the slits over the distal end of the catheter, and using a laser welder to weld the slits together on the distal end of the nozzle.

Figure 11:
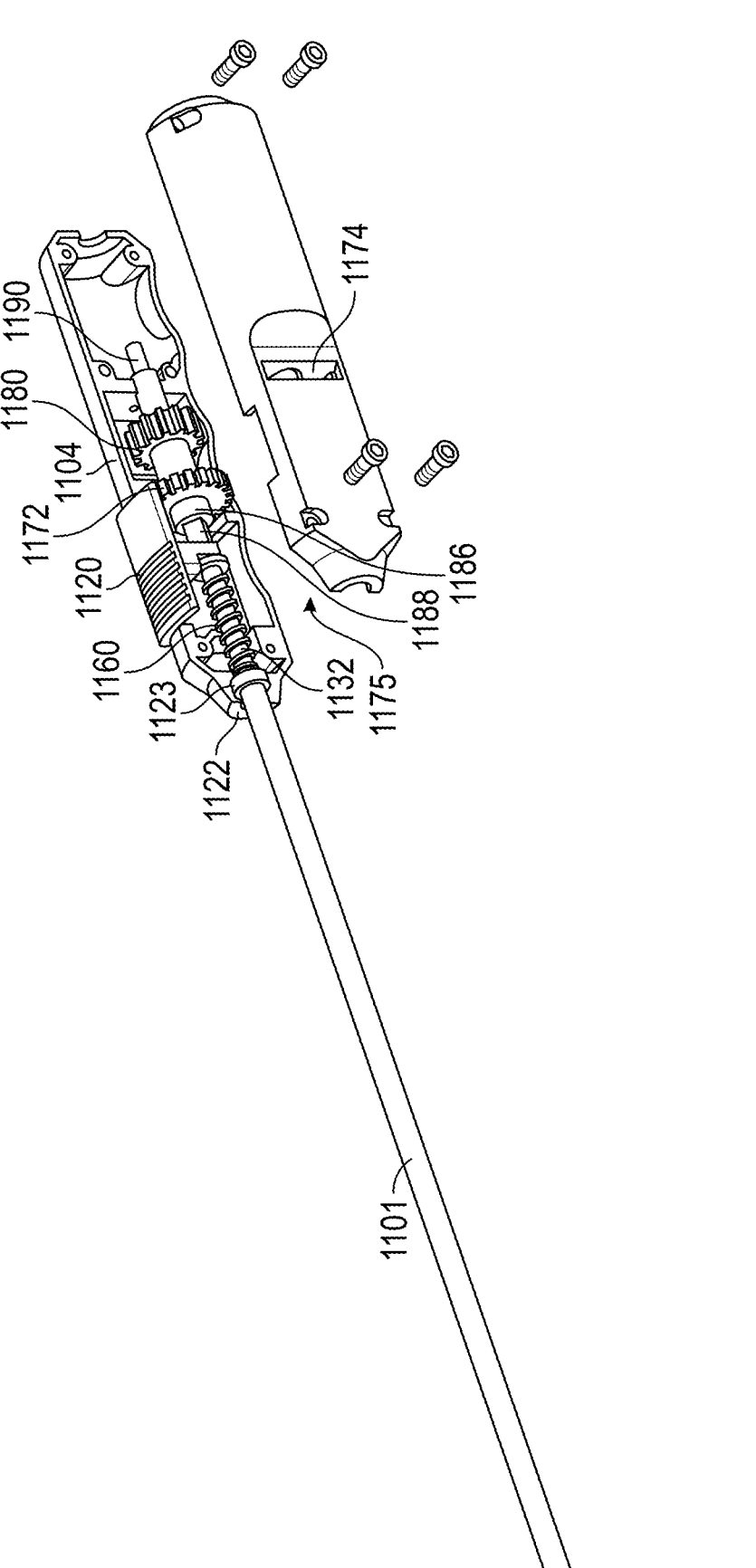
FIG. 11 illustrates an exemplary catheter including a manually operated cutting mechanism in an extended position and one or more shock wave emitters according to some examples.

FIG. 11 illustrates another exemplary catheter 1100 that may be used as the catheter 10 in FIG. 1. Catheter 1100 includes a cutting mechanism that can be operated manually by a user, as described in further detail below. Rotatable tube 1132 (which may include any of the features of rotatable tube 1032 of FIGS. 10A-10D) may be operatively connected to a user-engageable rotational component 1172 such that the rotatable tube can be rotated to cut fibrotic and/or calcified tissue inside a body lumen. User-engageable rotational component 1172 may be a wheel or gear that a user can manually turn to rotate rotatable tube 1132. User-engageable rotational component 1172 may include a plurality of gear teeth to provide an enhanced grip for a user relative to a smooth wheel. Catheter 1100 may include a handle 1104 and the user-engageable rotational component 1172 may be partially enclosed within the handle 1104. Handle 1104 may include a slot 1174 configured such that a portion of user-engageable rotational component 1172 extends through the slot to be exposed outside of the handle 1104 enabling a user to access and rotate the user-engageable rotational component 1172. User-engageable rotational component 1172 may be connected to the rotatable tube 1132 by a shaft key and keyway interface. User-engageable rotational component 1172 may include a keyway 1186 configured to interlock with a key shaft 1188 connected to the rotatable tube such that user-engageable rotational component 1172 and rotatable tube 1132 rotate together. User engageable rotational component may be connected to an indexing component used for indexing during rotation.

The handle 1104 may include a user engagement 1120 for translating the rotatable tube 1132 such that a user (e.g., a physician) using catheter 1100 can move the rotatable tube between a retracted position (shown in FIG. 10D) and an extended position (shown in FIG. 10B). As shown, rotatable tube 1132 may be operatively connected to the user engagement 1120 (e.g., a slider or other user engagement) configured to enable a user to translate the rotatable tube 1132 relative to the catheter body 1101. A proximal end 1190 of the rotatable tube 1132 may extend into handle 1104 via an aperture 1122, and the user engagement 1120 may be connected to the rotatable tube 1132 by flanges 1150 mounted to rotatable tube 1132.

The rotatable tube 1132 and user engagement 1120 may be biased toward the retracted position described above with reference to the configuration shown in FIGS. 10C and 10D (e.g., biased toward a proximal end of the catheter 1100) by a biasing member 1160 (e.g., a spring). The biasing member 1160 may be operatively connected to both the rotatable tube 1132 and the user engagement 1120 and may be configured to exert a biasing force against the rotatable tube 1132 and the user engagement 1120 such that the rotatable tube 1132 and the user engagement 1120 are biased toward a proximal end of the catheter 1100. A user can engage user engagement 1120 to move the rotatable tube 1132 between the retracted and extended positions (e.g., by exerting a force against or with the biasing member 1160). When a user engages the user engagement 1120, for instance to slide the engagement 1120 distally relative to the catheter body 1101 and handle 1104, the rotatable tube 1132 may translate to the extended position depicted in FIGS. 10A and 10B. As with biasing member 1060 of catheter 1000 above, when a user releases user engagement 1120 from the extended position, biasing member 1160 automatically releases stored energy to push the rotatable tube 1132 proximally, returning the rotatable tube 1132 to the retracted position. It should be understood, however, that a user could alternatively move the user engagement 1120 proximally to translate the rotatable tube 1132 to the retracted position depicted in FIGS. 10C and 10D.

The biasing member 1160 is compressed against a radial bearing 1123 when the rotatable tube is in the extended position. Biasing member 1160 be fixed on one end to radial bearing 1123. The biasing member may be operatively connected to the rotatable tube 1132 on its other end. When a user releases user engagement 1120, biasing member 1160 uncompresses (e.g., releases stored energy) to return the rotatable tube to the retracted position. It should be understood that while "compresses" and "uncompresses" are used herein with reference to biasing member 1160, this is for exemplary purposes only. Biasing member 1160 may be configured to store and release energy in any manner so the rotatable tube 1132 is biased toward the retracted position.

Any of the catheters described above may be used to treat lesions (e.g., calcified tissues, fibrotic tissues, occlusions, etc. in the vasculature, urinary tract, or other body lumens).

In some examples, the catheters described herein may be particularly useful for removing pacemaker leads. Fibrotic tissue can build up around pacemaker leads, making the leads difficult to extract. The rotatable tube 1032 may be particularly useful for removing tissue from such pacemaker leads encapsulated in fibrotic and/or calcified tissue optionally in combination with the one or more shock wave emitters 1006. For instance, the rotatable tube 1032 of catheter 1000 and/or 1132 of 1100 may be configured to receive a guidewire at a proximal end of the catheter (e.g., proximally of the distal end 1036 of catheter 1000) and exit the catheter via rotatable tube 1032 at the distal end 1033 of rotatable tube 1032. The guidewire can be used to guide the catheter toward a target treatment site within a body lumen such as a site within the vasculature where a pacemaker lead is positioned. Upon reaching the target treatment site, the guidewire can be removed from rotatable tube 1032 and a pacemaker lead wire can be received into the catheter (e.g., catheter 1000 or 1100). The pacemaker lead may be received first via the nozzle outlet 1040 and/or central lumen 1034 of the catheter. The rotatable tube may be kept in its retracted position while one or more shock waves are generated to loosen tissue attached to and/or surrounding the pacemaker lead. When a pacemaker lead is positioned at least partially within the nozzle 1042 (e.g., via its outlet 1040), shock waves may be generated that are concentrated at the outlet and impinge on a portion of the pacemaker lead, for instance, to dislodge tissue attached to the pacemaker lead. In some examples, a guidewire is not used. A cardiac device lead (e.g., pacemaker lead may be received into the distal end of the catheter (e.g., catheter 1000 or 1100). The pacemaker lead may be received first via the nozzle outlet 1040 and/or central lumen 1034 of the catheter, and the catheter may be advanced along the pacemaker lead within the body to a target treatment site.

In some examples, the at least one shock wave emitter 1006 may be positioned radially outward of the rotatable tube 1032. If one or more shock waves are generated while the rotatable tube 1032 is positioned in the extended position, the shock waves may propagate around the rotatable tube, reflecting off the outer surface of the tube. In some examples, such as when the tube is positioned within a nozzle such as nozzle 1042, the nozzle may direct the one or more shock waves toward a distal end of rotatable tube 1032 so the shock waves are concentrated at or near the distal end 1033 of rotatable tube 1032. Thus, if a pacemaker lead is inserted into the rotatable tube 1032 while the rotatable tube is in the extended position, when one or more shock waves are generated and concentrated at or near the end of rotatable tube 1032, the one or more shock waves may impinge on the pacemaker lead near the distal end of the rotatable tube to dislodge fibrotic and/or calcified tissue on the pacemaker lead. After generating one or more shock waves, the rotatable tube 1032 may be moved to the extended position. The pacemaker lead may be received into the rotatable tube via its sharpened distal end, and a user may rotate rotatable tube 1032 to cut away the tissue attached to and/or surrounding the pacemaker lead.

Figure 12:
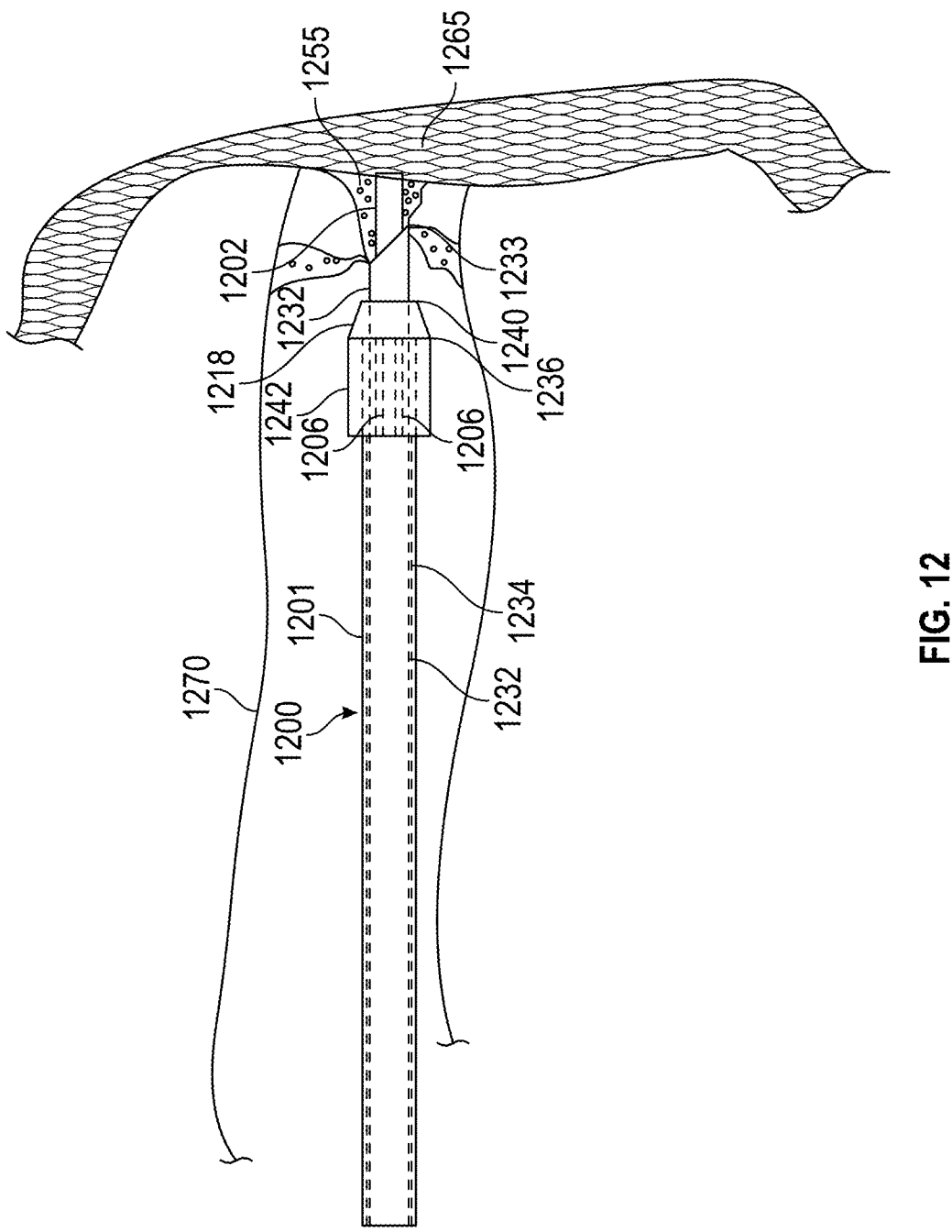
FIG. 12 illustrates an exemplary catheter including a cutting mechanism and one or more shock wave emitters within a body lumen according to some examples.

FIG. 12 illustrates an exemplary catheter 1200 that may include any one or more of the features of the catheters described above. Catheter 1200 is positioned within a body lumen 1270 such that a pacemaker lead 1202 is received into a cutting mechanism 1232 of catheter 1200. The pacemaker lead 1202 is lodged in cardiac tissue 1265 and at least partially encased in fibrotic and/or calcified tissue 1255. The cutting mechanism 1232 may be used to cut away or otherwise modify the fibrotic and/or calcified tissue 1255 such that the pacemaker lead 1202 can be more easily removed from lumen 1270.

Cutting mechanism 1232 may include a rotatable tube 1232 extending within a lumen 1234 along the length of the catheter body 1201. A distal portion of rotatable tube 1232 is positioned within an interior of a nozzle 1242, and a distal end 1233 of the rotatable tube 1232 extends beyond an outlet 1240 of the nozzle 1242 when the rotatable tube 1232 is in an extended position as described throughout this disclosure. Catheter 1200 also includes at least one shock wave emitter 1206 configured to generate shock waves that propagate within nozzle 1242. The shock waves are reflected off a nozzle wall 1218 as they propagate distally within nozzle 1242 and are concentrated at outlet 1240 (as described in detail above). The rotatable tube 1232 and shock wave emitter(s) 1206 may both be used to break up, loosen, or otherwise remove fibrotic and/or calcified tissue 1255 from the pacemaker lead 1202 such that the pacemaker lead 1202 can be efficiently and safely removed from the body.

In use, the catheter 1200 can be positioned within the body lumen 1270 adjacent to a target treatment site. Rotatable tube 1232 may be initially positioned in a retracted position such that its distal end 1233 is proximal of a distal end 1236 of the catheter body 1201. Upon positioning the catheter 1200 adjacent to the target treatment site (e.g., so that the pacemaker lead is received into outlet 1240 of nozzle 1242) one or more shock waves may be generated using shock wave emitter(s) 1206. The shock waves may loosen the fibrotic and/or calcified tissue 1255 from pacemaker lead 1202. Following shock wave treatment, the rotatable tube 1232 may be moved into the extended position (shown in FIG. 12) such that its distal end 1233 is positioned distally of the distal end 1236 of catheter body 1201 and distally of nozzle outlet 1240 and such that pacemaker lead 1202 is received into the distal end 1233 of the rotatable tube 1232, as shown. The rotatable tube 1232 may be rotated to cut away the tissue buildup to free the pacemaker lead 1202.

FIG. 13 illustrates an exemplary method 1300 for removing tissue from a pacemaker lead to remove the pacemaker lead from a body lumen. Any of the catheters described herein may be used to perform method 1300. At block 1302, the method 1300 may include advancing a catheter (e.g., catheter 10, 1000, 1100, or 1200) over a lead for a cardiac device (e.g., a pacemaker, a Vagus Nerve Stimulator) within a body lumen to a target treatment site, for instance, as shown in FIG. 4. The target treatment site may be an area of tissue buildup around the pacemaker lead (or other cardiac device lead) within the body lumen. To deliver the catheter to the target treatment site, an end of the pacemaker lead may be received into the catheter via an opening in the distal end of the catheter. The pacemaker lead may be received into a central lumen of the catheter extending along the length of the catheter body. The pacemaker lead may be received via a nozzle outlet and then into a central lumen extending along the length of the catheter body as the catheter is advanced within the body lumen. A cutting mechanism, such as the rotatable tube described throughout, may be positioned within the central lumen and the pacemaker lead may be received into the rotatable tube. The catheter may be advanced along the pacemaker lead until the catheter's movement is impeded by tissue buildup on or around the pacemaker lead. The tissue buildup may be disrupted/modified using shock waves generated by the catheter, the cutting mechanism of the catheter, or both, as described in further detail below with reference to the remainder of the method

1300, and the catheter can then be advanced further along the pacemaker lead to another treatment site. This process can be repeated along the pacemaker lead to the location where it is lodged into the heart tissue.

At block 1304, the method 1300 may include generating one or more shock waves that propagate distally of the catheter body toward the target treatment site. The shock waves may break up calcified/fibrotic tissue on a portion of the pacemaker lead that has been inserted into the catheter (e.g., via a nozzle), for instance, once the catheter has been advanced along the pacemaker lead to the region of tissue buildup around the lead. The shock waves may be concentrated at and break up calcified/fibrotic tissue on and around the pacemaker lead at or near the nozzle outlet (e.g., within the nozzle) and/or distally of the nozzle outlet as the shock waves propagate distally from the nozzle outlet.

At block 1306, the method 1300 may include removing tissue from the pacemaker lead at the target treatment site using a cutting mechanism of the catheter. Block 1306 may be performed after shock wave generation at block 1304. Block 1306 may additionally, or alternatively, be performed prior to shock wave generation at block 1304. Block 1306 may additionally, or alternatively, be performed simultaneously with shock wave generation at block 1304. Shock wave treatment may be relatively more effective for modifying calcified tissue, and the cutting mechanism may be relatively more effective for modifying fibrous tissue. Accordingly, shock waves may be generated to disrupt hardened calcified tissue distally of the catheter body and the cutting mechanism may be used to cut away fibrotic tissue and/or the calcified tissue already subjected to shock wave treatment. However, it should be understood that shock wave treatment may effectively treat fibrotic tissue buildup, and the cutting mechanism may effectively treat calcified tissue buildup.

The cutting mechanism may, in some examples, include the distal end of the rotatable tube as described throughout this disclosure. A user may extend the cutting mechanism (e.g., the rotatable tube) distally from a distal end of the catheter by pushing against a biasing mechanism that biases the cutting mechanism proximally of the distal end of the catheter body using a user engagement on a handle of the catheter. For instance, a physician using the catheter may extend the cutting mechanism by pushing forward on a slider included on a handle of the catheter with their thumb. Once the cutting mechanism is extended distally of the distal end of the catheter body, the cutting mechanism may be rotated using another user engagement included on the catheter handle. For instance, the user may press a button on the handle using their index finger to rotate the cutting mechanism, while holding the cutting mechanism in the extended position with their thumb. The user may apply a gentle distal pressure while rotating the cutting mechanism to cut, dislodge, or otherwise modify fibrous and/or calcified tissue distal of the catheter body (e.g., attached to and/or surrounding the pacemaker lead).

At block 1308, the method 1300 may optionally include translating the cutting mechanism from an extended position to a retracted position. For instance, the cutting mechanism may be retracted such that its distal end is positioned proximally of a distal end of the catheter body and/or the nozzle in examples where the catheter includes a nozzle. The cutting mechanism may be automatically retracted when a user releases a user engagement due to a biasing member that biases the cutting mechanism to the retracted position, as described throughout. For instance, the cutting mechanism may be connected to a spring that biases the cutting mechanism toward the retracted position. A user may also slide the engagement proximally to translate the cutting mechanism to the retracted position. Retracting the cutting mechanism mitigates risk of a user inadvertently cutting the body lumen as the catheter is navigated within the body lumen. At block 1310, the method 1300 may optionally include advancing the catheter further along the pacemaker lead to a second target treatment site. At the second target treatment site, blocks 1302-1310 may be repeated.

Imaging devices (optionally included on the catheters described herein) may be used during method 1300 to safely remove pacemaker leads (or other cardiac device leads) from the heart and blood vessels. The imaging component, often involving fluoroscopy or other advanced imaging techniques such as intracardiac echocardiography (ICE), can provide real-time visualization of the lead and surrounding structures, ensuring precision and minimizing the risk of complications during the extraction process. During a pacemaker lead extraction procedure, the lead is typically removed by a specialized physician, such as a cardiac electrophysiologist or an interventional cardiologist pulling or otherwise removing the lead from the body.

Figure 14:
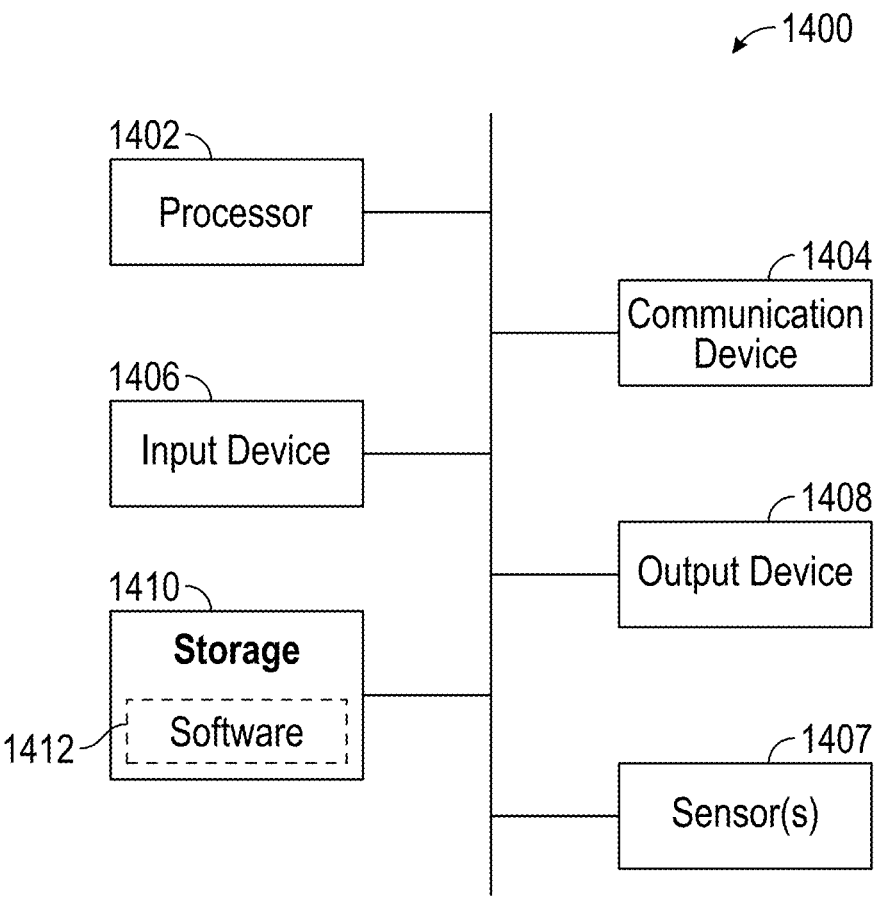
FIG. 14 illustrates an exemplary computing device according to some examples.

FIG. 14 illustrates an exemplary computing device 1400 that may form part of the system of FIG. 1 and may be used with any of the catheters and/or for performing various steps of the methods described herein, in accordance with one or more examples of the disclosure. For instance, computing device 1400 may be connected to or include one or more of the sensors described with reference to FIG. 1. The computing device may enable users of the catheters described herein to monitor parameters such as pressure, temperature, voltage, etc. The computing device may enable users of the catheters described herein to monitor aspects of treatment using visualization elements provided on the catheter. For instance, computing device 1400 may include or be connected to one or more cameras provided on the catheters described herein and may enable a user to see a visualization of the cutting mechanism during treatment within a body lumen. Device 1400 can be a host computer connected to a network. Device 1400 can be a client computer or a server. As shown in FIG. 14, device 1400 can be any suitable type of microprocessor-based device, such as a personal computer, workstation, server, or handheld computing device (i.e., a portable electronic device) such as a phone or tablet. The device can include, for example, one or more of processors 1402, input device 1406, sensor device 1407, output device 1408, storage 1410, and communication device 1404. Input device 1406 and output device 1408 can generally correspond to those described above and can be either connectable or integrated with the computer.

Input device 1406 can be any suitable device that provides directed input, such as a touch screen, keyboard or keypad, mouse, or voice-recognition device, in other words, input or directions are provided or initiated by a user. Sensor device 1407 can be one or more of any suitable sensor devices, such as a pressure sensor, a thermal sensor, an electrical sensor (e.g., current, voltage, resistance, and/or impedance sensors), or a visualization element. Output device 1408 can be any suitable device that provides output, such as a touch screen, haptics device, or speaker. Storage 1410 can be any suitable device that provides storage, such as an electrical, magnetic, or optical memory, including a RAM, cache, hard drive, or removable storage disk. Communication device 1404 can include any suitable device capable of transmitting and receiving signals over a network, such as a network interface chip or device. The components of the computer can be connected in any suitable manner, such as via a physical bus or wirelessly.

Sensor devices 1407 can provide feedback to an operator using device 1400 by measuring parameters in the surrounding environment and thereby indicating a status of a shock wave catheter device such as catheter 10 connected to computing device 1400, and further providing for guidance on what additional steps the operator may decide to implement for a shock wave catheter device such as catheter 10 connected to computing device 1400. For example, in implementations where sensor devices 1407 include pressure sensors, a slight decrease in pressure may indicate success at cracking a calcified lesion, due to the fact that an expandable member (e.g., enclosure 30) surrounding shock wave emitters is able to further expand without changing the volume of fluid within the expandable member. Further, a significant decrease in pressure may indicate a rupture failure mode where the expandable member has lost seal and fluid volume, and thus guiding toward withdrawal of the device (e.g., device 1400). In implementations where the sensor devices include a visualization element, an operator of a catheter device such as catheter 10 may be able to more clearly understand where the catheter is located relative to a target lesion or anatomy, prior to, during, and after delivering therapy.

In some embodiments, sensor device 1407 includes surface electrodes of an electrocardiograph to synchronize a shock wave to the "R" wave for treating vessels near the heart. Sensor device 1407 may include an R-wave detector and a controller to control the high voltage switch. Mechanical shocks can stimulate the heart muscle and could lead to an arrhythmia. While it is unlikely that shock waves of such short duration as contemplated herein would stimulate the heart by synchronizing the pulses (or bursts of pulses) with the R-wave, an additional degree of safety may be provided when used on vessels of the heart or near the heart. In implementations where shock waves are generated from open unenclosed emitters, synchronization to the R-wave would significantly improve the safety against arrhythmias.

Software 1412, which can be stored in storage 1410 and executed by processor 1402, can include, for example, the programming that embodies the functionality of the present disclosure (e.g., as embodied in the devices described above). Software 1412 can also be stored and/or transported within any non-transitory computer-readable storage medium for use by, or in connection with, an instruction execution system, apparatus, or device, such as those described above, that can fetch instructions associated with the software from the instruction execution system, apparatus, or device and execute the instructions. In the context of this disclosure, a computer-readable storage medium can be any medium, such as storage 1410, that can contain or store programming for use by, or in connection with, an instruction execution system, apparatus, or device. Software 1412 can also be propagated within any transport medium for use by, or in connection with, an instruction execution system, apparatus, or device, such as those described above, that can fetch instructions associated with the software from the instruction execution system, apparatus, or device and execute the instructions. In the context of this disclosure, a transport medium can be any medium that can communicate, propagate, or transport programming for use by, or in connection with, an instruction execution system, apparatus, or device. The transport medium can include, but is not limited to, an electronic, magnetic, optical, electromagnetic, or infrared wired or wireless propagation medium.

Device 1400 may be connected to a network, which can be any suitable type of interconnected communication system. The network can implement any suitable communication protocols and can be secured by any suitable security protocols. The network can comprise network links of any suitable arrangement that can implement the transmission and reception of network signals, such as wireless network connections, T1 or T3 lines, cable networks, DSL, or telephone lines. Device 1400 can implement any operating system suitable for operating on the network. Software 1412 can be written in any suitable programming language, such as C, C++, Java, or Python. In various embodiments, application software embodying the functionality of the present disclosure can be deployed in different configurations, such as in a client/server arrangement or through a Web browser as a Web-based application or Web service, for example.

Device 1400 may be configured to selectively control the delivery of energy from one or more of energy sources (e.g., a voltage pulse generator or a light energy source) to one or more acoustic energy emitters (e.g., a forward-firing emitter, a radially-firing emitter, an unenclosed emitter, or an enclosed emitter) depending on input from input device 1406.

Device 1400 may be configured to tune the energy properties of energy delivered to one or more of the above-described emitters based on tissue properties received from sensor device 1407. Tissue properties may include lesion tissue type (e.g., calcific, thrombic, fibrotic), lesion morphology (e.g., thickness, length, eccentricity).

According to aspects of the disclosure, a method of refurbishing a shock wave catheter may include replacing or repairing one or more components of the catheter, such as a nozzle, cutting mechanism, electrode, catheter body, wiring, and so on. For example, a nozzle may be replaced by detaching the nozzle from a distal end of a catheter attaching a new nozzle to the distal end of the catheter. This may include screwing/unscrewing the nozzle from the catheter, prying the nozzle from the catheter, cutting the nozzle from the catheter, etc. In some examples, the nozzle may be refurbished either in place or after having been removed from the catheter. Refurbishment of the nozzle may include, for example, unclogging the nozzle and/or sharpening a beveled edge of a cutting mechanism. Refurbishing of a catheter may include replacing one or more components of a shock wave emitter assembly. This can include replacing one or more wires or removing a portion of one or more wires and soldering a new wire to the remaining portion and/or replacing one or more emitter sheaths. Optionally, an entire electrode assembly is removed from the catheter, repaired, and reassembled to the catheter. Optionally, an entire electrode assembly may be removed and replaced. Optionally, refurbishing a shock wave emitter assembly may include testing one or more performance parameters of a refurbished shock wave emitter. Testing may include testing the ability of the nozzle to concentrate shock waves and/or cavitation bubble, such as by generating one or more shock waves and measuring a sonic output of the catheter. Testing may include testing the shock wave emitter assembly, such as by applying one or more voltage pulses to the shock wave emitter assembly and observing whether sparks are formed and/or measuring an intensity of the resulting shock waves.

Although the electrode assemblies and catheter devices described herein have been discussed primarily in the context of treating coronary occlusions, such as lesions in vasculature, the electrode assemblies and catheters herein can be used for a variety of occlusions, such as occlusions in the peripheral vasculature (e.g., above-the-knee, belowthe-knee, iliac, carotid, etc.). For further examples, similar designs may be used for treating soft tissues, such as cancer and tumors (i.e., non-thermal ablation methods), blood clots, fibroids, cysts, organs, scar and fibrotic tissue removal, or other tissue destruction and removal. Electrode assembly and catheter designs could also be used for neurostimulation treatments, targeted drug delivery, treatments of tumors in body lumens (e.g., tumors in blood vessels, the esophagus, intestines, stomach, or vagina), wound treatment, non-surgical removal and destruction of tissue, or used in place of thermal treatments or cauterization for venous insufficiency and fallopian ligation (i.e., for permanent female contraception).

In one or more examples, the electrode assemblies and catheters described herein could also be used for tissue engineering methods, for instance, for mechanical tissue decellularization to create a bioactive scaffold in which new cells (e.g., exogenous or endogenous cells) can replace the old cells; introducing porosity to a site to improve cellular retention, cellular infiltration/migration, and diffusion of nutrients and signaling molecules to promote angiogenesis, cellular proliferation, and tissue regeneration similar to cell replacement therapy. Such tissue engineering methods may be useful for treating ischemic heart disease, fibrotic liver, fibrotic bowel, and traumatic spinal cord injury (SCI). For instance, for the treatment of spinal cord injury, the devices and assemblies described herein could facilitate the removal of scarred spinal cord tissue, which acts like a barrier for neuronal reconnection, before the injection of an anti-inflammatory hydrogel loaded with lentivirus to genetically engineer the spinal cord neurons to regenerate.

It should be understood that the foregoing is only illustrative of the principles of the invention, and that various modifications, alterations and combinations can be made by those skilled in the art without departing from the scope and spirit of the invention. Any of the variations of the various catheters disclosed herein can include features described by any other catheters or combination of catheters herein. Furthermore, any of the methods can be used with any of the catheters disclosed. Accordingly, it is not intended that the invention be limited, except as by the appended claims.

The invention claimed is:

1. A catheter comprising:
   a catheter body;
   at least one shock wave emitter disposed on the catheter body; and
   a moveable shield extending at least partially around the catheter body and configured for translating along the catheter body.

2. The catheter of claim 1, wherein the shield is positionable so that the shield covers the at least one shock wave emitter.

3. The catheter of claim 2, wherein the shield is positionable so that a distal end of the shield does not cover the at least one shock wave emitter.

4. The catheter of claim 1, wherein the catheter body further comprises a central lumen configured to receive at least one of a guidewire and a pacemaker lead.

5. The catheter of claim 1, wherein the shield comprises a tapered distal end.

6. The catheter of claim 5, wherein the at least one shock wave emitter comprises a plurality of shock wave emitters, and wherein the shield is positionable with respect to the catheter body such that the tapered distal end of the shield covers at least one but not all of the plurality of shock wave emitters.

7. The catheter of claim 5, wherein the tapered distal end is configured to be extended distally of the distal end of the catheter body for piercing tissue.

8. The catheter of claim 1, comprising at least one forward firing shock wave emitter positioned at the distal end of the catheter body distally of the at least one shock wave emitter and configured to generate at least one forward propagating shock wave.

9. The catheter of claim 1, wherein the at least one shock wave emitter comprises a radially firing shock wave emitter.

10. A catheter for use in a body lumen, the catheter comprising:
a catheter body comprising a central lumen;
at least one shock wave emitter disposed at a distal portion of the catheter body and configured to generate at least one shock wave that propagates distally of the catheter body; and
a cutter configured to be translated relative to the catheter body to an extended position in which a distal end of the cutter is distal of a distal end of the catheter body for cutting tissue located distally of the distal end of the catheter body.

11. The catheter of claim 10, wherein the cutter is configured to be retracted so that a distal end of the cutter is proximal of the distal end of the catheter body.

12. The catheter of claim 10, wherein the cutter comprises a tube having a distal end configured for cutting the tissue.

13. The catheter of claim 12, wherein the distal end of the tube comprises at least one of a beveled end, a serrated end, a scalloped end, and a double beveled end.

14. The catheter of claim 12, wherein the tube is configured to extend up to 10 millimeters beyond a distal most surface of the catheter body.

15. The catheter of claim 14, wherein the catheter body comprises a nozzle and a distal end of the nozzle comprises the distal-most surface of the catheter body.

16. The catheter of claim 15, wherein the nozzle is configured to concentrate the at least one shock wave generated by the at least one shock wave emitter at the outlet of the nozzle.

17. The catheter of claim 10, wherein the cutter comprises a lumen configured to receive a pacemaker lead.

18. The catheter of claim 10, wherein the cutter is operatively connected to a user-engageable sliding component configured to enable a user to translate the cutter relative to the catheter body.

19. The catheter of claim 10, wherein the cutter is biased toward a retracted position.

20. The catheter of claim 10, wherein the cutter is rotatable relative to the catheter body, and the rotatable cutter is operatively connected to a user-engageable rotational component to enable a user to rotate the cutter.

21. The catheter of claim 10, wherein the cutter is rotatably driven by a motor.

22. The catheter of claim 21, wherein the handle comprises one or more user engagements for activating the motor.

23. The catheter of claim 10, wherein the at least one shock wave emitter is positioned radially outward of the cutter.

24. A catheter comprising:
a catheter body comprising a cavity at a distal end of the catheter body and a central lumen configured to receive at least one of a guidewire and a pacemaker lead, wherein the central lumen has a smaller diameter than the cavity at the distal end of the catheter body; and
at least one shock wave emitter positioned outwardly of the cavity and configured to generate at least one shock wave that propagates into the cavity at the distal end of the catheter body to treat target material disposed within the cavity and/or at a distal end of the cavity.

25. The catheter of claim 24, wherein the catheter body comprises an annular space configured to be fillable with a conductive fluid, wherein the at least one shock wave emitter is positioned inside the annular space.

26. The catheter of claim 24, wherein the at least one shock wave emitter comprises an emitter band.

27. The catheter of claim 26, wherein the emitter band forms a plurality of shock wave emitters.

28. The catheter of claim 24, wherein the at least one shock wave emitter comprises a plurality of shock wave emitters formed by a plurality of emitter bands, wherein each emitter band forms multiple of the shock wave emitters.

29. The catheter of claim 24, comprising at least one forward firing shock wave emitter positioned at the distal end of the catheter body distally of the at least one shock wave emitter and configured to generate at least one forward propagating shock wave.

30. The catheter of claim 29, wherein the at least one shock wave emitter and the at least one forward firing shock wave emitter are configured to generate shock waves independently.

31. The catheter of claim 24, wherein the at least one shock wave emitter comprises a radially firing shock wave emitter.

* * * * *